(12) United States Patent
Takizawa

(10) Patent No.: US 11,745,056 B2
(45) Date of Patent: Sep. 5, 2023

(54) MOTIVATIVE EXERCISE TRAINING DEVICE FOR REALIZING AUTOMATIC ASSESSMENT OF THE OPTIMAL EXERCISE INFORMATION

(71) Applicant: BIOPHILIA INSTITUTE INC., Kanagawa (JP)

(72) Inventor: Shigeo Takizawa, Fujisawa (JP)

(73) Assignee: Biophilia Institute Inc., Fujisawa (JP)

( * ) Notice: Subject to any disclaimer, the term of this patent is extended or adjusted under 35 U.S.C. 154(b) by 852 days.

(21) Appl. No.: 16/485,522

(22) PCT Filed: Feb. 14, 2018

(86) PCT No.: PCT/JP2018/005131
§ 371 (c)(1),
(2) Date: Aug. 13, 2019

(87) PCT Pub. No.: WO2018/151173
PCT Pub. Date: Aug. 23, 2018

(65) Prior Publication Data
US 2019/0366155 A1    Dec. 5, 2019

(30) Foreign Application Priority Data

Feb. 14, 2017 (JP) ................. 2017-095062

(51) Int. Cl.
*A63B 24/00* (2006.01)
*G16H 20/30* (2018.01)
(Continued)

(52) U.S. Cl.
CPC ........ *A63B 24/0062* (2013.01); *A63B 22/203* (2013.01); *G05B 19/4155* (2013.01);
(Continued)

(58) Field of Classification Search
None
See application file for complete search history.

(56) References Cited

U.S. PATENT DOCUMENTS 6,780,142 B1 * 8/2004 Takizawa ............. A63B 22/203
482/8
7,322,904 B2 * 1/2008 Takizawa ............. A63B 22/203
482/8
(Continued)

FOREIGN PATENT DOCUMENTS

JP         2002-95773 A  *  4/2002

*Primary Examiner* — Ronald Laneau

(57) ABSTRACT

A physical function training device that measuring an amount of exercise automatically enables a user to use safely by determining an appropriate amount of exercise automatically and reduces specialist labor by automatically organizing to manage the actual exercise is provided.

A physical function training device equips following; a control unit (20) is composed of a distance detection sensor (16) and, a number of times detection sensor (18) as a detection device for data related to a motion of upper or lower limbs and a storage unit (521); a control unit (20), which enables analyzing exercise data received by a detection device is composed of Various Arduino, NanpPi, RaspberryPi, microcomputer, etc.; and a storage unit (521), which is included in the control unit (20) records personal identification data, exercise data collected, collected time data of the exercise data at the time of enforcement from a time measurement apparatus (20*a*).

10 Claims, 21 Drawing Sheets

(51) Int. Cl.
*A63B 22/20* (2006.01)
*G05B 19/4155* (2006.01)

(52) U.S. Cl.
CPC ...... *G16H 20/30* (2018.01); *A63B 2024/0093* (2013.01); *A63B 2220/62* (2013.01); *G05B 2219/32339* (2013.01)

(56) References Cited

U.S. PATENT DOCUMENTS

| | | | |
|---|---|---|---|
| 7,481,739 B2 * | 1/2009 | Takizawa | A63B 23/03541 |
| | | | 482/8 |
| 11,285,356 B2 * | 3/2022 | Marti | A63B 23/1209 |
| 11,285,357 B1 * | 3/2022 | Gorin | A63B 24/0062 |
| 2004/0198564 A1 * | 10/2004 | Takizawa | A63B 22/203 |
| | | | 482/68 |
| 2004/0210168 A1 * | 10/2004 | Takizawa | A63B 23/085 |
| | | | 601/29 |
| 2018/0318639 A1 * | 11/2018 | Kim | A63B 22/205 |

* cited by examiner (a)

(b)

(c)

MOTIVATIVE EXERCISE TRAINING DEVICE FOR REALIZING AUTOMATIC ASSESSMENT OF THE OPTIMAL EXERCISE INFORMATION

TECHNICAL FIELD

This invention related to the kinetic rehabilitation training device, which can be used by the user oneself with feeling easy safely, accumulate usage information of each individual, enables the accumulated data to analyze, offering the optimal number of times of exercise and speed information that fits a user's physical condition and to enable laborsaving an analysis of required data processing for an administrator and a specialist to determine the physical condition of the user.

BACKGROUND ART

The physical function training device which was stated by the provisional publication of a patent 2010-363 which enable to prevent being used exceeding the proper amount of exercise as the U.S. Pat. No. 5,238,917 was registered.

Namely, U.S. Pat. No. 5,238,917 is characterized in that; a training board in which both the feet are kept on and of which a reciprocating movement in reciprocation in back and forth direction is available, and in the condition of its movement is available toward the right and left, setting band which hold both the legs laid in the mentioned training board, at least one of a drive unit, which makes a training board move in a reciprocation in back and forth direction or a load device, which applies a load to a training board the direction movement, at least one of a round-trip movement detection device, which detects the number of times of reciprocating motion in reciprocation in back and forth direction of a training board or a round-trip speed detection device, which detects the value of movement speed, and at least one output of detection data of a round-trip speed detection device or the round-trip movement number detection device in the outside.

And, the physical function training device stated to the provisional publication of a patent 2011-67635 which offers the lower limb function training which can prevent being used exceeding the proper amount of exercise as much as possible is registered as U.S. Pat. No. 5,238,918.

Namely, the U.S. Pat. No. 5,238,918 is characterized in physical function training device as following; training board in which both the feet are kept on, a pivot axis set in the training board and setting band which hold both the legs laid in the mentioned training board, which can rock in a vertical direction, at least one of a rocking motion number detection device that detects the number of the rocking movements of a training board or a rocking speed detection device, which detects the rocking speed of a training board is prepared, and at least one of detected data that the round-trip movement number sensing device or the movement speed detection device detects is output in the outside.

And, the physical function training device stated to the provisional publication of a patent 2011-036707 which offers a training board, which can perform alternatively, a reciprocating motion in reciprocation in back and forth direction or to rock in a vertical direction in the direction of order, which can prevent being used exceeding the proper amount of exercise as much as possible is registered as U.S. Pat. No. 4,743,562.

Namely, the U.S. Pat. No. 4,743,562 is characterized in physical function training device as following; a training board, in which both the feet are kept on, can perform alternatively, a reciprocating motion in reciprocation in back and forth direction or rock in a vertical direction in the direction of order.

A physical function training device characterizes as following; a training board, in which both the feet are kept on, can perform alternatively, a back and forth direction motion direction, one of a round-trip movement detection device, which detects the number of times of back and forth direction motion direction of a training board or a round-trip speed detection device, which detects the value of movement speed, and a training board, which both the feet are kept on is able to rock in the vertical direction and at least one of a rocking motion number detection device that detects the number of the rocking movements of a training board or a rocking speed detection device, which detects the rocking speed of a training board are prepared.

And, the physical function training device was stated to the provisional publication of a patent 2009-29162 which offers a training board, which was able to rock in a vertical direction and a pivot axis set in the mentioned training board, which was able to can perform a reciprocating motion in reciprocation in back and forth direction, which can prevent being used exceeding the proper amount of exercise as much as possible is registered as U.S. Pat. No. 4,743,557.

Namely, the U.S. Pat. No. 4,743,557 is characterized in physical function training device as following; a training board, in which both the feet are kept on, can rock in a vertical direction and a pivot axis and perform a reciprocating motion in reciprocation in back and forth direction, therefore which can perform selectively, a reciprocating motion in reciprocation in back and forth direction or to rock in a vertical direction in the direction of order.

The advantageous effect to the cerebral function, which is shown by the nonpatent literature 8-11 became apparent as the rehabilitation technique, which we used these training devices the core.

Moreover, the correlation by statistics analysis became clear about the JP nursing-care-insurance degree of care needed to the speed at the time of use and the number of times by the nonpatent literature 15, by which is consisted of a training board can perform a reciprocating motion in reciprocation in back and forth direction and by the nonpatent literature 16, by which is consisted of a training board can rock in a vertical direction.

In addition, there is the utility model registration number 2004587 of a Dorsi-Plantar Flexion training device for ankle and knee as the existing technology for the motivative exercise, which can be used a kinetic exercise for a disabled person who has the muscular power with enabling a chair seating position by his power by oneself.

Moreover, the device shown in the nonpatent literature 18 enables same kinetic rehabilitation training in the upper limbs to make them exercise in the simultaneous direction at the same time in order to hold the upper limbs, a board divided into 2 of right and left is used.

The word of the motivative exercise means moving the limbs of an affected side in the same direction simultaneously by limbs of an unaffected side and can use it also by upper or lower limbs.

Moreover, we can do the motivative exercise if one can move in the same direction simultaneously, even if any device is formed right-and-left separation.

Enforcement and the effect of the upper limbs are shown in the nonpatent literature 18.

SUMMARY OF INVENTION

Technical Problem

It was clear to advance the physical condition of patients shown in the nonpatent literature 1-11 by using devices of U.S. Pat. Nos. 5,238,918, 5,238,917, 4,743,562, and 4,743,557.

In addition, the nonpatent literature 1-7 was regarding verification of facts of over 30% of bedridden patients who treated by Takizawa method rehabilitation gained the walk again, the nonpatent literature 8-11 was regarding verification of facts of cerebral function activation and the nonpatent literature 12-13 was regarding of the device development.

Although the necessity of judging how much kinetic training being required as a result was born, there is a difference of individual physical strength and it did not come to specify.

In order to publish the nonpatent literature 15 and 16, the great labor was required, although the data had been analyzed manually.

And the data were obtained from a number of times detection device of reciprocation device or a number of times detection device of reciprocation of a training board, or a rocking number of times detection device or rocking speed obtained from a movement speed sensing device.

Since it becomes enormous profits both a researcher and a user that we can cut the labor, the improvement is desired There are data with 5000 line, and it needed to carry out processing several times to get its processed result.

Processing of the red clause was shown in an example. In addition, the table omitted the part.

The back and forth direction motion direction data, which is exercise data used for analysis is shown in the following Table 1.

TABLE 1

| | |
|---|---|
| Exercise name | KoroKoro |
| Name of facility | |
| device number | CBusRMS |
| name of Person-in-charge | |
| File name | KMS_is_110215_20110830_1016 |
| Subject code | is110215 |
| Physical condition judgment value | The degree of care |
| Sex | Woman |
| Age | 75 |
| Exercise start date | Aug. 30, 2011 |
| Start time | 10:16 |
| Exercise by time specification | 5 minutes |
| Repeat count | 334 |
| Exercise time | 272.2 seconds |
| Number of the measurement point | 5000 |
| Digitization operation data | |

| Point of measurement | Lapsed time (second) | Repeat count | Motion of the direction of order (mm) | red | |
|---|---|---|---|---|---|
| | Contact data FALSE | | | | |
| 1 | 0 | 0 | 0 | FALSE | All the isolation |
| 2 | 0 | 0 | 11 | FALSE | All the isolation |
| 3 | 0.1 | 0 | 31 | FALSE | All the isolation |
| 4 | 0.1 | 0 | 58 | FALSE | All the isolation |
| 5 | 0.2 | 0 | 84 | FALSE | All the isolation |
| 6 | 0.2 | 0 | 107 | FALSE | All the isolation |
| 7 | 0.3 | 0 | 125 | FALSE | All the isolation |
| 8 | 0.4 | 0 | 139 | FALSE | All the isolation |
| 9 | 0.4 | 0 | 143 | red | All the isolation |
| 10 | 0.5 | 0 | 138 | red | All the isolation |
| 11 | 0.5 | 1 | 120 | red | All the isolation |

TABLE 1-continued

| | | | | | |
|---|---|---|---|---|---|
| 12 | 0.6 | 1 | 93 | red | All the isolation |
| 13 | 0.6 | 1 | 66 | red | All the isolation |
| 14 | 0.7 | 1 | 38 | red | All the isolation |
| 15 | 0.7 | 1 | 8 | red | All the isolation |
| 16 | 0.8 | 1 | −21 | red | All the isolation |
| 17 | 0.8 | 1 | −38 | FALSE | All the isolation |
| 18 | 1 | 1 | −28 | FALSE | All the isolation |
| 19 | 1.1 | 1 | −10 | FALSE | All the isolation |
| 20 | 1.1 | 1 | 16 | FALSE | All the isolation |
| 21 | 1.2 | 1 | 47 | FALSE | All the isolation |
| 22 | 1.2 | 1 | 78 | FALSE | All the isolation |
| 23 | 1.3 | 1 | 104 | FALSE | All the isolation |
| 24 | 1.3 | 1 | 122 | FALSE | All the isolation |
| 25 | 1.4 | 1 | 132 | red | All the isolation |
| 26 | 1.5 | 1 | 121 | red | All the isolation |
| 27 | 1.5 | 2 | 102 | red | All the isolation |
| Omission | | | | | |
| 4976 | 270.9 | 332 | 117 | red | All the isolation |
| 4977 | 271 | 332 | 113 | red | All the isolation |
| 4978 | 271 | 333 | 101 | red | All the isolation |
| 4979 | 271.1 | 333 | 86 | red | All the isolation |
| 4980 | 271.1 | 333 | 69 | red | All the isolation |
| 4981 | 271.2 | 333 | 52 | red | All the isolation |
| 4982 | 271.2 | 333 | 36 | red | All the isolation |
| 4983 | 271.3 | 333 | 24 | red | All the isolation |
| 4984 | 271.3 | 333 | 17 | FALSE | All the isolation |
| 4985 | 271.4 | 333 | 23 | FALSE | All the isolation |
| 4986 | 271.5 | 333 | 35 | FALSE | All the isolation |
| 4987 | 271.5 | 333 | 54 | FALSE | All the isolation |
| 4988 | 271.6 | 333 | 76 | FALSE | All the isolation |
| 4989 | 271.6 | 333 | 97 | FALSE | All the isolation |
| 4990 | 271.7 | 333 | 111 | FALSE | All the isolation |
| 4991 | 271.7 | 333 | 115 | red | All the isolation |
| 4992 | 271.8 | 333 | 110 | red | All the isolation |
| 4993 | 271.8 | 334 | 98 | red | All the isolation |
| 4994 | 271.9 | 334 | 83 | red | All the isolation |
| 4995 | 272 | 334 | 65 | red | All the isolation |
| 4996 | 272 | 334 | 48 | red | All the isolation |
| 4997 | 272 | 334 | 32 | red | All the isolation |
| 4998 | 272.1 | 334 | 20 | red | All the isolation |

| 4999 | 272.2 | 334 | 17 | FALSE | All the isolation |
| 5000 | 272.2 | 334 | 21 | red | All the isolation |

From the analysis result, individual physical strength had a difference.

We did not collect contact data.

The reciprocation data which was analyzed and processed this time is shown in Table 2.

TABLE 2

| Number | Exercise situation Point number of measurement | Repeat count | Exercise time | | | |
|---|---|---|---|---|---|---|
| 1-time lapsed time/second Average | 1-time distance large/cm | 1-time distance Small/cm | | | | |
| | 1-time distance/cm Average | Average speed | Speed/m | | | |
| 1 | 5000 | 334 | 272.2 sec | 0.4 | 181 | 4 |
| | 117 | 287.2 | 10,337 | | | |
| 2 | 5000 | 216 | 276.2 sec | 0.6 | 261 | 155 |
| | 229.9 | 359.2 | 12,931 | | | |
| 5 | 5000 | 285 | 262.9 sec | 0.5 | 352 | 189 |
| | 275.8 | 600 | 21,600 | | | |
| 6 | 5000 | 279 | 285.5 sec | 0.5 | 353 | 119 |
| | 238.8 | 435.6 | 15,682 | | | |
| 7 | 158 | 8 | 266.8 sec | 10 | 93 | 4 |
| | 41 | 4.1 | 147 | | | |
| 8 | 4362 | 190 | 299.9 sec | 0.8 | 344 | 4 |
| | 216.8 | 276.1 | 9,939 | | | |
| 9 | 5000 | 314 | 282 sec | 0.4 | 198 | 28 | 157.3 |
| 350.9 | 12,631 | | | | | |
| 12 | 5000 | 429 | 281.3 sec | 0.3 | 171 | 3 |
| | 130.5 | 398.6 | 14,348 | | | |
| 13 | 5000 | 265 | 265.6 sec | 0.5 | 329 | 18 |
| | 239.4 | 478 | 17,206 | | | |
| 14 | 5000 | 166 | 278.6 sec | 0.8 | 326 | 2 |
| | 167.8 | 200.4 | 7,214 | | | |
| 16 | 5000 | 325 | 268.5 sec | 0.4 | 225 | 90 |
| | 169.1 | 410.8 | 14,787 | | | |
| 18 | 5000 | 231 | 271.6 sec | 0.6 | 256 | 15 |
| | 222.3 | 377.7 | 13,598 | | | |
| 19 | 5000 | 418 | 274.7 sec | 0.3 | 147 | 4 |
| | 93.8 | 285.6 | 10,280 | | | |
| 20 | 4983 | 338 | 300 sec | 0.4 | 166 | 7 | 122.7 |
| 277 | 9,971 | | | | | |
| 21 | 5000 | 245 | 284.6 sec | 0.6 | 179 | 28 |
| | 149.3 | 256.8 | 9,243 | | | |
| Total | Maximum value | 429 | | 10 | 353 | 189 | 275.8 |
| 600 | 21,600 | | | | | |
| | Minimum value | 8 | | 0.3 | 93 | 2 |
| 41 | 4.1 | 147 | | | | |
| | Average value | 269.5 | | 1.2 | 238.7 | 44.7 | 171 |
| 4 | 333.2 | 11,994 | | | | |

Moreover, the rocking data, which is the exercise data used for analysis, is shown in table 3 as follows.

TABLE 3

| | | | | |
|---|---|---|---|---|
| Exercise name | Patapata | | | |
| Name of facility | | | | |
| device number | CBusRMS | | | |
| name of Person-in-charge | | | | |
| File name | PTP_hy120120_20110530_1511 | | | |
| Subject code | hy120120 | | | |
| Physical condition judgment value | The degree of care | | | |
| Name | | | | |
| Sex | Man | | | |
| Age | 88 | | | |
| Exercise start date | May 30, 2011 | | | |
| Start time | 15:11 | | | |
| Exercise by time specification | 5 minutes | | | |
| Repeat count | 925 | | | |
| Exercise Time | 299.9 sec | | | |
| Number of the measurement point | 4293 | | | |
| Digitization operation data | | | | |
| Point of measurement | Lapsed time (second | Repeat count | Ankle joint angle (degrees) | Contact data |
| 1 | 0 | 0 | 0 | All the isolation |
| 2 | 1.1 | 0 | 1.2 | The right tiptoe Left heel |
| 3 | 1.1 | 0 | 2.6 | The right tiptoe Left heel |
| 4 | 1.2 | 0 | 4.4 | The right tiptoe Left heel |
| 5 | 1.3 | 0 | 5.2 | The right tiptoe Left heel |
| 6 | 1.4 | 0 | 3.4 | Right tiptoe |
| 7 | 1.5 | 1 | −4.3 | Right tiptoe |
| 8 | 1.5 | 1 | −7.5 | The left tiptoe The right tiptoe |
| 9 | 1.7 | 1 | −5.9 | The right tiptoe Left heel |
| 10 | 1.7 | 1 | 0.8 | The right tiptoe Left heel |
| 11 | 1.7 | 1 | 7 | Right tiptoe |
| 12 | 1.8 | 1 | 8.6 | All the isolation |
| 13 | 1.9 | 1 | 6.6 | Left heel |
| 14 | 1.9 | 2 | 3 | All the isolation |
| 15 | 2 | 2 | −3.4 | All the isolation |
| 16 | 2 | 2 | −6.4 | Right tiptoe |
| 17 | 2.1 | 2 | −2.1 | The right tiptoe Left heel |
| 18 | 2.2 | 2 | 0.5 | The right tiptoe Left heel |
| 19 | 2.3 | 2 | −5 | Right tiptoe |
| 20 | 2.3 | 3 | −6.1 | Left tiptoe |
| 21 | 2.4 | 3 | −2.8 | Left tiptoe |
| 22 | 2.4 | 3 | −1.9 | Right tiptoe |
| 23 | 2.5 | 3 | −5 | The right tiptoe Left heel |
| 24 | 2.6 | 4 | −1.7 | The left tiptoe The right tiptoe |
| 25 | 2.7 | 4 | 0 | Right tiptoe |
| 26 | 2.7 | 4 | −5.5 | Right tiptoe |

TABLE 3-continued

| | | | | |
|---|---|---|---|---|
| 27 | 2.8 | 5 | −7.3 | The left tiptoe The right tiptoe |
| 28 | 2.9 | 5 | −0.3 | Left heel |
| 29 | 3 | 5 | 5.3 | All the isolation |
| Omission | | | | |
| 4268 | 298.1 | 919 | −3.7 | The left tiptoe Left heel Right heel |
| 4269 | 298.2 | 919 | −6.2 | The left tiptoe Left heel |
| 4270 | 298.2 | 920 | −7.1 | The left tiptoe Left heel |
| 4271 | 298.3 | 920 | −5.9 | The left tiptoe Left heel |
| 4272 | 298.4 | 920 | −2.8 | The left tiptoe Left heel Right heel |
| 4273 | 298.4 | 920 | −1.9 | The left tiptoe Left heel |
| 4274 | 298.5 | 920 | −6.2 | The left tiptoe Left heel |
| 4275 | 298.5 | 921 | −7.5 | The left tiptoe The right tiptoe Left heel |
| 4276 | 298.7 | 921 | −5.3 | The left tiptoe Left heel Right heel |
| 4277 | 298.7 | 921 | −2.8 | The left tiptoe Left heel Right heel |
| 4278 | 298.8 | 921 | −6.6 | The left tiptoe Left heel |
| 4279 | 299 | 922 | −5.5 | The left tiptoe Left heel Right heel |
| 4280 | 299 | 922 | −3 | The left tiptoe Left heel Right heel |
| 4281 | 299.1 | 922 | −6.6 | The left tiptoe Left heel |
| 4282 | 299.3 | 923 | −3.5 | The left tiptoe Left heel Right heel |
| 4283 | 299.3 | 923 | −1.9 | The left tiptoe Left heel Right heel |
| 4284 | 299.4 | 923 | −4.6 | The left tiptoe Left heel Right heel |
| 4285 | 299.4 | 924 | −7.3 | The left tiptoe Left heel Right heel |
| 4286 | 299.5 | 924 | −5.7 | The left tiptoe Left heel Right heel |
| 4287 | 299.6 | 924 | −2.8 | The left tiptoe Left heel Right heel |
| 4288 | 299.6 | 924 | −1 | The left tiptoe Left heel Right heel |
| 4289 | 299.7 | 924 | −2.8 | The left tiptoe Left heel Right heel |
| 4290 | 299.7 | 925 | −7.5 | All the contact |
| 4291 | 299.8 | 925 | −7 | The left tiptoe The right tiptoe Left heel |
| 4292 | 299.9 | 925 | −4.8 | The left tiptoe The right tiptoe Left heel |
| 4293 | 299.9 | 925 | −1.9 | The left tiptoe Left heel Right heel |

In the evaluation of contact data, in order to collect contact data, I have arranged four sensors, but in four points, it was a one-point profitable request about the full contact value.

I was not able to analyze as a result.

The rocking data which was analyzed and processed this time is shown in Table 4.

TABLE 4

| No | Sex | Age | Exercise date | Start Time | | |
|---|---|---|---|---|---|---|
| Time | Time specification | Number of repetition | Exercise time | | | |
| | Point number of measurement | Number of times | Time | Average Sec. | Average angle | |
| | The maximum angle | | | | | |
| 17 | Man | 85 | May 31, 2011 | 10:47 | | |
| 5 minutes | 142 | 300 sec | 338 | 142 | 300 | 2.11 |
| 1.67 | 5.3 | | | | | |
| 6 | Man | 87 | May 30, 2011 | 15:11 | | |
| | 5 minutes | 925 | 299.9 sec | 4293 | 925 | 300 |
| | 0.32 | 4.16 | 16.3 | | | |
| 1 | Woman | 88 | May 31, 2011 | 14:32 | | |
| | 5 minutes | 721 | 300 sec | 3870 | 721 | 300 | 0.42 |
| 0.3 | 12 | | | | | |
| 9 | Man | 87 | May 30, 2011 | 12:12 | | |
| | 5 minutes | 922 | 299.9 sec | 2645 | 922 | 300 |
| | 0.33 | 2.11 | 12.5 | | | |
| 13 | Man | 87 | Jun. 22, 2011 | 14:32 | | |
| 5 minutes | 791 | 299.9 sec | 4264 | 791 | 300 | |
| | 0.38 | 4.9 | 17.5 | | | |
| 20 | Woman | 85 | Jun. 13, 2011 | 14:34 | | |
| 5 minutes | 372 | 300 sec | 3503 | 372 | 300 | 0.81 | 8 |
| 46 | 19 | | | | | |
| 4 | Man | 81 | Jun. 7, 2011 | 15:13 | | |
| | 5 minutes | 880 | 299.9 sec | 4560 | 889 | 300 |
| | 0.34 | 5.71 | 14.6 | | | |
| 14 | Woman | 85 | Jun. 24, 2011 | 15:05 | | |
| 5 minutes | 423 | 299.9 sec | 3130 | 423 | 300 | |
| | 0.71 | 5.81 | 18.2 | | | |
| 7 | Woman | 67 | Jun. 7, 2011 | 10:41 | | |
| | 5 minutes | 7 | 290.2 sec | 39 | 7 | 290 |
| | 41.43 | 3.39 | 8.6 | | | |
| 15 | Woman | 93 | Jun. 22, 2011 | 10:56 | | |
| 5 minutes | 471 | 300 sec | 3116 | 471 | 300 | 0.64 | 9 |
| 0.02 | 28.9 | | | | | |
| 11 | Woman | 44 | Jun. 13, 2011 | 15:17 | | |
| 5 minutes | 413 | 299.9 sec | 4912 | 413 | 300 | |
| | 0.73 | 18.54 | 39.2 | | | |
| 10 | Woman | 79 | Jun. 24, 2011 | 14:49 | | |
| 5 minutes | 530 | 300 sec | 3778 | 530 | 300 | 0.57 | 4 |
| 93 | 17.8 | | | | | |
| 12 | Man | 80 | Jun. 13, 2011 | 14:56 | | |
| 5 minutes | 681 | 299.9 sec | 3021 | 681 | 300 | |
| | 0.44 | 3.31 | 9.2 | | | |
| 2 | Woman | 84 | Jun. 22, 2011 | 11:30 | | |
| | 5 minutes | 543 | 299.8 sec | 4456 | 543 | 300 |
| | 0.55 | 7.63 | 19.4 | | | |
| 3 | Man | 75 | Jul. 13, 2011 | 14:19 | | |
| | 5 minutes | 403 | 299.9 sec | 912 | 409 | 300 |
| | 0.73 | 1.67 | 7.3 | | | |
| 8 | Woman | 74 | Jun. 22, 2011 | 14:44 | | |
| | 5 minutes | 666 | 299.9 sec | 2936 | 666 | 300 |
| | 0.45 | 2.93 | 12.5 | | | |
| 18 | Woman | 68 | May 31, 2011 | 14:09 | | |
| 5 minutes | 457 | 299.9 sec | 3975 | 457 | 300 | |
| | 0.66 | 8.99 | 19.9 | | | |
| 19 | Man | 75 | May 31, 2011 | 14:43 | | |
| 5 minutes | 700 | 299.9 sec | 3693 | 700 | 300 | |
| | 0.43 | 3.62 | 10.3 | | | |

TABLE 4-continued

| 16 | Woman | 75 | Jun. 13, 2011 | 14:03 | | | |
|---|---|---|---|---|---|---|---|
| 5 minutes | 864 | 292.6 sec | 5000 | 864 | 293 | | |
| | 0.34 | 6.23 | 15.4 | | | | |
| 21 | Woman | 92 | Jun. 24, 2011 | 13:54 | | | |
| 5 minutes | 441 | 300 sec | 2208 | 441 | 300 | 0.68 | 9 |
| 1 | 26 | | | | | | |
| 5 | Man | 84 | Jun. 13, 2011 | 15:07 | | | |
| | 5 minutes | 863 | 300 sec | 4480 | 752 | 260 | 0.35 |
| 0.36 | 19.1 | | | | | | |

Data processing by the previous device performed the calculation of average value, etc. manually.

Rehabilitation medicine cannot treat Impairment (functional damage in anatomical) by cerebral dysfunction.

Although at least one of the detection data of a round-trip movement detection device or the movement speed sensing device in a physical training device was outputted outside, users needed to calculate exercise data by them self as Table 1 to Table 4 after the output.

users needed to calculate exercise data and to input measure by hand as Table 1 to Table 4 for individual usage.

Although the previous device was composed a load device which applies a load, a drive unit which reciprocates in back and forth direction or rock in a vertical direction, and a brake device which brakes a training board based on value, users needed to calculate exercise data and to input measure by hand as Table 1 to Table 4 for individual usage.

Although the previous device was composed a load device which applies a load, a drive unit which reciprocates in back and forth direction or rock in a vertical direction, and a brake device which brakes a training board based on value, Although the previous device was composed a load device which applies a load, a drive unit which reciprocates in back and forth direction or rock in a vertical direction, and a drive unit which drives a training board based on value, users needed to calculate exercise data and to input measure by hand as Table 1 to Table 4 for individual usage.

Although the contact sensor was installed in a physical training device and the data which the contact sensor detects was outputted outside, many cases were not able to evaluate the detection data which is the contact data because a leg may not contact simultaneously to four points on a training board.

Although four sensors have been arranged in the evaluation of contact data, we could get only one full-contact value in four points.

We could not analyze as a result.

Moreover, there is a difference of individual physical strength by the result of the data analysis, and it was not able to be automated the data analysis which we use for use instruction, then the researcher had to calculate by himself as shown in Table 1 and Table 3 above-mentioned.

Furthermore, we measured by the existing device was set up by the maximum number of times of 50 times and the minimum 10 times by 10 times units each, and it produced the error by the existing device in the case of setting over 5 minutes and of measuring the operating speed for the healthy person's working speed.

Solution to Problem

A motivative exercise is moving the leg or the upper limbs of both sides in the simultaneous and the same direction, namely it is to move an affected side by a leg or an upper limb by using a device in operation of the leg of an unaffected side in the simultaneous and the same direction in operation. And a name right was entitled to as showing the nonpatent literature 14 related.

A control unit may equip a detection device, which receives exercise data of upper or lower limbs, a control unit, which can analyze exercise data that the detection device received, and a storage unit in the control unit, which is composed of personal identification data, a collected exercise data, a time data of the enforcement time, which collected the exercise data.

The control unit may process the exercise data to digital data.

The control unit may equip machine learning and artificial intelligence, i.e., AI software.

The control unit may equip a radio communication system.

The control unit, the detection device, the control unit, which can analyze exercise data that is received by a detection device, the storage unit, which can record the personal identification data in the control unit, the collected exercise mentioned above data, time data of the time to collect the exercise data, and a training board enabling motivative exercise of legs or limbs may be equipped A control unit may analyze exercise data, which corresponds to the time data.

A control unit may analyze the exercise data, which corresponds to personal identification data.

The control unit may be able to analyze the exercise data response to the time data and personal identification data.

A control unit may store the analyzed exercise data, which corresponds to the time data and the personal identification data to the memory means.

A control unit may memorize the analyzed exercise data, which corresponds to the time data to the memory means.

A control unit may show the exercise data, which was changed the digital data, which is correspond to the personal identification data at a display unit.

A control unit compares the exercise data, which was changed to the digital data to the Personal identification data; and after changing to a graph, which may display a graphical representation on a display unit.

A control unit may be outputting the exercise data, which was changed the digital data through the radio communications system.

The radio communications system may characterize in composing by WiFi, Bluetooth, Sigfox, and Xbee, etc.

Standards may be used such as IEEE-802.11a to IEEE-802.11ac when using WiFi for the radio communications system, The radio communications system may equip Bluetooth and a mobile phone.

A control unit calculates the maximum, the minimum, and average value automatically from exercise data and time data and may calculate basic analysis value.

The exercise data include number-of-times data, which was collected by a back and forth motion number detection sensor or a rocking motion number detection sensor.

And then a control unit computes the average value and the maximum in a predetermined time, and the minimum based on the number-of-times data and may set the computed numerical value as a basic analysis value.

The exercise data include back and forth motion distance detection data, which was collected by a back and forth motion distance detection sensor.

And then a control unit computes the average, the maximum and the minimum of value-based by the distance detection data and speed based on the time data that was collected by a time measurement apparatus respectively and may set a computed numerical value as a basic analysis value.

Whenever a control unit receives exercise data, it may calculate and accumulate basic analysis value, calculate the maximum and the minimum of value, and may set a calculated value as an accumulated analysis value.

Whenever a control unit receives exercise data, it accumulates the average, the maximum and the minimum of value automatically calculated and may calculate value accumulated analysis value.

A control unit accumulates the average, the maximum and the minimum of value automatically calculated by exercise data and time data, and then may a calculate an accumulated analysis value.

A control unit conducts a contrastive analysis of the accumulated basic analysis value and personal identification data and may be computing the accumulation analysis value according to individual.

A control unit conducts a contrastive analysis of personal identification data, exercise data and time data, and moreover accumulates the average, the maximum and the minimum of value automatically calculated and may be computing the accumulation analysis value according to individual.

A control unit conducts a contrastive analysis of the accumulated basic analysis value and personal identification data and may be computing the accumulation analysis value according to an administrator or an institution A control unit conducts a contrastive analysis of personal identification data, exercise data and time data, and moreover accumulates the average, the maximum and the minimum of value automatically calculated and may be computing the accumulation analysis value according to an administrator or an institution When the physical condition judgment value correlates with exercise data, standard judgment value may be defined.

In the case of standard judgment value and physical condition judgment value in personal identification data being correlated, a control unit conducts a contrastive analysis of them, standard judgment value for every individual may be defined.

A control unit conducts a contrastive analysis of the accumulated analysis value and physical condition judgment value in personal identification data and may define as standard judgment value.

A control unit conducts contrastive analysis a personal identification data memorized in a storage unit and accumulated analysis value, and may compute standard judgment value.

The physical condition judging value may use the degree of care used in Japan.

Physical condition judgment value, which shown as examples from Table 1 to Table 4 in a specification is the degree of care and may correlate with exercise data.

The physical condition judgment value may use other appraisal methods, such as FIM (Function Independence Measure), TUG (Timed Up to Go) of BBS (Berg Balance Scale). and 10 m walk test by increasing in examples of from now on In the case of the FIM and the TUG correlate with exercise data, it may be set as standard judgment value when the FIM and the TUG of the BBS are used as physical condition judgment value among personal identification data.

When the standard judgment value correlates with personal identification data, control unit conducts a contrastive analysis of them and may define standard judgment value, which can be commonly used from accumulated analysis value of all target people.

Exercise data include the rocking data in which the angle of rocking collected from a number-of-times or sensor distance detection sensor, and then a control unit computes the average, the maximum value and the minimum value of an angle and each angular velocity based on the rocking data and the time data which was received by a time measurement apparatus, and may set a computed numerical value as a basic analysis value.

When the basic analysis value at the time of enforcement is over the standard judgment value, or when it differs, a control unit may give an alarm.

When giving the alarm, a control unit may be carrying out radio communication simultaneously. Moreover, a control unit may be carrying out radio communication instead of giving the alarm.

An alarm may be given when the basic analysis value, which is gotten by analyzing exercise data analysis differs from a scope, which is based on the range defined on standard judgment value.

A control unit may apply a brake when the basic analysis value is over or differs the standard judgment value at the time of enforcement.

brakes may be applied when the basic analysis value, which obtains by computing exercise data at the time of enforcement, is over or differs the standard judgment value.

A control unit may drive a motor when the basic analysis value is over or differs the standard judgment value at a time of enforcement.

A motor may be driven when the basic analysis value, which obtains by computing exercise data at the time of enforcement, is over or differs the standard judgment value.

A control unit may apply load when the basic analysis value is over or differs the standard judgment value at a time of enforcement.

A load may be applied, when the basic analysis value, which obtains by computing exercise data at the time of enforcement is over or differs the standard judgment value.

Control unit analyzes and processes at least one of detection data of a number-of-times sensor or a distance detection sensor, time data and personal identification data and may be measuring speed and angular velocity of a training board enabling motivative exercise of legs or limbs simultaneously.

Exercise speed detection device may be composed with a number-of-times sensor, a distance detection sensor, and a time measurement apparatus.

Control unit analyzes and processes a training board enabling motivative exercise, at least one of detection data of a number-of-times sensor or a distance detection sensor, time data and personal identification data, or convert them into digital data that can be processed, may output converted digital data to internet or personal computer through the radio communications system.

When the basic analysis value, which is accumulated and analyzed exercise data of the training board at the time of implementation is over or differs the standard judgment value, a control unit may give the alarm.

When the basic analysis value, which is accumulated and analyzed exercise data of the training board at the time of implementation differs from a scope, which is based on the range defined on standard judgment value, a control unit may give the alarm.

With using physical function training device that is includes a training board that enables to move with legs or limbs in the same direction and simultaneously, when the basic analysis value that is analyzed exercise data by using a training board to move legs or limbs in the same direction and simultaneously at the time of enforcement, differs from a scope, which is based on the range defined in the standard judgment value, the training board may be applied a brake.

A control unit may apply a brake the training board in the case of the basic analysis value is over or differs the standard judgment value at the time of implementation.

Brakes may be applied to the training board when the basic analysis value, which is gotten by analyzing exercise data differs from the scope, which is based on the range defined on standard judgment value.

A control unit may drive the training board when the basic analysis value is over or differs the standard judgment value at a time of enforcement.

A control unit may drive the training board when the basic analysis value, which is gotten by analyzing exercise data differs from the scope, which is based on the range defined on standard judgment value.

A control unit may apply load to the training board when the basic analysis value is over or differs the standard judgment value at the time of enforcement.

A control unit may apply load to the training board, when the basic analysis value, which is gotten by analyzing exercise data at the time of enforcement differs from Scope, which is based on the range defined on standard judgment value.

The exercise data include given numbers of contact data in which indicates the status of contact of hand or feet of each contact sensor of the arbitrary number collected from the contact sensor; control unit accumulates and memorizes contact data and time data, which is received by a time measurement apparatus; and the value of exercise data, which accommodate to time data that contact sensors contact with the maximum number may be prescribed to contact value.

The contact value at the time of enforcement differs from the scope of based on the range defined in the standard judgment value; an alarm may be given.

An exercise times detection device may equip a back and forth motion number detection device or a rocking motion number detection device and a back and forth motion number detection device or a rocking motion number detection device.

An exercise speed detection device may equip a back and forth direction motion speed detection device or a rocking motion speed detection device and a back and forth motion number detection device or a rocking motion number detection device.

An exercise speed detection device, which is a back and forth direction motion speed detection device or a rocking motion speed detection device and then an exercise speed detection device, which is a back and forth direction motion speed detection device and a rocking motion speed detection device is a number-of-times sensor or a distance detection sensor, and it may use either one of that a distance measuring sensor, a rotary encoder, a photoelectric method sensor, the ultrasonic sensor, the magnetometric sensor, the accelerometer or the camera.

When the rotary encoder is used for the number-of-times detection sensor or the distance detection sensor, an exercise speed detection device may be used by one rotary encoder.

A training board enabling to perform the motivative exercise of legs or limbs and to rock in the vertical direction, and at least one of a rocking motion number detection device, which detects the number of rocking motion of a training board or a rocking motion speed detection device, With using a physical function training device, which equips training board for performing the motivative exercise of legs or limbs, when a control unit analyzed exercise data in the same direction and simultaneously by moving the training board with legs or limbs at the time of enforcement if the analyzed basic analysis value differs from the scope, which is based on the range defined in standard judgment value, a drive unit that drives the training board may be equipped, A training board enabling motivative exercise by moving legs or limbs is equipped and when the basic analysis value, which is analyzed exercise data at the time of enforcement differs from the scope, which is based on the range defined in the standard judgment value, a load device that applies load to the training board may be equipped.

A training board enabling motivative exercise by moving legs or limbs is set and when the basic analysis value, which is analyzed exercise data at the time of enforcement differs from the scope, which is based on the range defined in the standard judgment value, a load device, which applies load to the training board may be equipped.

A training board enabling motivative exercise by moving legs or limbs is set and when the basic analysis value, which is analyzed exercise data at the time of enforcement differs from the scope, which is based on the range defined in the standard judgment value, a brake device, which brakes the training board may be equipped.

There may be a case to transmit to a cloud directly.

Moreover, artificial intelligence and machine learning (henceforth AI), which analyzes have remarkable progress in recent years.

I am shown in the nonpatent literature 17.

Although an administrator needed to specify 10 times at the minimum, and 50 operations at the maximum for the current device and one needed to set to the control unit 20 based on every 10 times by existing devices; a control unit can be set automatically by the effect of AI software.

When the healthy person's exercise speed was measured in the setup for 5 minutes or more, it produced the error, but it can be improved.

Advantageous Effects of Invention

About an experiment of the reciprocation movement device in the direction of order, we opened to the public "Impact Evaluation of Motivative Exercise Effect to the Body" in the proceedings of the 20th Biophilia Rehabilitation Conference on Oct. 29, 2016, which became a basis of the patent application to apply as a regulation of the 2nd clause of Article 30 of Patent Law.

Furthermore, a paper is shown in the nonpatent literature 15 Mar. 2017 issue schedule BIOPHILIA2017-1 was published.

The result in this paper showed that there is significant correlation was obtained in between the degrees of care arranged and with back and forth direction movement distance and average speed as the maximum movement distance ($r=0.702$, $p<0.01$), the minimum movement distance ($r=0.608$, $p<0.05$), average movement distance ($r=0.745$, $p<0.01$), and average speed ($r=0.664$, $p<0.01$) in this paper.

Presumption of movement distance and speed of the person requiring care who had the fixed degree of care authorized is attained by work of AI software equipped in the control unit from this result, functional training in safely can be done at home, etc. alone by an alarm to an executive organization about exercise to differ from the scope of it.

Moreover, about the experiment of a rocking movement, the result of the research, which was done by the Kaken (A) (21249036) at the Ministry of Education, Culture, Sports, Science, and Technology is published in the BIOPHILIA2017-1 that paper issue is scheduled on March, 2017 as shown the nonpatent literature 16.

In this paper, a significant correlation was obtained between the number of times of rocking and the arranged degree of care as ($r=-0.624$, $p<0.01$).

In this result, the presumption of the number of times of rocking becomes possible, and an alarm to an executive organization about exercise to differ from the scope of it, is enabled by a work of AI software, therefore, the person requiring care who had the authorized certain amount of degree of care can be conducted functional training alone at home, etc. in safely.

From the situation shown in the task, it has a tremendous social meaning that using AI software, the data analysis, which was troublesome to the researcher, and possibility the determination of the optimal amount of exercise united with the user's physical condition found out.

Using AI software, automatic analysis of troublesome data for a researcher can be done.

Although setting united with a user's physical condition was difficult due to difference was large by an individual until now, the determination of the optimal amount of exercise is attained.

A user can check a change of his or her amount of exercise easily.

A user's physical condition can be presumed by an amount of exercise of back and forth direction movement distance, its average speed, or a number of times of a rocking movement by this invention and it is possible to grasp a user's physical condition by an amount of exercise.

In addition, although the correlation was not seen about rocking movement, angular velocity also has a possibility of becoming a standard of judgment, and it expects for future research.

Thereby, the rehabilitation medicine diagnosis and the determination of an intervention plan by the doctor and the nurse, a physiotherapist, etc. become easy.

The nonpatent literature 9 to 11 are the researches which contrasted the effect of motivative exercise and passive exercise to a brain. And it showed clearly that motivative exercise is activating the cerebral function as compared with passive exercise.

An exercise number detection device detects the number of times of a movement, and when a number of times of operation which this device detected reach the set value defined by the function of AI software, a brake device brakes to a movement of a direction of a training board.

Therefore, exercising beyond the set number of the exercise can be prevented for a patient.

As a result, a patient's excessive exercise can be prevented.

A back and forth movement distance detection device detects a back and forth direction movement distance, and when the distance of operation which it detected reaches the set value defined by the function of AI software, Therefore, exercising beyond the set a back and forth direction movement distance can be prevented for a patient.

As a result, a patient's excessive exercise can be prevented.

a rocking motion angle detection device detects a rocking motion angle, and when the rocking motion angle which it detected reaches the set value defined by the function of AI software, a brake device brakes to a rocking motion.

Therefore, exercising beyond the set rocking motion angle can be prevented for a patient.

As a result, a patient's excessive exercise can be prevented.

And in the case that the physical function training device equips a load device which loads a back and forth direction movement of a training board, when it detected reaches the set value defined by the function of AI software, it can be exercised with a load.

Moreover, in the case that the physical function training device equips a drive unit which drives a back and forth direction movement of a training board, when it detected reaches the set value defined by the function of AI software, it can exercise mandatorily.

And in the case, a brake device brakes a back and forth direction movement of the training board when it needs a long time for moving the direction, if a patient needs a long time for moving it in the direction by being tired and the value reaches the set value defined by the function of AI software reaches, it can stop the exercise by braking.

And in the case that the physical function training device equips a load device which loads on rocking in the up-and-down direction of a training board, when it detected reaches the set value defined by the function of AI software, it can be exercised with a load.

Moreover, in the case that the physical function training device equips a drive unit which makes a training board rock in the up-and-down direction of a training board, when it detected reaches the set value defined by the function of AI software, it can exercise mandatorily.

And in the case, a brake device brakes a rocking of the up-and-down direction of the training board when it needs a long time for moving the direction, if a patient needs a long time for moving it in the direction by being tired and the value reaches the set value defined by the function of AI software reaches, it can stop the exercise by braking.

As a result, I can prevent a patient's excessive movement.

By the function of AI software, due to specifying an optimal amount of individual exercise, which defines by long term data collection, an alarm for amount of exercise can be transmitted to a management center.

The management center where received the alarm can order visit directions to administrators, such as a doctor and a nurse, and a physiotherapist, a user's health care administration can be rationalized.

Although this patent explains the degree of care from correlation with the degree of care, management by evaluation of BBS (Berg Balance Scale), the gait evaluation and FIM (Functional Independence Measure), etc. becomes possible.

Namely, contrasting evaluation can be performed with an evaluation of BBS, the gait evaluation, and FIM.

Automatic analysis by AI software which occupies the core of this patent enable contrast of cerebral function revitalization and motivative exercise, restructuring of rehabilitation medicine is attained.

Activity by this patent use, which is performed by the non-profit organization social engineering study group of advanced age active citizen and English name International Biophilia Rehabilitation Academy may be able to build a new academic domain.

Furthermore, in this specification, a front and back direction and also a right and left direction of a physical function training device is set up in the same direction as front and back and also a right and left direction of the patient who uses a physical function training device.

Although four sensors were arranged in the evaluation of contact data; we could acquire only one full-contact value in four points.

Even user, who cannot contact upper or lower limbs ground level by contracture at the time of using a measurement of an optimal distance or an angle, may be attained, and by adding on contact sensors, and by conducting contrastive analysis to a specification of the most point installing and exercise data, automation of much more accurate analysis may expect in the future.

It is possible to make the functional re-acquerment effect and the cerebral function activation effect maximize utmost, that is shown in nonpatent literature.

DESCRIPTION OF EMBODIMENTS

Example 1

I explain Example 1 of a physical function training device in this invention by using FIG. 1 to FIG. 8.

Figure 1:
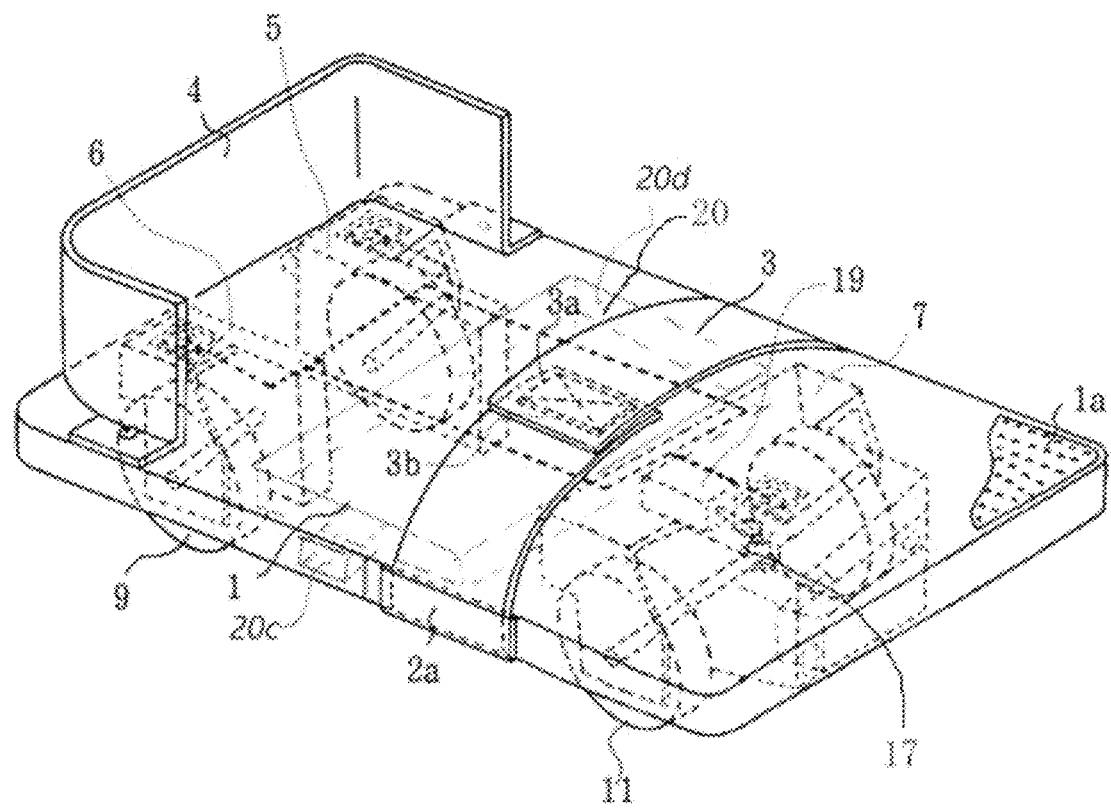
FIG. 1 is a perspective view of a physical function training device of Example 1.

FIG. 1 is a perspective view of a physical training device of Example 1.

Figure 2:
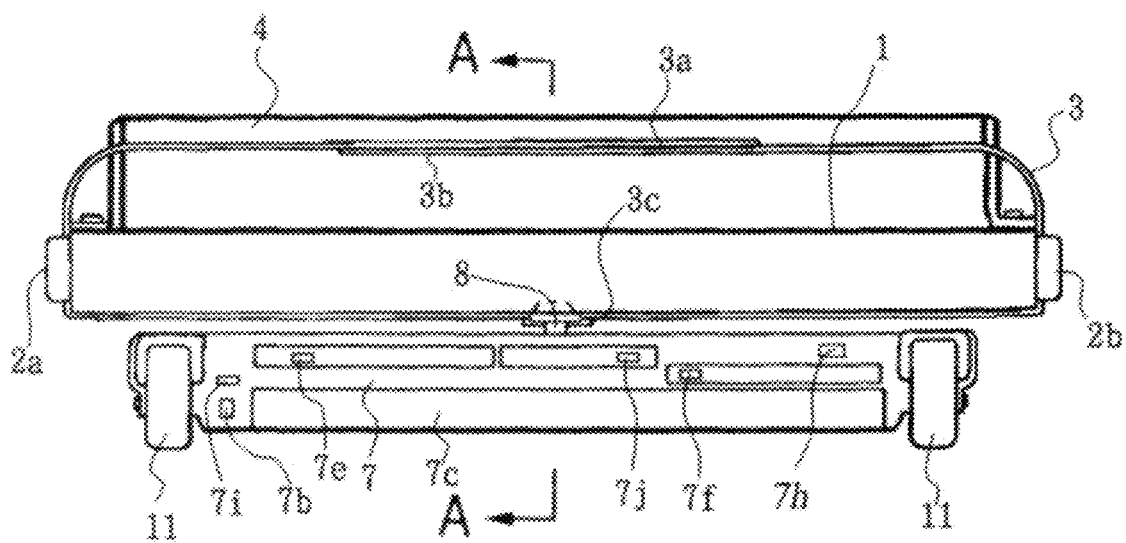
FIG. 2 is a front view of FIG. 1.

FIG. 2 is a front view of FIG. 1.

Figure 3:
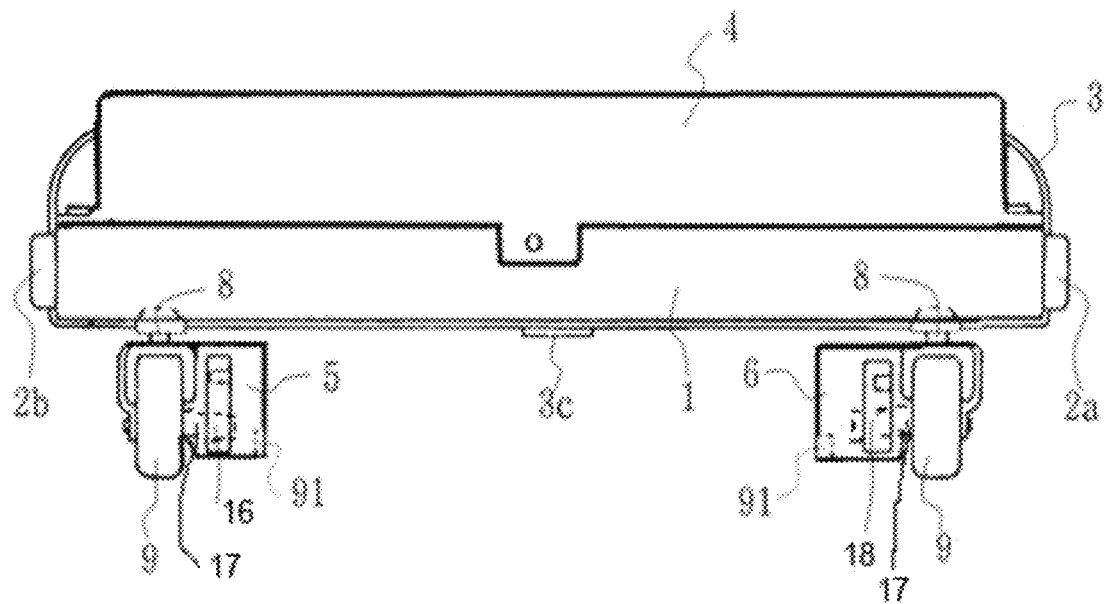
FIG. 3 is a rear view of FIG. 1.

FIG. 3 is a rear view of FIG. 1.

Figure 4:
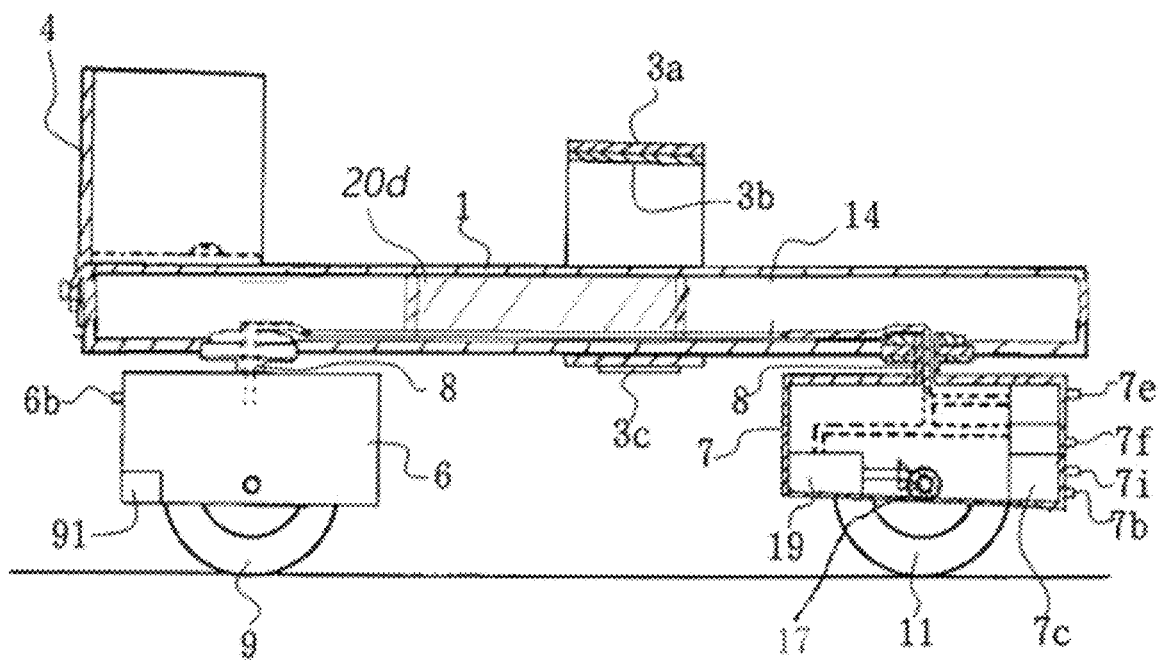
FIG. 4 is an A-A cross-section view of FIG. 2.

FIG. 4 is an A-A cross-section view of FIG. 2.

Figure 5:
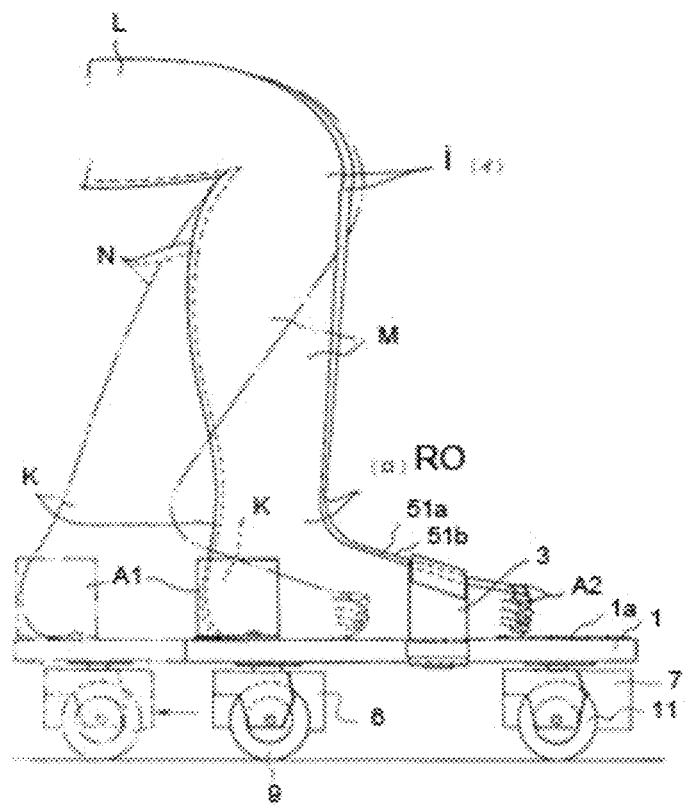
FIG. 5 is a side view while using, which sets and fixes the two legs.

FIG. 5 is a side view while using, which sets and fixes the two legs.

Figure 6:
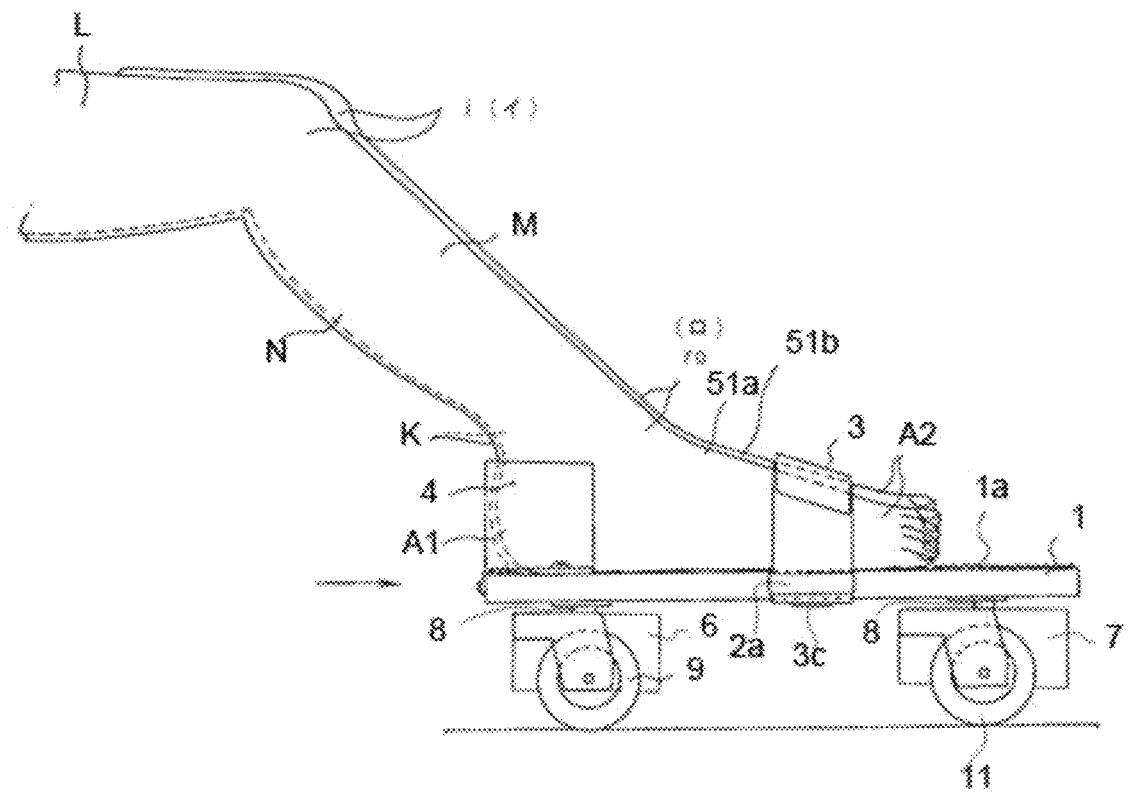
FIG. 6 is a side view showing the state of performing Plantar Flexion exercise.

FIG. 6 is a side view showing the state of performing Plantar Flexion exercise.

Figure 7:
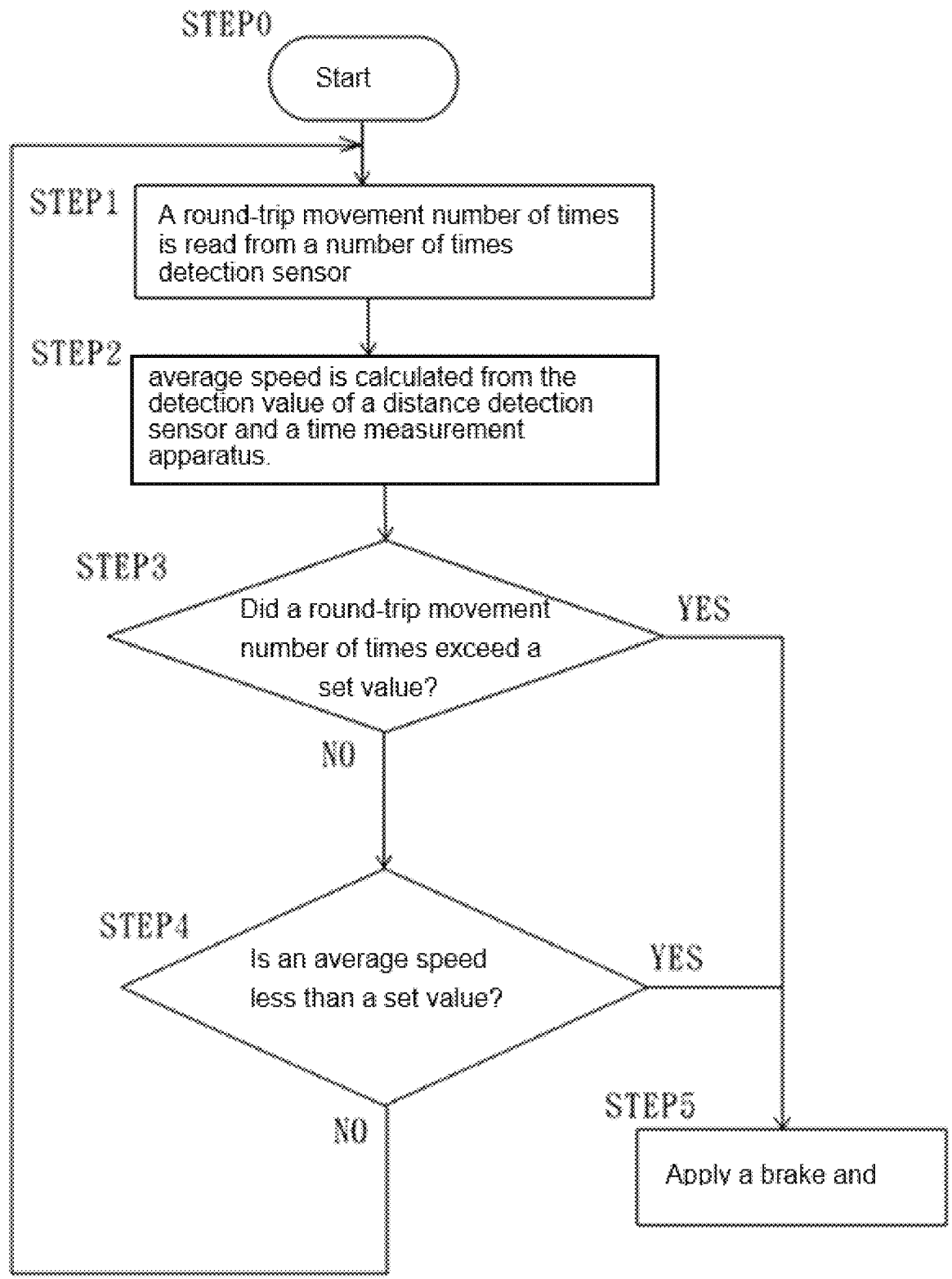
FIG. 7 is a flowchart in case, which the connection between a wheel and a motor are cut.

FIG. 7 is a flowchart in case, which the connection between a wheel and a motor are cut.

Furthermore, the drawing of a rear-wheel support part s of a right and left part is omitted in FIG. 2.

Also, the drawing of the front wheel support parts is omitted in FIG. 3.

Since a control circuit diagram is a common concept, I mention it later.

A leg shows "a leg or a hand," and both legs mean "both hands or both legs" among an explanatory note following.

Namely and henceforth, what shows the leg is "a leg or a hand" and both legs are "both hands or both legs" in notation or a Figure.

Also, leg joint "RO" shows Ankle or wrist.

Moreover, knee joint "I" shows a knee or elbow.

A training board (1) is formed with wood in midair with a plane abbreviation rectangular (when necessary, another material can be used in place of wood, such as plastic).

The training board (1) has an area of sufficient width that can put both feet (51a, 51b) (for example, the size of the side from approx 26 cm to approx 32 cm, length).

Both these legs show both hands when using it with both hands.

Therefore, a disabled person can set both feet (51*a*) and (51*b*); a foot (51*a*) with disability, which has hemiparesis of lower extremities of a nerve, decline of the lower limbs extremities muscular strength that originates from a plasmotomy of Achilles' tendon K of any of the lower extremities, a disability of a range of motion, etc. of an ankle (ankle or wrist) (ro), and also a knee (knee or elbow) (i) of any bone fracture etc. and a foot (51*b*) of the other healthy foot without any disability in the condition of sitting on a chair.

In the case of both hands, a user sits on a chair and moves device with both hands placing a device on a desk.

Figure 30:
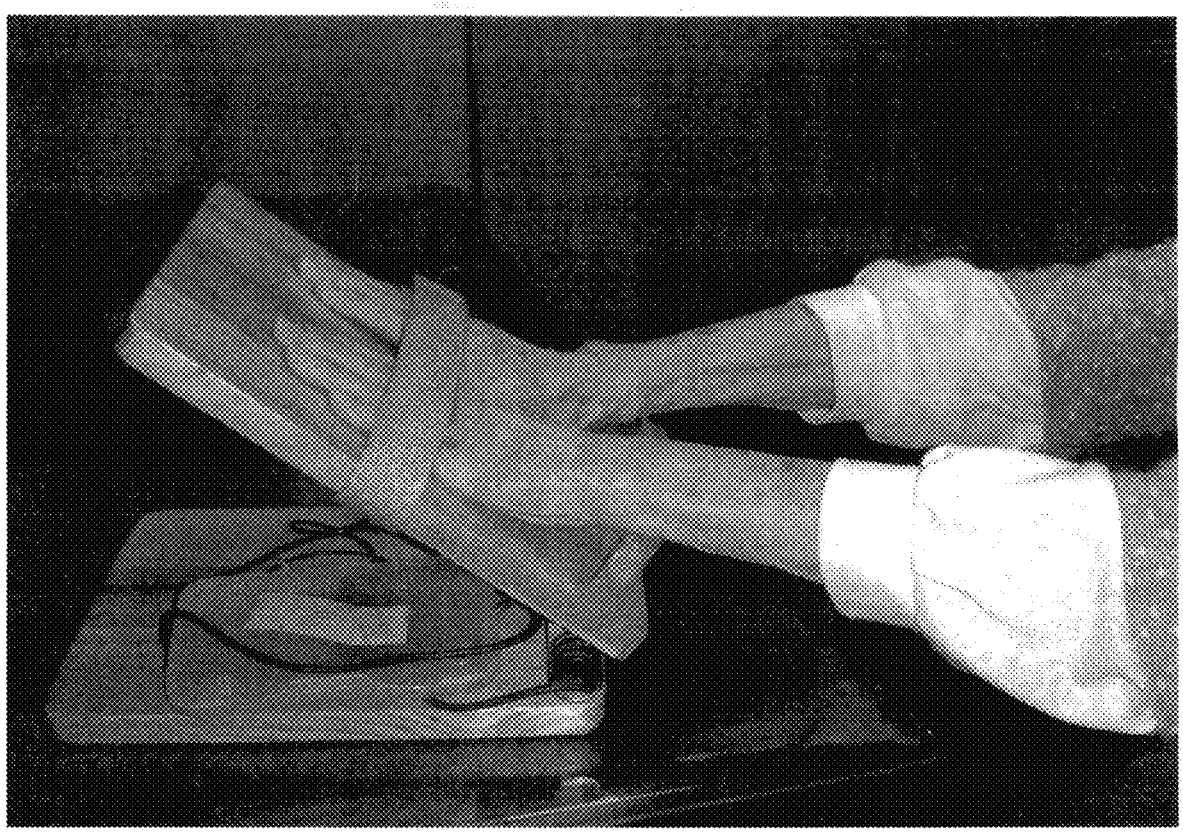
FIG. 30 is a reference diagram showing the use situation of the upper limbs about the operation of the direction of order.
Figure 31:
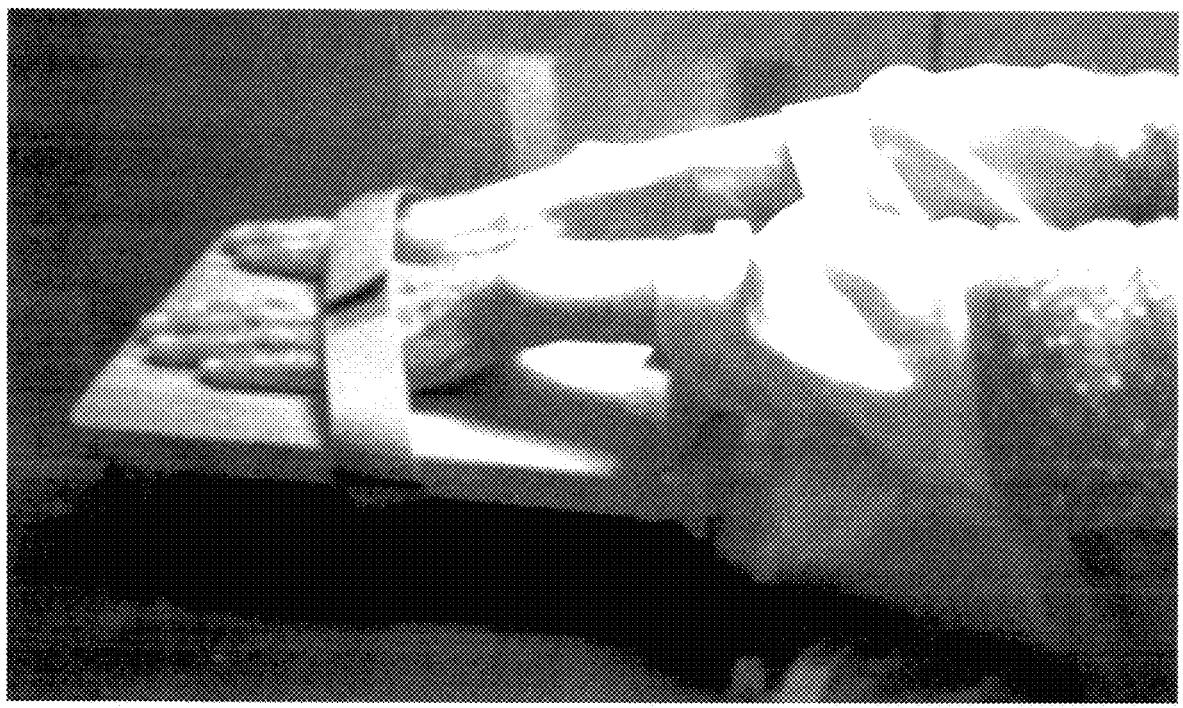
FIG. 31 is a reference diagram showing the use situation of the upper limbs about the operation of a rocking direction.

A conceptual diagram is shown in FIG. 30 and FIG. 31.

A disabled person can set both feet (51*a*) and (51*b*) in the condition of sitting on a chair; a foot (51*a*) with disability, which has a decreased upper arm muscle strength due to upper arm nerve palsy and tear of upper arm muscles, a disability of a range of motion, etc. of an ankle (ankle or wrist) (ro), and also a knee (knee or elbow) (i) of any bone fracture etc. and a foot (51*b*) of the other healthy foot without any disability.

A slip stopper (1*a*) assembles in the upper surface of a training board (1) if needed.

The slip stopper (1*a*) is formed by pasting up the rubber sheet, for example, when a training board (1) is formed by plastic, etc., it can be formed in the upper surface of a training board (1) at one.

Although a training board (1) is a hollow structure, any form may be used if an information transmission route (14) can be assembled that is composed of electric wire, etc. a control unit (20), communication tool (501) and USB port (20*c*) as a power supply information connection terminal, within the hollow space.

A heel support part (4), which is formed by belt-like straps, such as plastic, skin and cloth, for example, is almost shaped like a letter C shown in a plain view and then is fixed a training board (1) with tack wear, nail wear, screw, etc. impedes a movement to the rear of the heel (heel or wrist) of two feet (51*a*, 51*b*) if the two feet (51*a*, 51*b*) keep on the surface of a training board (1).

Furthermore, in the case that the heel (heel or wrist) support part (4) is formed from plastic, it may form a unit to a training board (1).

And also, a setting band (3) that the edge department of the right and left adhered to a training board (1) is set up both with the interval from this heel (heel or wrist) support part (4) to the front and in the omission central position of the long hand direction of a training board (1).

A setting band (3) is adhered to under the surface of a training board (1) as for the center, both end parts which pass the plane Japanese letter (KO) character form conducive brackets (2*a*,2*b*) respectively that assemble in each right and left aspect of a training board (1) of each and are keeping upward of a training board (1).

And both right and left end parts (3*a*, 3*b*) of band setting band (3) are overlapped mutually and are engaged by a proper engaging means such as a velvet fastener, snapshot, hook, etc. easily.

However, the setting band (3) is composed of one setting band, it is available to compose of two setting bands, the end parts of which are fixed in a training board (1).

The setting band (3), which covers insteps of both feet (51*a*, 51*b*) from an upper side is impeding the movement of both feet (51*a*, 51*b*) from the upper and front side.

Securing tools (3,4) that hold both feet (51*a*, 51*b*) in a training board (1) are composed by the heel (heel or wrist) support part (4) and the setting band (3).

The structure, material, etc. of securing tools (3,4) are possible to change suitably if both feet (both hands or both feet) (51*a*, 51*b*) can be kept and set on a training board (1).

Furthermore, at the condition that a patient recovered and strength of each foot can be applied to both legs, securing tools (3,4) to both legs (both hands or both feet) may be unnecessary.

The securing tools (heel or wrist) (4) are also wrist support parts.

Rear wheel support parts (5, 6) that freely rotate horizontally around a center perpendicular axis (8) are attached to each side, right and left at the lower back part of the training board (1).

And a left side rear wheel (9) is attached and rolls freely on a wheel support part (5) on the left side and the distance detection sensor (16) as a movement speed detection device that detects the rolling speed of the rear wheel (9) and brake (17) as a brake device that brakes the rotation of the left side rear wheel (9) assembly.

A right-side rear wheel (9) is attached and rolls freely on a wheel support part (6) on the right side and a number-of-times sensor (18), a round-trip movement number sensing device, that detects the number of round trip movements of the rear wheel (9) and brake (17) a brake device that brakes a rotation of the right side rear wheel (9) assembly.

Although, the rear wheels (9) move in a back and forth direction while rolling and are also capable of moving around while inclining right and/or left in a back and forth direction due to the rear wheel support parts (5,6) pivoting right and/or left.

The wheel support parts (5,6) are regulated in range (for example, approx 10 degrees right and left in both directions) and are not able to move in a side-to-side direction.

Also, a front-wheel support part (7) is attached to the front lower part of the training board (1) and pivots freely around a center perpendicular axis (8).

The right and left front wheels (11) are attached to a front-wheel support part (7) and roll freely with a motor (19) that drives the front wheels (11) and a brake (17) as a brake device that brakes a rotation of the front wheel (11) assembly.

Front wheels (11) move around a back and forth direction while inclining right and left due to the front wheel support part (7) pivoting right and left as the same the rear wheels (9).

The front-wheel support part (7) is regulated in range (for example, approx 10 degrees right and left in both directions) and are not able to move in a side-to-side direction.

Thus, this explains the reason for pivoting of the front wheels (11) and rear wheels (9) that were regulated in the condition that a side-to-side motion is directed.

This physical function training device needs to restrict the movement of a side-to-side direction in order to detect an exercise of back and forth direction and to use the data.

However, the forward direction of an exercise tends to deflect, in the same direction, of a foot (51*a*) with a disability because of the power of another healthy foot (51*b*) without any disability is strong due to setting both a foot (51*a*) with a disability and another healthy foot (51*b*) without a disability.

In this case, it becomes a corrective exercise instead of a natural exercise by readjusting to move completely straight, and then the continuation of training and exercise might be difficult due to big loads applied to a foot (51*a*) with a disability.

Thereupon as experience, in order to eliminate the difficulty of a continuation of such training and exercise, this regulates the right and left pivoting movement angles of the front (11) and rear wheels (9) that can move crosswise in line with an angle of about 10 degrees right and left from center.

Furthermore, when the training leader admits necessity and a corrective exercise (the body parts that cause abnormality by becoming contracture is corrected by exercise) is necessary, it is possible to use a corrective exercise due to making wheels (11,9) impossible to pivot in the side-to-side direction and move only as a fixed wheel which moves only in the back and forth direction of order.

A control unit 20 is composed of a detection device, which receives the data about operation of upper limbs or legs, an enforcement time control unit from a detection device of exercise data and a storage unit which records personal identification data, collected exercise data and time data, which is a time data for collecting exercise data at the time of enforcement, And a control unit (20) which consists of a microcomputer etc. is arranged in the physical function training device.

A time measurement apparatus (20a), communication tool (501), power unit (7k) such as battery, and USB port (20c) for an external power supply, or an information output terminal are composed in control unit (20) due to all those can be placed any where so that I omit to display in the Fig.

A control unit (20) is stored by a case (20d) in this embodiment.

In addition, I don't show a control unit (320) of Example 3 and a control unit (429) of Example 4 because they are the same kind of control unit as a control unit (20), and a case (20d) can be arranged anywhere.

A distance detection sensor (16) and a number-of-times sensor (18) are connected to an input side of a control unit through transmission route (14), and a blake (17), motor (19) and an external output device (91) is connected to an output side of a control unit through transmission route (14).

A distance detection sensor (16) detects a rotational speed of the rear wheel (9), namely, a movement speed of a training board (1).

Although a direction of movement has been changed alternatingly, the AI software (551) of control unit 20 can compute an average value of an exercise data by reciprocated training board (1) from a distance detection sensor (16).

Furthermore, in the case that an administrator is a doctor, a physiotherapist, an occupational therapist, a nurse, etc., he or she can define the range, etc. of an alarm from the obtained result, therefore the movement speed of training board (1) can be set optimal in a control unit (20) by a speed setting switch (7f).

Moreover, the optimal value of reciprocation of a training board (1) can be set in a control unit (20) by a reciprocating motion number setting switch (7j).

5 cm for 1 second of the minimum as speed to 50 cm for 1 second as speed can be set to a control unit 20 by a speed setting switch (7f) depending on the patient's condition And, a control unit (20) actuates all brakes (17) breaking and suspending the rear wheels (9) and front wheels (11) in the case that the average speed that is calculated with control unit (20) fell below the speed that was set up by a speed setting switch (7f).

And, it is not possible to exercise once again, because the brakes (17) are not disarmed if a release switch (7i) is not operated.

Number-of-times sensor (18) that detects the number of the reciprocating movement of a rear-wheel (9) in other words the number of the reciprocating movements of a training board (1) is output the detected number to a control unit (20).

This control unit (20) actuates all the brakes (17) to brake and to stop the rear wheel (9) and front wheel (11) in the case that detecting value of a number-of-times sensor (18) reaches a set value of a reciprocating motion setting switch (7j) by comparing the number data of the reciprocating movements from number-of-times sensor (18) to the set value.

And, it is not possible to do an exercise once again, because the brake (17) is not disarmed if a release switch (7i) is not operated.

numbers of times for exercise to do is set that every 10 times is a standard to a control unit (20) by reciprocating motion number setting switch (7j).

Furthermore, the arrangement and structure of the parts of a control unit that make it possible to induce a proper change can arrange a distance detection sensor (16) and a number-of-times sensor (18) with mixed loading to the same unit.

A time measurement apparatus and the data of the sensors of each above mentioned can be processed and measuring speed and angular velocity simultaneously can be performed.

A power switch (7b), a coercive speed setting switch (7f), a reciprocating motion number setting switch (7j), a rocking number setting switch (7h), an addition resistivity control switch (7e) and a release switch (7i) for all the releasing control are assembled in a front-wheel support part (7).

A physical function training device of Example 1 has the function as a motivative exercise device due to assembling a battery storage part (7c) as a battery, a load device of a front wheel (11) and a motor (19) as a drive unit in a front-wheel support part (7).

Namely, we set a number of the reciprocating movements of a training board (1) as the speed in increments of 5 cm by a coercive speed setting switch (7f), and also 10 times exercise movement by a coercive reciprocating motion number setting switch (7j) to the control unit (20).

Then, the control unit (20) drives the motor (19) and makes a training board (1) reciprocate at a set speed and makes a training board (1) suspend by a motor (19) suspending at the number of reciprocating movements become set value.

Thus, we can make patients exercise automatically.

Furthermore, a connection has cut the transmission system between a motor (19) and front wheel (11) with a clutch. and a load of the motor (19) is not transmitted in the case that motivative exercise is done.

Even the power source of the others such as the engine is good, although a drive unit is a motor (19).

Although a battery storage part (7c) is used by a battery, other power supplies may use, such as a rechargeable battery.

In the case that training is started from the condition without resistivity and the necessity to load for training is recognized due to the improvement of a patient function is seen, the set up of increments 1 kg is available with an additional resistivity control switch (7e) to the control unit (20), and the control unit (20) loads a resistivity that as a load etc., which is born from the turn of motor (19) on the basis of this set value to the front wheel (11).

For example in the case that there are hemiparesis after apoplexy, a decline of muscular strength of the lower extremities is caused by the rupture of the Achilles' tendon (K) and/or disabilities in the range of motion of ankles (ro) originating in a bone fracture of the lower extremities, both feet (51a, 51b) are set and fixed in a training board (1) by setting together the heels (heels or wrists) (A1) of both foot (51a) and foot (51b), foot (51a) with disability and another healthy foot (51b) without any disability to heel (heel or wrist) support part (4) and attaching foot tip (A2) by setting band (3) strapping both feet (51a, 51b), fitted in the sitting position because of Example 1 of a physical function training device is composed like this (Refer to full-line and also dashed line of FIG. 5).

A disabled person can set both feet (51a) and (51b) in the condition of sitting on a chair; a foot (51a) with a disability, which has a decreased upper arm muscle strength due to upper arm nerve palsy and tear of upper arm muscles, a disability of a range of motion, etc. of an ankle (Ankle or wrist) (ro), and also a knee (knee or elbow) (i) of any bone fracture etc. and a foot (51b) of the other healthy foot without any disability.

Herewith, the training and also bending and stretching exercises of knees (i) and flexion and dorsiflexion of ankles (ro) are done from solid line and also dashed line of FIG. 2 due to making a training board (1) move in a back and forth direction horizontally with wheels (9,11) rotated by gradually adding power while controlling subjective movement and making lower extremities extend and contract and muscular strength of lower extremities reinforce, and also expand a range of motion of knees (i) and ankles (ro) in order that foot (51b) without any disability assist foot (51a) with a disability by not increasing a burden.

In other words, in the case that a training board (1), which makes both feet (51a, 51b) set and fixe moves forward as drawing of FIG. 6, knees (i) opens from almost 90 degrees and extends, quadriceps (L) as lower extremities muscles shrink, the anterior tibial muscle (M) extends, both the gastrocnemial muscle (N) and Achilles' tendon (K) shrink and ankles (ro) flexes to plantar Flexion.

In the case that a training board (1) moves in a back and forth direction by expansion and contraction of both knees (i) and ankles (ro), so that the burden of both feet (51a, 51b) decreases, due to no side vibration but stable transfer since the front and rear, right and left are supported horizontally by four wheels (9,11) provided on the lower surface, and both feet (51a, 51b) tightened with the setting band (3) and heel (heel or wrist) support part (4) as a means to hold are held on a training board (1) and also a slip stopper (1a) assembly on a training board (1), both feet (51a, 51b) do not slip on a training board (1) but move with a training board (1).

Thus, this explains the reason for pivoting of the front wheels (9,11) and rear wheels (9) that were regulated in the condition that a side-to-side motion is directed.

A leg or both legs of the above explanation are also the same in the case of a hand, or both hands and they can be used similarly.

Although an effect of the exercises mentioned are conducive to improve disabilities, the number of the exercise performed (step 3) will stop automatically (step 5), and it is conducive to improvement of disabilities due to the number of exercises detected with number-of-times sensor (18) (step 1 of FIG. 7) and also the number of exercises that should be performed is previously set up to 10 times as a minimum and 50 times as a maximum in order that the disabled persons who have a desire to recover early as possible and who do exercises exceeding the equivalent range, which exceed best-suited exercises to them, will not get the expected improvement or is nonexistent.

Although there is a difference in the speed of movement for every person, usually speed decreases due to fatigue from a constant speed at the time of use.

Thereupon, it is conducive to improve disabilities, in the case that the detected movement speed of a training board (1) with distance detection sensor (16) (step 2) and the average speed is detected under setting speed (step 4) by setting up an increment of 5 cm in the minimum range 5 cm a second to the maximum speed of 30 cm a second to the control unit (20) previously, that it stops by the work of a brake system (step 5) by judging fatigue.

The range of users spread more and more, and a high effect is obtained because when necessity is admitted for training to adding resistivity for exercise and starting from the condition without resistivity and improvement has been seen in the function of a patient, adding resistivity in increments of 0.5 kg of load resistivity that are borne from the turn of a motor (19) by an addition resistivity control switch (7e) to an axle (11) is available.

Furthermore utility of it rose remarkably by having the devices made alternate functions as a passive exercise in the case that heavy disabled persons cannot move the device and motionlessness conditions of the lower extremities of the healthy side cannot perform the motivative exercise because it functions as a motivative exercise device and was given due to an exercise performed automatically at the speed of 5 cm increments with the minimum that was set up with a coercive speed set switch (7f) and a control unit that stops by itself within the designated number of times that is set up at increments of 10 with a coercive reciprocating motion setting switch (7j) and a rocking number setting switch (7h) being set up.

Example 2

Next, I explain Example 2 by using FIG. 8 to FIG. 12.

Figure 8:
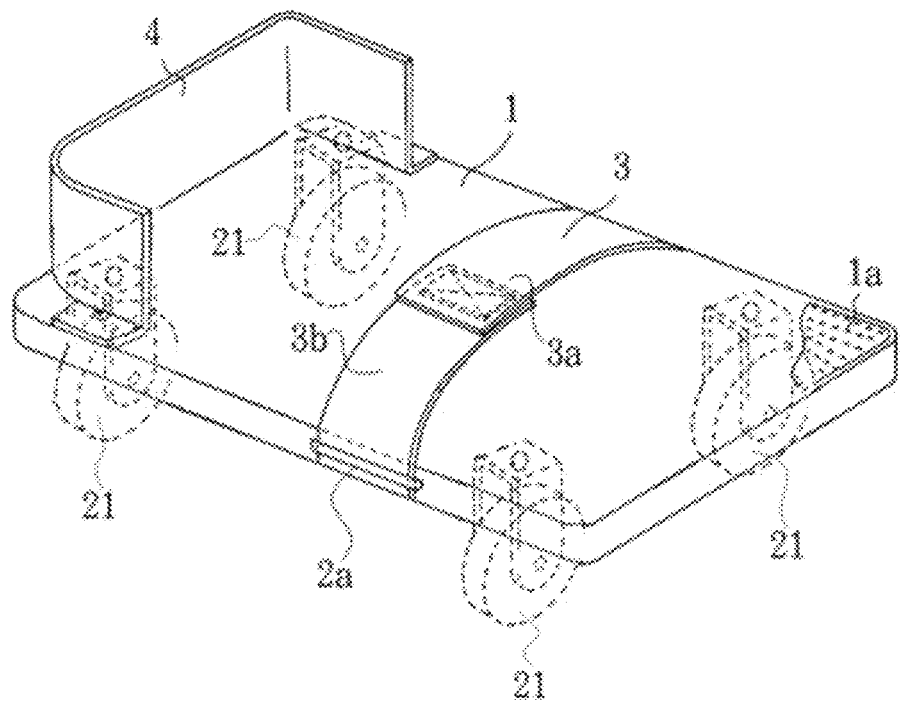
FIG. 8 is a perspective view of a training board of the 2nd embodiment.

FIG. 8 is a perspective view of a training board of Example 2.

Figure 9:
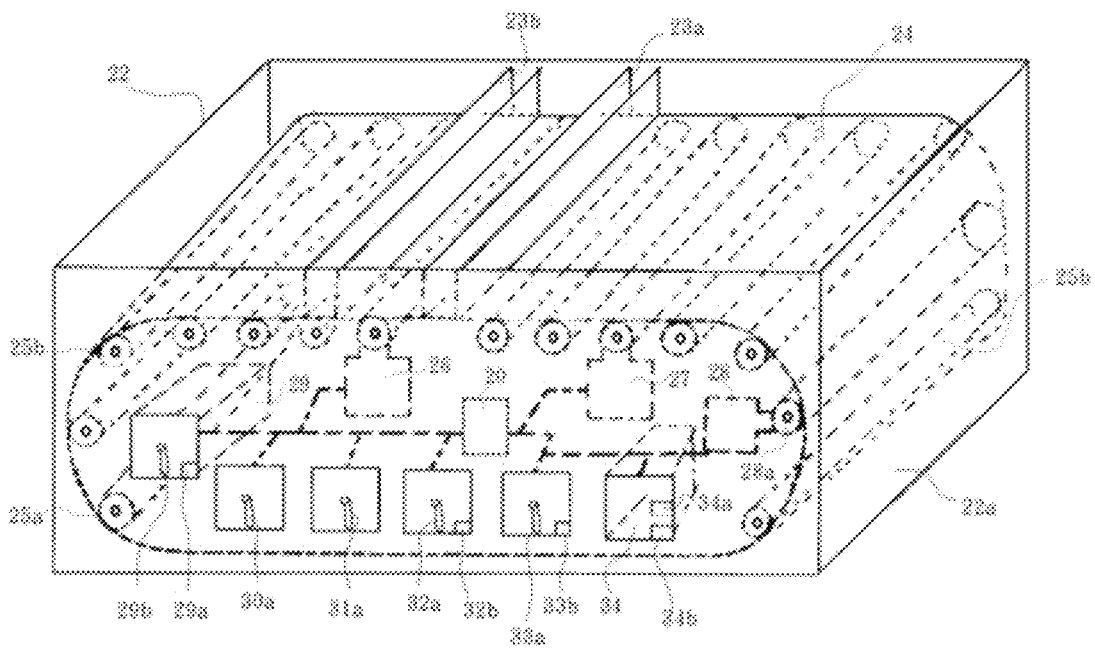
FIG. 9 is a perspective view of a training board move stand of the 2nd embodiment.

FIG. 9 is a perspective view of a training board move stand of Example 2.

Figure 10:
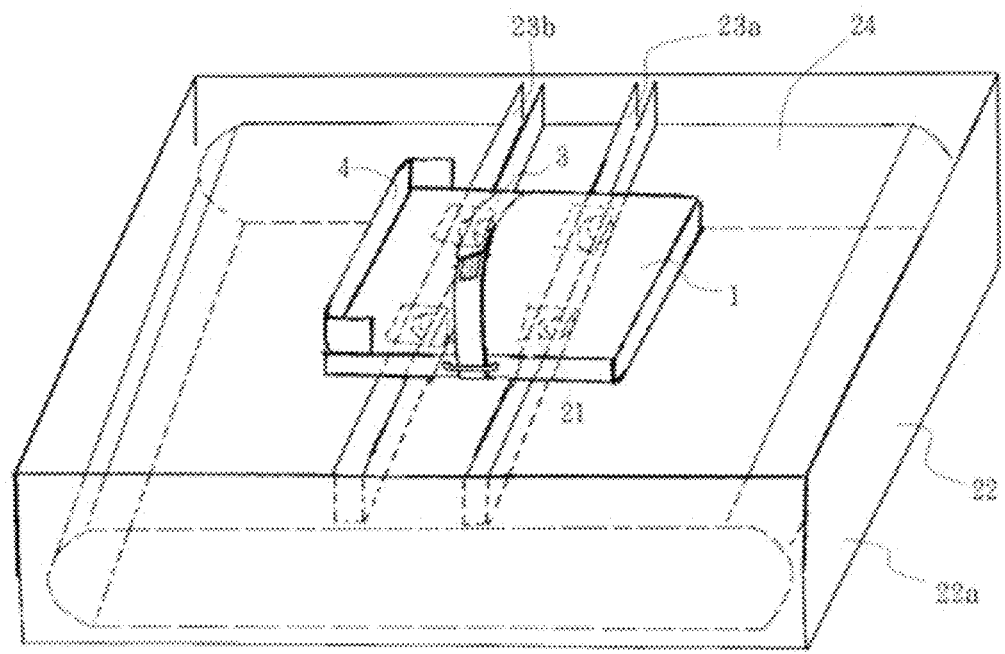
FIG. 10 is a perspective view of the 2nd embodiment.

FIG. 10 is a perspective view of Example 2.

Figure 11:
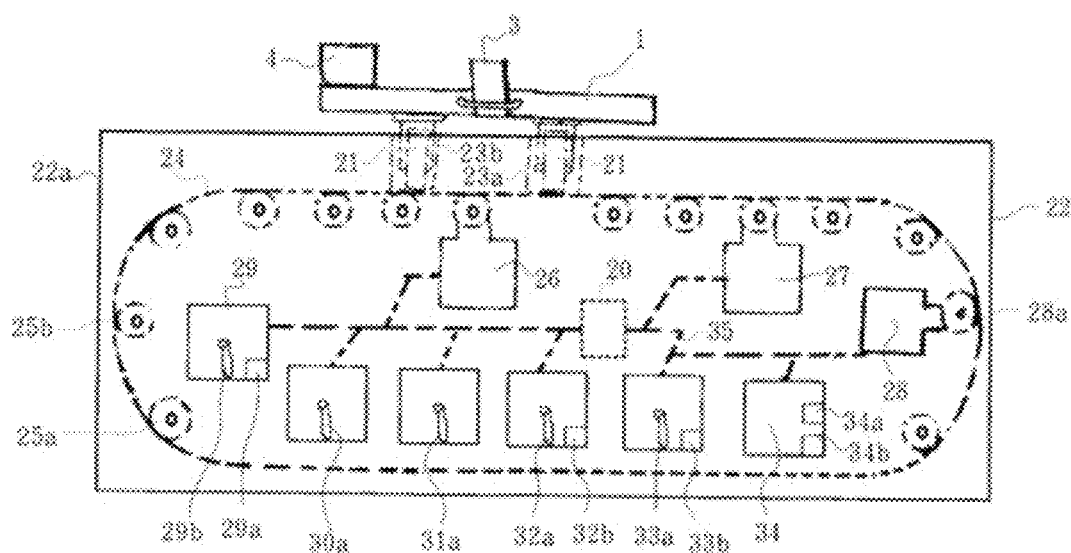
FIG. 11 is a side view of the 2nd embodiment.
Figure 12:
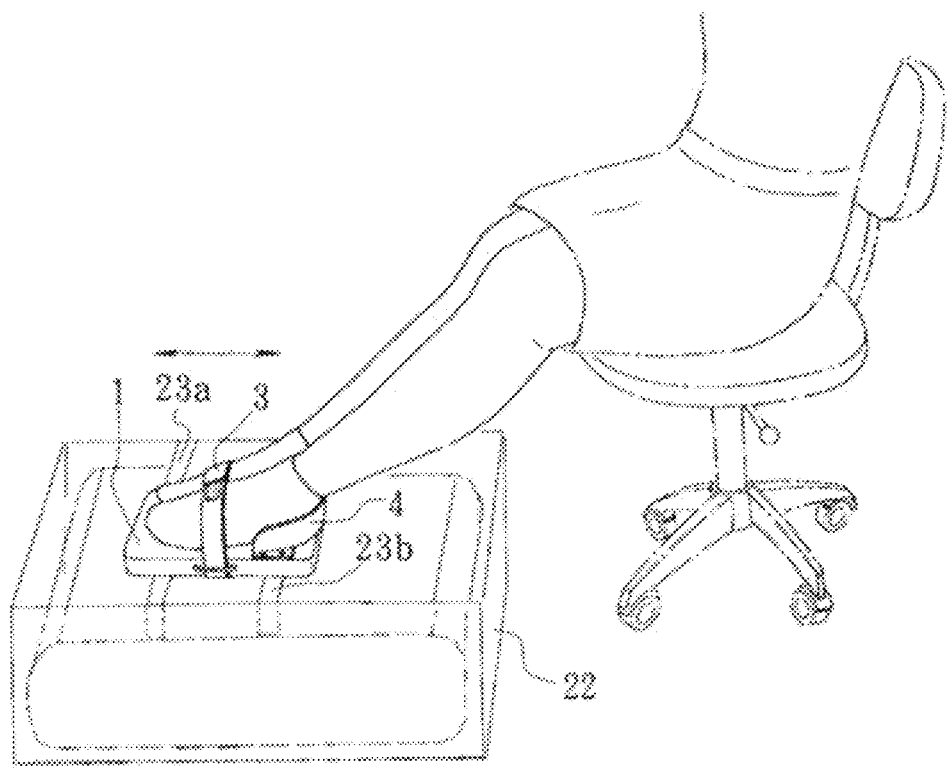
FIG. 12 is a perspective view of the 2nd embodiment in a usage state.

FIG. 11 is a side view of Example 2.

Furthermore, I omit the detailed explanation of composition elements parity to Example 1 by putting the same mark in the explanation of Example 2.

Example 2 consists of a training board (1) and a training board cart (22) as a measuring instrument and the similar functions to Example 1 are realized by combining a training board (1) and a training board cart (22).

Same as Example 1, both a heel (heel or wrist) support part (4) and setting band (3) assemble a training board (1) of this embodiment.

Several wheels (21) that may move toward the right and left freely assemble an undersurface of a training board (1).

The physical function training device needs to restrict the movement in the right-and-left direction in order to detect the movement in a back and forth direction.

However, same as Example 1, the progression of an exercise tends to deflect the foot (hand or foot) (51a) with a disability because of the strength of another healthy foot (hand or foot) (51b) without any disability is strong due to setting both a foot (hand or foot) (51a) with disability and another healthy foot (hand or foot) (51b) without any disability.

In this case, it becomes a corrective exercise instead of a natural exercise by readjusting to move forward completely, and then the continuation of training and exercise might be difficult due to big loads applied to foot (hand or foot) (51a) with disability.

Thereupon, wheels (21), which roll side-to-side, assemble on a training board (1) in order to eliminate the difficulty of the continuation of such training and exercise.

And, two pieces of the front side-wheel (21) assemble and install in a wheel bearing (23a) on the front side of a training board cart (22), and two pieces of the rear side wheel (21) assemble and install in a wheel bearing (23b) on the front side of a training board cart (22).

The number of wheels (21) selection is available if it is effective to move right and left.

The embodiment can be used as a corrective exercise when a training leader admits, and a corrective exercise is necessarily needed without using wheels (21).

A training board cart (22) consists of a box unit (22a), a top surface which is opened, wheel bearings (23a, 23b), a movable belt (24) with infinite form to back and forth direction movement, to which wheel bearings (23a, 23b) assemble, a derivation roller (25b) that guides the movable belt (24) and is supported to a box unit (22a) with a driving roller (25a) that drives the movable belt (24) and is supported to a box unit (22a) with available rotation, a distance sensor (26) (Parity to a distance detection sensor (16) of Example 1) as movement speed detection device, a number-of-times detection sensor (27) (Parity to a number of times detection sensor (18) of Example 1) as a round-trip movement number sensing device, a movable belt brake roller (28a), a brake (28) (Parity to a brake (17) of Example 1), a motor (29) (Parity to a motor (19) of Example 1) as a drive unit, a power switch (29a), an addition resistivity control switch (29b) (Parity to an addition resistivity control switch (7e) of Example 1), a speed setting switch (30a) (Parity to a speed setting switch (7f) of Example 1), a reciprocating motion number setting switch (31a) (Parity to a reciprocating motion number setting switch (7j) of Example 1), a speed setting switch (32a) (Parity to a speed setting switch (7f) of Example 1), an output device (32b), a reciprocating motion setting (33a) (Parity to a reciprocating motion number setting switch (7j) of Example 1), a reciprocating motion output device (33b), a battery set part (34), a release switch (34a) (Parity to a release switch (7i) of Example 1) for all of control releasing, external power terminal (34b), an information transmission route (35) (Parity to an information transmission route (14) of Example 1) and control unit (20).

Furthermore, every part of Example 2 effects the similar process of parity parts of Example 1 and details of the process are omitted.

Although a box unit (22a) is made of plastic, however, wood or metal are substitutes, in which the part such as rollers (25) assemble inside, and any material of sufficient strength that is possible to protect the inside on the occasion of movement, and which is free without covering the upper part that is similar to a rectangle, is formed approximately to the height of 30 centimeters, 60 centimeters to the right and left, 1 meter long, and accommodated with a measuring instrument inside.

A movable belt (24) is composed of twelve movable belt derivation rollers (25b) and a movable belt driving roller (25b) to roll freely, makes a training board (1), which assembles to move in a back and forth direction horizontally on wheel bearings (23a, 23b) that were established to a movable belt (24) move in a back and forth direction and foot (hand or foot) (51b) without any disability reinforce a foot (hand or foot) (51a) with a disability by making lower extremities bend and stretch like Example 1, trains and also exercises knee (knee or elbow) (i) extension and ankle (ankle or wrist) (ro) flexion and dorsiflexion by expanding a range of motion of knees (i) and ankles (ro).

A movable belt (24), which has durability, is formed with a material that moves freely by movable belt derivation roller (25b) and a movable belt driving roller (25a) by rolling.

Also, a brake roller (28a) contacts a movable belt (24) and is made to stop for braking, although, ordinarily, it is not contacting a movable belt (24).

A drive unit may be connected with a metallic chain structure, although a movable belt (24) is a synthetic fiber, which is weaved of metal.

Also, a movable belt (24) is good or any material that is transmitted or transmits rolling to a movable belt derivation roller (25b) and a movable belt driving roller (25a) by friction such as leather or fiber.

Twelve derivation rollers (25b) are assembled and rotate following a back and forth direction movement, which is moved by a training board (1), of a movable belt (24).

A distance sensor (26) assembles into one of the derivation rollers (25b) and a number-of-times detection sensor (27) assembles into another one of the derivation rollers (25b).

Furthermore, a brake (28) assembles into a movable belt brake roller (28a), and a brake is composed with a movable belt brake roller (28a) and brake (28).

In this embodiment, either distance sensor (26), a number-of-times detection sensor (27) and brake (28) are assembled and divided into three rollers, but a distance sensor (26), a number-of-times detection sensor (27) and a brake (28) are possible to assemble in one roller.

A movable belt driving roller (25a) is connected to a motor (29), and the movable belt driving roller (25a) rolls by the operation of the motor (29), and a movable belt (24) and a training board (1) move in a back and forth direction along with the rolling of the movable belt driving roller (25a) and the assistive-passive exercise and a resistive exercise have been realized as in Example 1

A distance sensor (26), which is parity to a distance detection sensor (16) of Example 1, detects the movement speed of a training board (1) by detecting a derivation roller (25).

A speed output device (32b) is a socket that outputs a detecting value of distance detection sensor (16) to the outside.

Any kind of terminal, which can output the detection value to the outside may be sufficient, although the structure of the USB port is made in Example 2.

A number-of-times detection sensor (27) detects a number of reciprocating movements of a training board (1) by detecting one piece of movement of derivation roller (25b).

A reciprocating motion output device (33b) is a socket that outputs detecting value by a number-of-times detection sensor (27) to the outside.

Any kind of terminal, which can output the detection value to the outside may be sufficient, although the structure of the USB port is made in Example 2.

A brake (28) for putting a movable belt (24) brake on and for making it stop is released by the signal from a release switch (34a).

Therefore, the brake (28) is not canceled, unless release switch (34a) is operated and the patient is not able to exercise once again.

A distance (speed) sensor (26) and also number-of-times detection sensor (27) are connected to the input side of a control unit (20) through an information transmission route

(35) and a brake (28), a motor (29) and external output device (32b, 33b) is connected to the output side through an information transmission route (35).

Also, an addition resistivity control switch (29b), a coercive movement speed setting switch (30a), a coercive reciprocating motion setting switch (31a), a speed setting switch (32a), a reciprocating motion setting (33a) and also a release switch (34a) are connected to a control unit (20).

And, the similar operation is performed, although it is different between the point that the movement of a training board (1) is carried out with a movable belt (24), while it is carried out with wheels (9,11) in Example 1.

It is not only a training device for effective motivative exercise, assistive-passive exercise and a resistive exercise available as Example 1, but also the structure to output value for available research, because it is able to detect an exact value about the movement around a reciprocating movement in a back and forth direction by using a movable belt (24) due to the obliqueness line being restricted in connection with detection value regarding reciprocating movement.

As mentioned above, a physical function training device assemblies with a training board (1), wheels (21) that are composed in the lower surface and move and roll toward the right and left, wheel bearings (23a, 23b) that accept the wheels (21) in the condition of its movement is available toward the right and left and can make a reciprocating movement in a back and forth direction, a distance (speed) sensor (26) that detects the movement speed of the wheel bearings (23a, 23b) and brake devices that brake on the movement in the back and forth direction of wheel bearings (23a, 23b) when the mean value of the movement speed of direction, which distance (speed) sensor (26) detected or became a value of movement smaller than a maximum speed inside a regular interval set.

Therefore, the excessive exercise of a patient can be prevented, in case a patient gets tired due to setting a movement in the back and forth direction of a training board (1) to brake.

And also it can prevent giving the influence of movement in the right and left direction of a training board (1) so that a distance (speed) sensor (26) is detecting the movement in a back and forth direction of wheel bearings (23a, 23b).

As a result, distance sensor (speed) (26) can precisely detect the movement speed in a back and forth direction of wheel bearings (23a, 23b) or a training board (1).

Example 3

Figure 13:
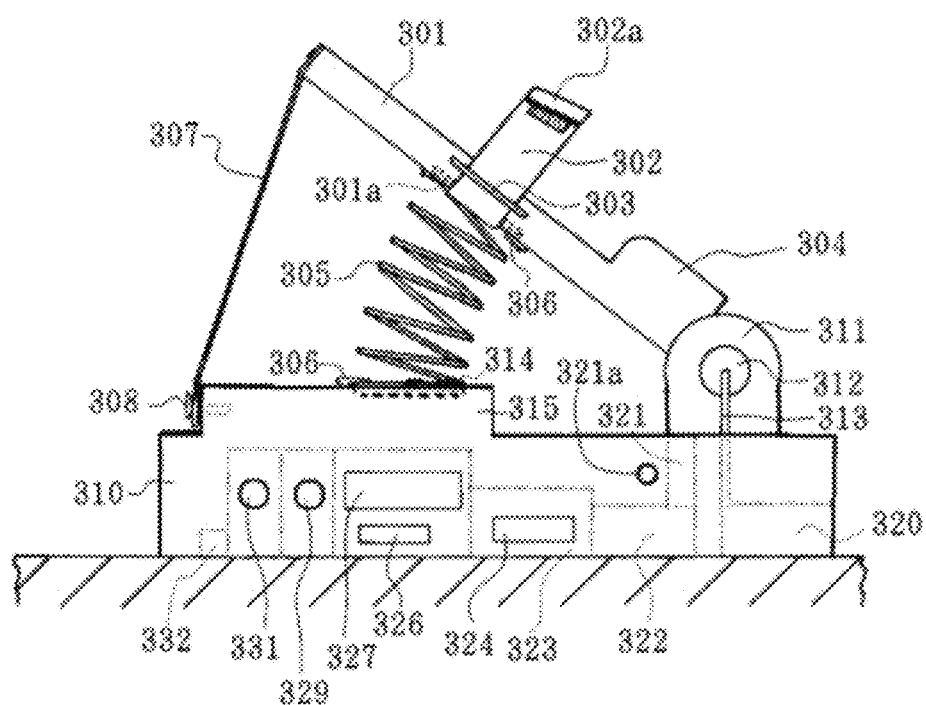
FIG. 13 is a side view of a physical function training device of the 3rd embodiment.
Figure 16:
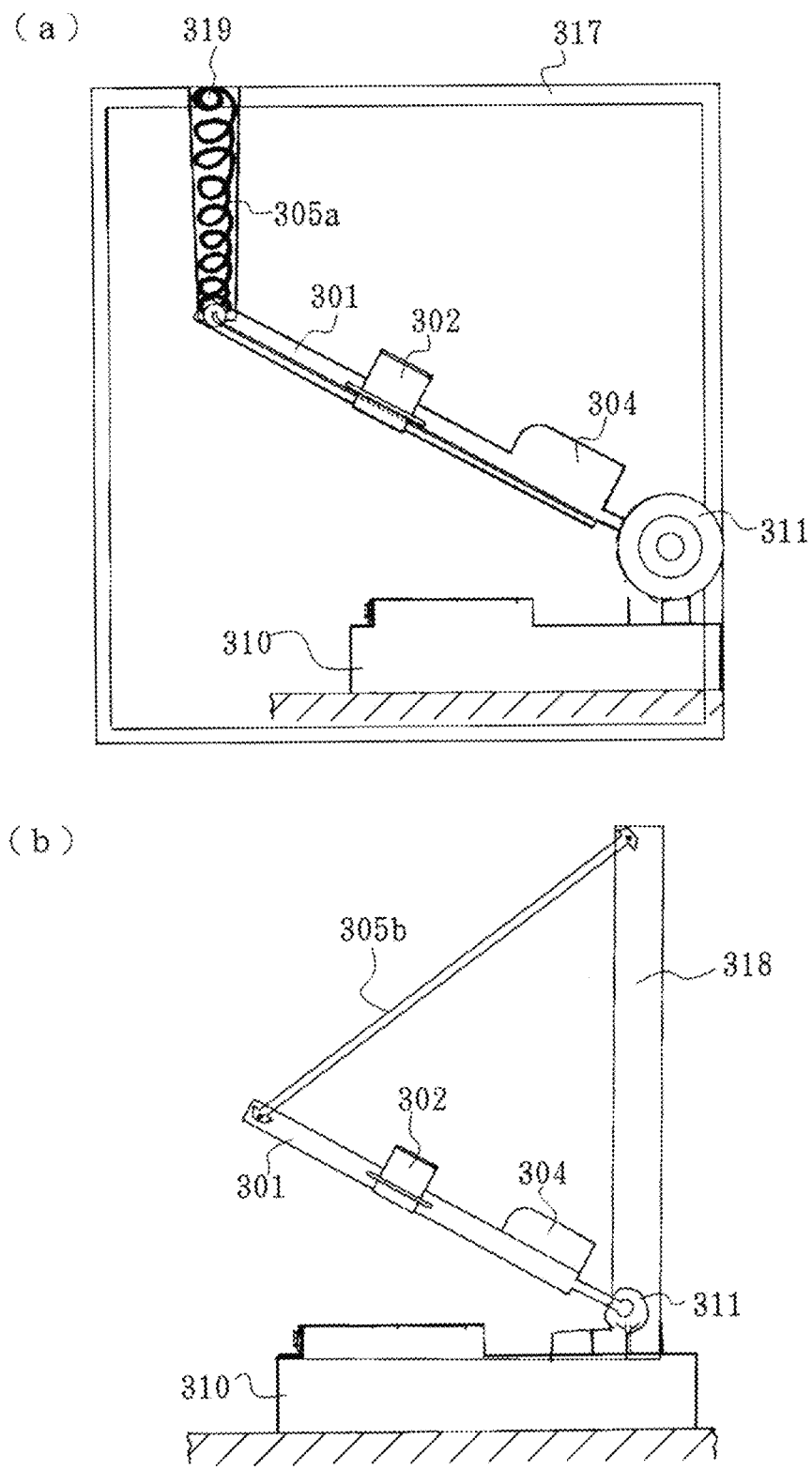
FIG. 16 is a side view of the modification of the 3rd embodiment, (a) is a view of the first modification, (b) is a view of the second modification.

Next, I explain Example 3 of a physical function training device by using FIG. 13 and FIG. 16.

FIG. 13 is a side view of a physical function training device of Example 3.

Figure 14:
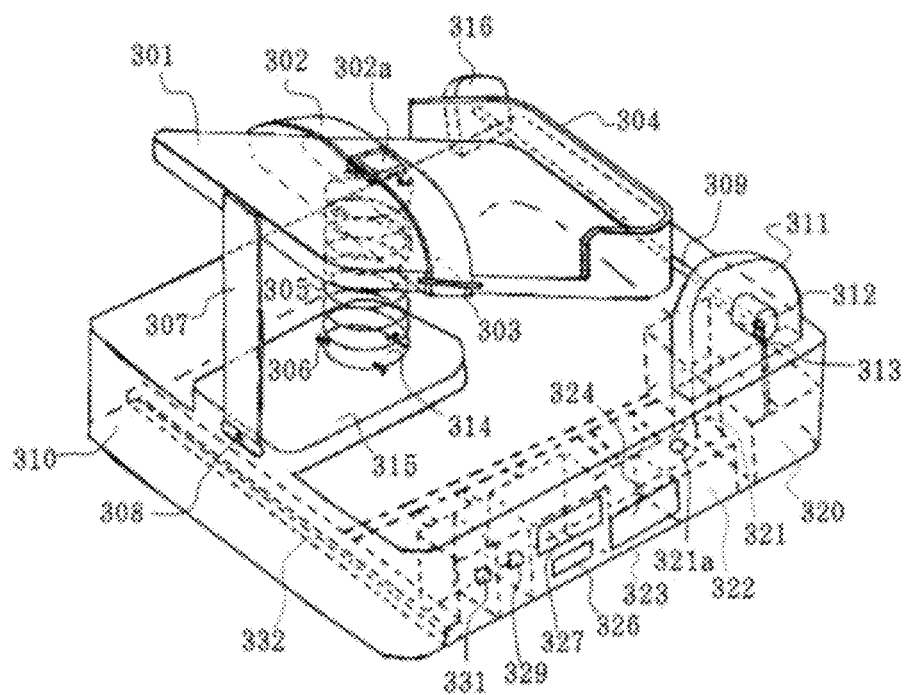
FIG. 14 is a perspective view of FIG. 13.

FIG. 14 is a perspective view of FIG. 13.

Figure 15:
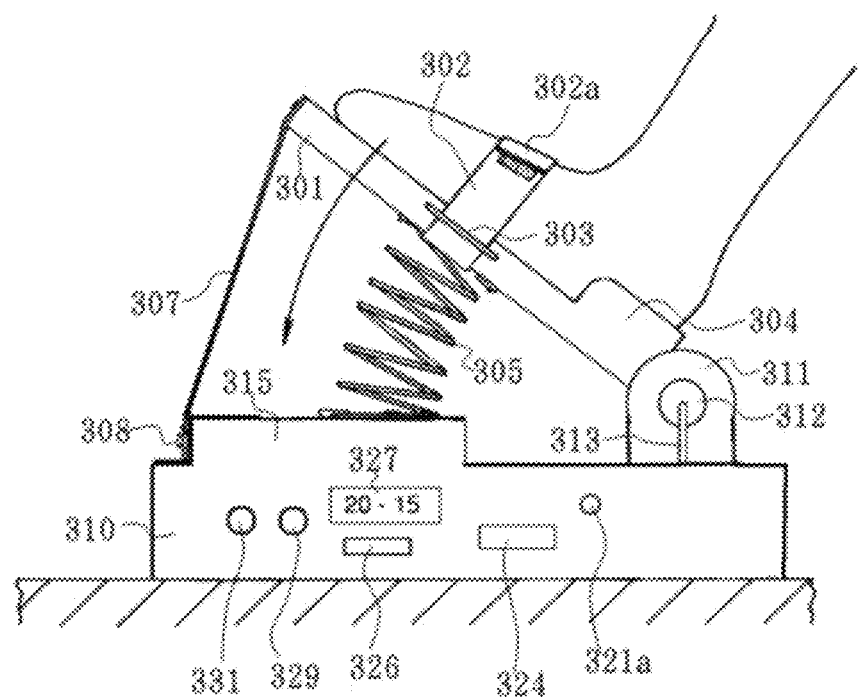
FIG. 15 is a side view while in use, which sets and fixes the two legs.

FIG. 15 is a side view while in use, which sets and fixes the two legs.

FIG. 16 is a side view of the modification of Example 3, (a) is a view of the first modification, (b) is a view of the 2nd modification.

A training board (301) is formed of plastic (or can necessarily be made of wood, etc.) and space inside with a plane similar to a rectangle.

The training board (301) has an area of sufficient width that can set both feet shown as FIG. 15 (for example, the size of the side about 20 cm and about 25 cm, length, the size of the side about 20 cm and about 35 cm, width).

Therefore, a disabled person can set both feet (feet or hands) such as a foot (foot or hand) with disability, which has hemiparesis of lower extremities of a nerve, decline of the lower limbs extremities muscular strength that originates from a plasmotomy of Achilles' tendon of any of the lower extremities, a disability of a range of motion, etc. of an ankle and any bone fracture etc. and another healthy foot (foot or hand) without any disability in the condition of sitting on a chair.

A heel (heel or wrist) support part (304) is composed of a training board (301) as a unit.

It impedes a movement to the rear of the heel (heel or wrist) of the two feet shown in FIG. 15.

Furthermore, in the case that a training board (301) is formed of wood, etc., a heel (heel or wrist) support part (304) can be composed of separated parts.

And also, a setting band (302) that the edge part of the right and left adhered to a training board (301) is set up both with the interval from this heel (heel or wrist) support part (304) to the front and approximately the central position in the long hand direction of a training board (301).

A setting band (302) sets through the undersurface of a training board (301), both end parts of which pass conducive brackets (303), which is a plane Japanese letter (KO) character form, respectively, and which assemble in each right and left aspect of a training board (301) and are kept upward of a training board (301).

And both right and left end parts (302a) of setting band (302) are overlapped mutually and are engaged by proper engaging means such as a velvet-fastener, snapshot, hook, etc.

Also, the setting band (302) is composed of one setting band, it can be composed of two setting bands, end parts of which are fixed in a training board (301).

The setting band (302) is impeding the movement to both feet from the upper and front side shown in FIG. 15.

This securing tools to hold both feet in a training board (301) as shown FIG. 15 are composed by the heel (heel or wrist) support part (204) and the setting band (302).

The structure and material etc. of securing tools (302,304) are possible to change suitably if both feet can be kept and set on a training board (301) as shown in FIG. 15.

At the condition that a patient recovered and power of each can be put into both legs, the securing tools to both legs may be unnecessary.

A load device (305) is composed of the lower part of a training board (301).

A load device (305) is a material of a spring that can be replaced in Example 3.

Spring material as the elastic body of a load device (305) in Example 3 is a load device, which adapts to a motivative exercise and gives the load repelled by total power (for example, about 20 kg) of weight of the foot (for example, about 15 kg) and power of applying a load in front of the foot (for example, about 4 kg).

The load, for which about 20 kg is exceeded, in the case of non-motivative exercise but a resistive exercise and also muscular strength exercise especially is sufficient according to a patient's situation.

Though a load device of FIG. 13 or FIG. 15 is a compression spring, a load device of FIG. 16 (a) is a tensile spring (305a) and a load device of FIG. 16b is a flexible band (305b) such as an elastic cord, which pulls up a training board (301).

The load device (305) is fixed in three places at a setting concave portion (301a), which is composed almost in the center of an undersurface of a training board (301), by mounting screws (306).

The other side is fixed in three places at a setting concave portion (314) that is composed in the upper part of a mounting convex protrusion (315) of a physical function training device cover (310) by mounting screws (306).

A gradient angle defined supporting device (307) is a cord.

An angle, which is the horizon, of a training board (301) has a range from 0 degrees of the minimum angle to 37 or 38 degrees of the maximum angle to the desired angle of a motivative exercise by the gradient angle defined supporting device (307).

And, a training board (301) becomes possible to move in this range.

The upper part of a gradient angle defined supporting device (307) is glued on a training board (301).

The lower part of a gradient angle defined supporting device (307) is fixed at the upper part of a mounting convex protrusion (315) of a physical function training device cover (310) by mounting screws (308) and it becomes easy to fix a load device (305) by mounting screws (306).

A training board (301) is held with both a brake storage bearing (311) and a bearing part (316) of a physical function training device cover (310) to a training board turn part (309), which is fixed to outside of a training board (301) as a unit with the center freely pivoting.

A training board turn part (309) perforates a brake storage bearing (311) and an accelerometer (312) is assembled at the end of a training board turn part (309).

As well, a physical function training device assembles to control unit (320), which is composed of a microcomputer, etc, an accelerometer (312) is composed on the input end of the control unit (320) through an information transmission route (313) and in the other hand a brake (321), a motor (322) as a drive unit, a display unit (327), an antenna (332) and an external output device (326) are composed on the output end of it through the information transmission route.

In addition, although an antenna (332) and an external output device (326) do not necessarily need to be included, the detection value, etc. of an accelerometer (312) can be output outside by this antenna (332) and an external output device (326).

An accelerometer (312) detects the acceleration at the time when a training board (301) is trodden downward.

The detected acceleration is transmitted to the control unit (320), which consists of a microcomputer, through the information transmission route (313).

In a control unit (320), whenever the signal of acceleration is input from an accelerometer (312), it has counted, and the number of times of rocking of a training board (301) is generated.

And a control unit (320) memorizes the acceleration, which is input from an accelerometer (312) and the number of times of rocking of a training board (301) as data in a storage unit, and outputs it suitably if needed.

In addition, a control unit (320), which consists of microcomputers has the same function as a control unit (20) of the case of Example 1.

A control unit may be arranged anywhere.

Moreover, control unit (320) has the acceleration control function, in the case that the acceleration, which is detected with an accelerometer (312), exceeds the acceleration of a regular standard value that is the setting value set up beforehand (for example, the maximum acceleration for every fixed time) or a switch (331) that was the setting acceleration value set up beforehand outputs an alarm signal and makes an alarm device drive.

For example, it can sound a buzzer or flash an indicator display unit (327) and/or transmit data from an antenna (332).

With this alarm, a caregiver can change the strength of the load device (305) into an optimum setting.

Furthermore, as mentioned above, control unit (320) is counting the number of times of rocking of a training board (301), and outputs a stop signal to brake (321) when this number of times of rocking of a fixed standard (for example, about 300 times) or the number, which was set up with a setting switch (329), is exceeded.

If a stop signal is received, brake (321) brakes a training board turn part (309) and will stop rocking.

In the case of Example 3, switch (321a) is operated manually, and this brake (321) is canceled.

Because it is used with changing a switch, it is a consideration that patients do not exercise excessively, continually and easily.

An exercise is impossible again, without releasing a brake.

Although a display unit (327) in Example 3 is a digital display screen, as long as it can display of the number of times of rocking, display of acceleration, warning, etc., any kind of display unit may be used.

Moreover, any kind of forms is sufficient although an external output device (326) in Example 3 is 10 base T.

Although an antenna (332) outputs the acceleration and the number of times, which were inputted and also can set an acceleration, a number of times of rocking, etc. to a control unit (320) with a remote control when applying a brake (321).

A battery storage part (323) shows a storage part of a battery.

Moreover, an input part (324) of external electric power is also formed.

And when a battery is used as a charging method, it is possible to charge from an input part (324) of external electric power supply.

Moreover, it is also possible to make a training board (301) rock compulsorily by a motor (322).

For example in the case that there are hemiparesis after apoplexy, a decline of muscular strength of the lower extremities is caused by the rupture of the Achilles' tendon and/or disabilities of the range of motion in ankle originating in a bone fracture of the lower extremities, both feet are set and fixed in a training board (301) by setting together heels (heels or wrists) of both feet one with a disability and another healthy foot without any disability to heel (heel or wrist) support part (304) and attaching foot tip by setting band (302) strapping both feet, fixed in the sitting position because of Example 3 of physical function training device assembled as stated (Refer to FIG. 15).

Thus, it is able to set and put on both feet with the upper surface of a training board (301) corresponding to the size of a disabled person's feet easily, because it is good that heels (heels or wrists) are set and put on to heel (heel or wrist) support part (304), setting band (302) sets and attaches foot tip in order to set and fix both feet with a training board (301).

Herewith, the training is done with rocking a training board (301) in the direction as shown with the arrow of FIG. 15 by gradually adding power while controlling subjective movement for making lower extremities expansion and contraction, muscular strength of lower extremities (ankles or wrists) reinforces and flexion and dorsiflexion of lower extremities (ankles or wrists) by expanding a range of motion of those due to healthy foot (hand or foot) assisting the foot with a disability by not increasing a burden.

Example 3 shown in FIG. 16 (a) shows that it is possible not to load from a lower part like the spring material of the load device (305), but to load away from the upper part by pulling up.

A frame (317) is a frame body that is able to include a physical function training device and a heel (heel or wrist) setting part is an opening space and is needed in order to use freely.

Moreover, it is good that security materials (319), which are crossed to both side covers of the frame (317), are sufficient to have the strength to assemble a load device (305a), for example, about 60 kg in order.

Example 3 shown in FIG. 16 (b) is used to install a pillar near heels (heels or wrists) and it is possible for a load device (305b) to be assembled.

Either one or two pillars (318) are sufficient as long as it has the intensity, which does not break, for example, when it pulls by almost 60 kg in order that it assembles a load device (305b).

In Example 3, a load device (305), which is a spring, can be any kind of material, which can apply a load such as oil pressure, air pressure and elastic pressure and also has rebounding power.

The effect of such an exercise is connected to the improvement of disabilities.

However, disabled persons, who desire to recover as soon as possible even one day earlier, exercise many times and then may exceed the range of proper quantity and may exercise.

Therefore, the improvement that is expected may not be sometimes obtained.

So that there is no such case, a number that should be exercised to a proper value is regulated by operating a brake (321) with a control unit (320).

The number of times of exercise can be set in advance by operating a setting switch (329).

And, a control unit (320) causes a brake (321) to be operated, when it becomes the setting number (300 times as an example) and suspends rocking of a training board (301).

Example 4

Figure 17:
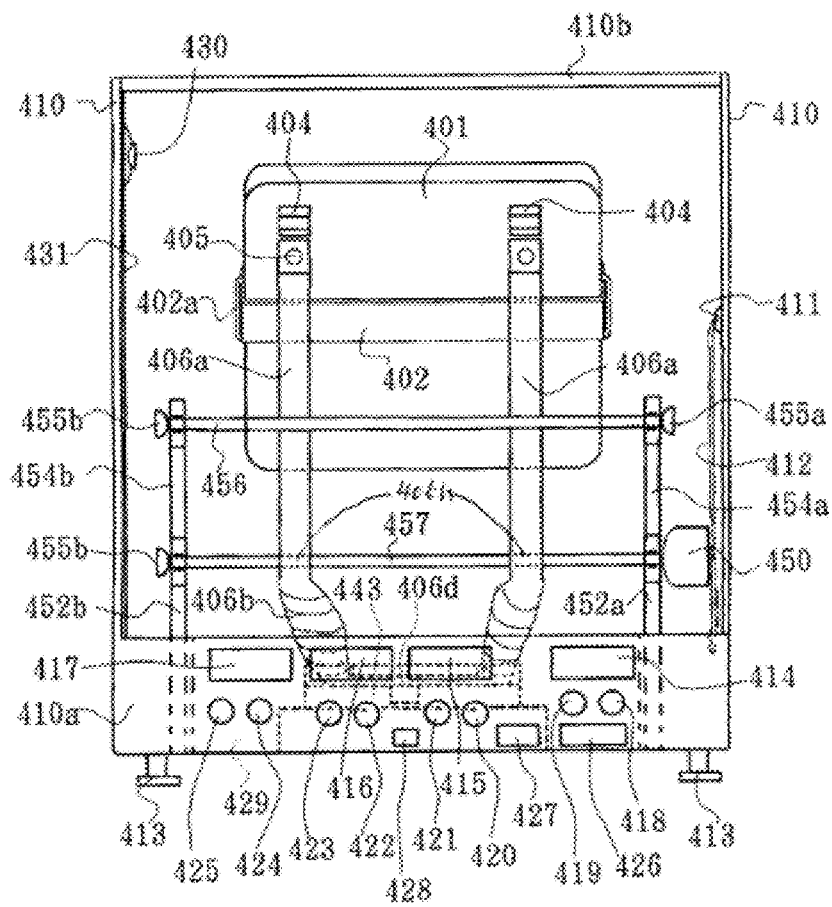
FIG. 17 is the front view of a physical function training device of Example 4.
Figure 21:
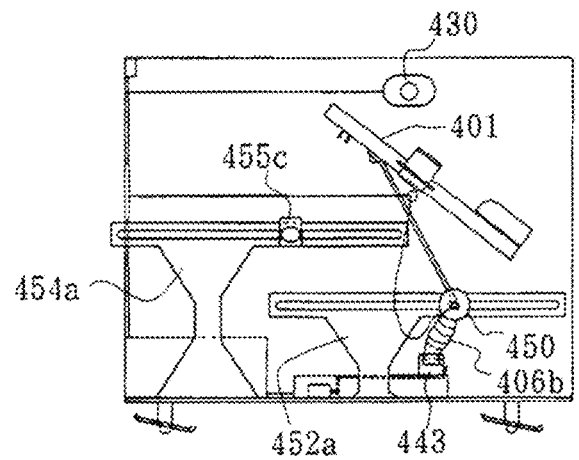
FIG. 21 is an explanation drawing of Example 4, (a) is a drawing of the maximum upper limit at the time of rocking in the vertical direction, (b) is a drawing of the bottom minimum limit at the time of rocking in the vertical direction and (c) is a drawing at the time of a reciprocating motion in the direction of order.
Figure 21:
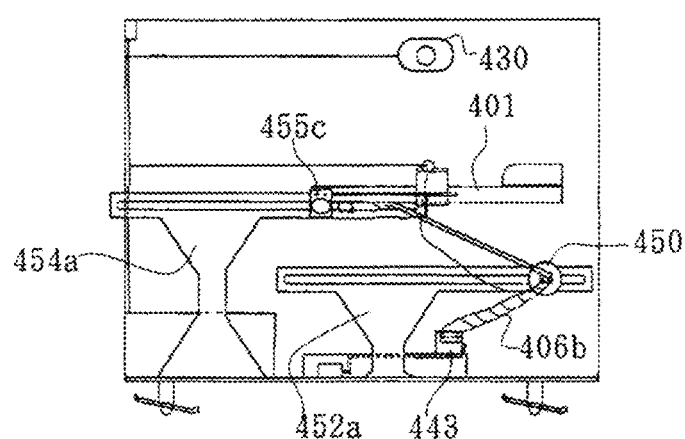
Figure 21:
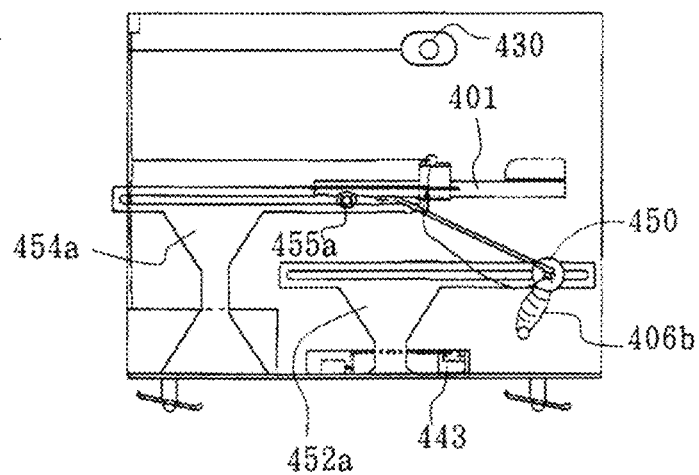

I explain Example 4 of a physical function training device in this invention by using FIG. 17 or FIG. 21.

FIG. 17 is the front view of a physical function training device of Example 4.

Figure 18:
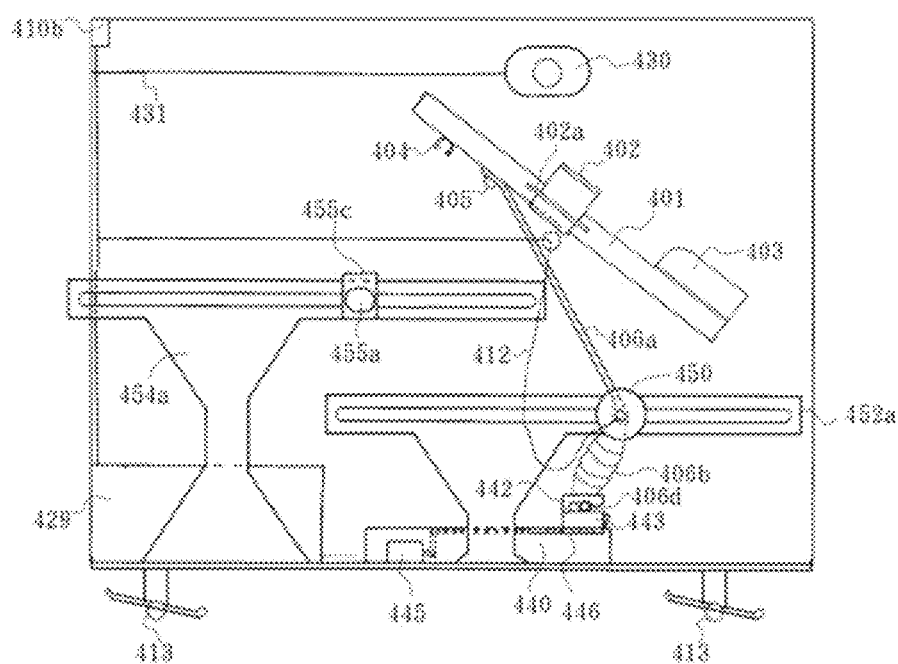
FIG. 18 is a side view of a physical function training device of Example 4.

FIG. 18 is a side view of a physical function training device of Example 4.

Figure 19:
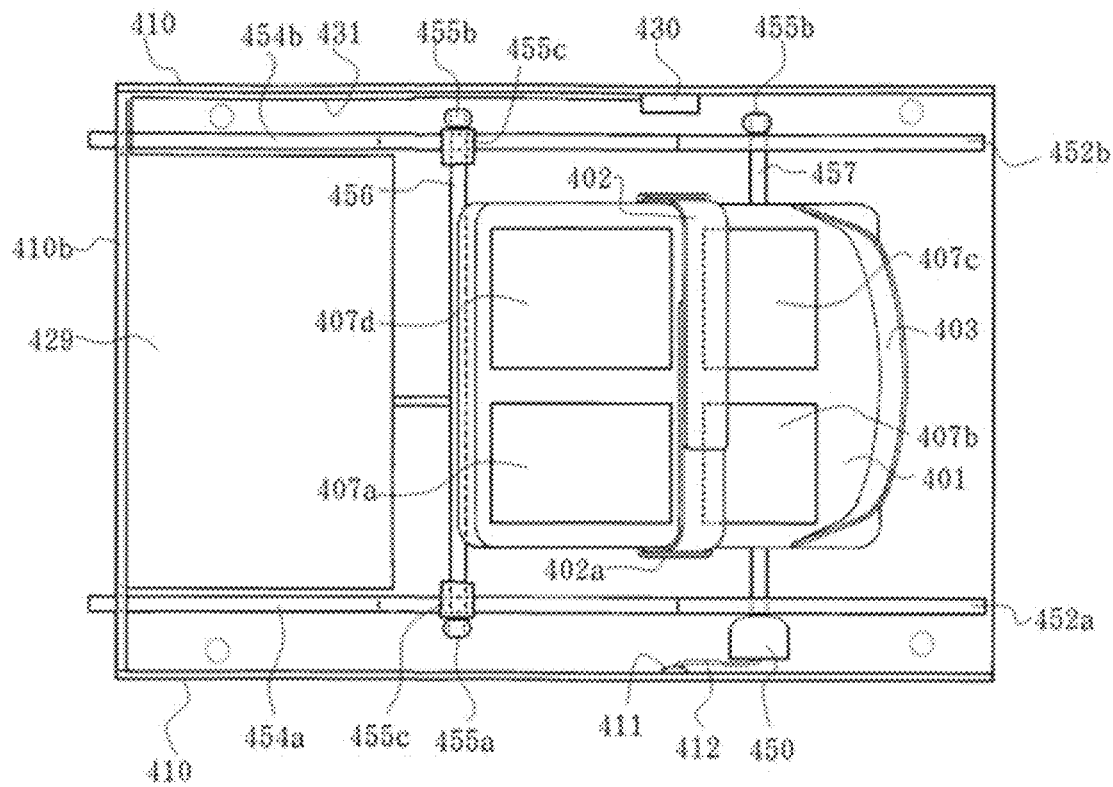
FIG. 19 is a plain view of a physical function training device of Example 4.

FIG. 19 is a plain view of a physical function training device of Example 4.

Figure 20:
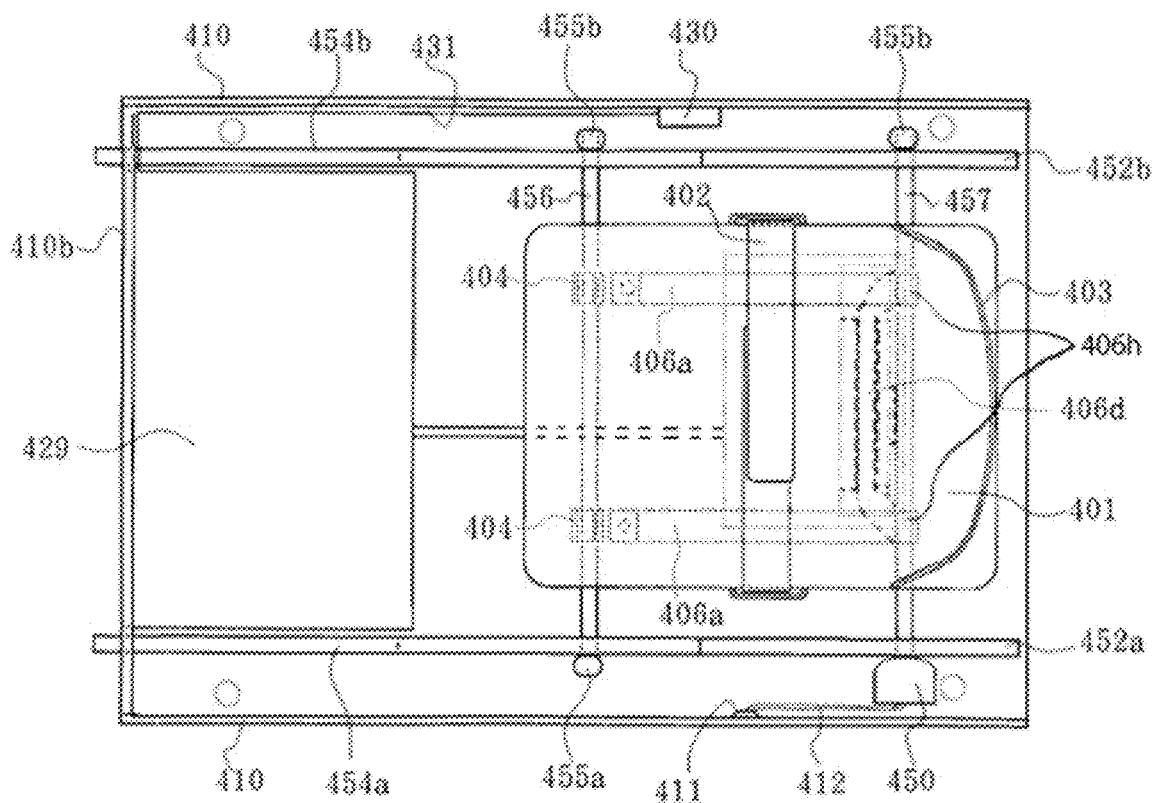
FIG. 20 is a plain view of the usage state of the back and forth direction movement of Example 4.

FIG. 20 is a plain view in the usage state of the reciprocating movement, front and back, of Example 4. Furthermore, the contact sensor has been omitted in FIG. 20.

FIG. 21 is an explanation drawing of the 4th embodiment, (a) is a Figure of the upper maximum limit at the time of rocking in the vertical direction, (b) is a Figure of the bottom minimum limit at the time of rocking in the vertical direction and (c) is a Figure at the time of a reciprocating motion in the direction of order.

A training board (401) is formed of wood with a plane similar to a rectangle (or by any necessity, such as plastic).

A training board (401) is similar to a training board of Example 1 or Example 3.

It has an area of sufficient width that both feet can be set upon (for example, the size of the side about 20 cm and about 25 cm, length, the size of the side about 20 cm and about 35 cm, width).

Therefore, a disabled person can set both of a foot with disability, which has hemiparesis of lower extremities of a nerve, decline of the lower limbs extremities muscular strength that originates from a plasmotomy of Achilles' tendon of any of lower extremities, a disability of a range of motion, etc. of an ankle, and also a knee of any bone fracture, etc. and a foot of the other healthy foot without any disability in the condition of sitting on a chair.

In the case of both hands, a user sits on a chair and moves device with both hands placing a device on a desk.

A disabled person can set both feet in the condition of sitting on a chair; a foot with disability, which has a decreased upper arm muscle strength due to upper arm nerve palsy and tear of upper arm muscles, a disability of a range of motion, etc. of an ankle (ankle or wrist) (ro), and also a knee (knee or elbow) (i) of any bone fracture etc. and a foot of the other healthy foot without any disability.

A heel support part (403), which is formed by belt-like things, such as plastic, skin, and cloth, is similar to the heel support parts of Example 1 to Example 3.

It is almost shaped like a letter C shown in a plain view and then is fixed with tack wear, nail wear, screws etc. to an upper part of a rear surface of a training board (401) and impedes a movement to the rear of both heels, in the case that both feet are kept on the surface of a training board (401).

Furthermore, in the case that heel support part (403) is formed from plastic, it may form a unit to a training board (401).

And also, a setting band (402) that the edge part of the right and left adhered to a training board (401) is set up both with the interval from this heel (heel or wrist) support part (403) to the front and almost to the central position of the long hand direction of a training board (401).

A setting band (402) sets through an undersurface of a training board (401), both end parts which pass conducive brackets (402a), which is a plane Japanese letter (KO) character form, respectively, and which assemble in a right and left aspect of a training board (401) of each and are keeping upward of a training board (401).

And both right and left end parts of band setting band (402) are overlapped mutually and are engaged by a proper engaging means such as a velvet fastener, snapshot, hook, etc. easily.

However, the setting band (402) is composed of one setting band, it is available to be assembled of two setting bands, end parts of which are fixed in a training board (401).

The setting band (402), which covers insteps of both feet (hands or feet) from an upper side, is impeding the movement to both feet from the upper and front side.

Securing tools (402. 403) that hold both feet (feet or hands) in a training board (401) are composed of the heel (heel or wrist) support part (403) and the setting band (402).

The structure, material, etc. of securing tools (402. 403) are possible to change suitably if both feet (feet or hands) can be kept and set on a training board (401).

As well, at the condition that a patient recovered and each power can be put into both feet (feet or hands), the securing tools to both legs may be unnecessary.

A training board support part (406a) is composed to each of right and left side to the front lower part of a training board (401) by training board support security screws (405).

A hole (406h) of a cross-sectional similar round shape perforates and is formed to the lower end part of a training board support part (406a).

Rotation is available with a rear support axis (457), which is arranged in the direction of order horizontally to the hole (406h) and is inserted.

Therefore a training board support part (406a) can rock to a rear support axis (457), and on the other hand, a rear support axis (457) can rotate to a training board support part (406a).

Also, a load device (406b), which consists of a haul spring, etc., assembles a lower end part of a training board support part (406a) and the load device (406b) forces in the direction where the front of a training board support part (406a) pops up.

And a rear support axis (457) assembles in the long holes, which assemble both axes supporting structures (452a, 452b) of right and left, as a slide part, with rotation and sliding possible.

And a rear support axis (457) is held by screwing a hold axis clasp (455b) on one edge to stop it from coming out with an accelerometer (450) at the other edge.

Long holes of axis supporting structures (452a, 452b) are assembled parallel to the base of a physical function training device.

Hereafter a rear support axis (457) can rotate and slide in a back and forth direction and also becomes a pivot axis in the case that both training board (401) and a training board support part (406a) rock.

Patient sets feet on a training board (401), presses it downward with forced resistance of a load device (406b), decreases a downward power to the training board (401) and moves a training board (401) up with forces from load device (406b).

Then, the patient presses it downward with forced resistance of a load device (406b).

Thus, rocking in the vertical direction is repeated.

Also, a rear support axis (457) moves in a reciprocating motion in a back and forth direction from the position of the foreside as shown in FIG. 19 to the rear position as shown in FIG. 20 when a training board (401) rocks in a vertical direction.

An accelerometer (450) detects an acceleration of a reciprocating movement in a back and forth direction of a rear support axis (457) about one direction (forward direction or backward direction).

The detected acceleration is transmitted to a control unit (429), which consists of a microcomputer, through an information transmission route (412).

A control unit (429) counts and generates numbers of reciprocating motion of a training board (401), whenever the signal of acceleration is inputted from an accelerometer (450).

And a control unit (429) memorizes an acceleration input from an accelerometer (450) and the number of reciprocating motion of a training board (401) in a storage unit as data and outputs it suitably if needed.

And it does not use the acceleration but can also use speed and the number of new speed occurrences by detecting one-directional speed.

Also, an axis hold part (404), which engages a clutch freely to a foreside support axis (456) assembles at the front of a training board support part (406a) to a front lower part of a training board (401).

A foreside axis hold part (404) is a structure, which can keep a foreside support axis (456) rotating freely; structure bears a load of a training board (401) having and can secure a training board (401) horizontally.

In Example 4 a structure can also secure a foreside axis hold part (404) with a pin, wire, etc. after a foreside support axis (456) fits in, but also any kind of structure is good that can bear a load and can secure horizontally.

Each of four sheets of contact sensors (407a, 407b, 407c, 407d) assembles vertically and horizontally to the upper surface of a training board (401), and these contact sensors (407a, 407b, 407c, 407d) detect when anything contacts it and outputs a detection signal.

Although a training board (401) assembles upward with the angle of about 40 degrees and upward. 37.5 degrees in Example 4, healthy feet, which are set, contact sensors simultaneously.

However, feet with contracture cannot contact simultaneously.

With a contact of the foot tip and heel of the foot with contracture is detected, changes in the angle of a training board (401) as degree of horizontality by contact sensor (407a, 407b, 407c, 407d), data is transmitted through information transmission route (412), such as an electric wire.

By our research, it was confirmed that the movement of a training board (401) in a back and forth direction and a vertical direction begins an ankle plantar Flexion of 37 degrees and makes a knee flexion of 118 degrees possible.

Thereby, it can evaluate the angle of the joint of motion of a patient who has contracture due to motivative exercise by a patient's self or a passive exercise by a caregiver.

The exterior of Example 4 is a unit structure and consists of transparent plastic.

The front and the rear surface is an open space so that prevention of exercise may not be carried out.

A front lower part (410a) is opaquely painted to assemble a switch part.

A communication-information stability assembly device (411) assembles as an information transmission route (412) and is composed steadily on the right side of an aspect part (410).

A camera (430) and an information transmission route (431) assembled in the left aspect part.

An antenna (410b), which inputs and outputs information assembles to the front upper part, and since this antenna (410b) has connected both aspect parts (410) at the upward and foreside mutually it achieves the purpose to strengthens a structure.

A caster (413) with sled assembles in four corners in the lower part of the base, respectively.

An information transmission route (412) is composed of an electric wire and transmits a signal that is detected with an accelerometer (450), which moves in a back and forth direction.

An information transmission route (412) may be composed of a radio signal that can be transmitted.

A camera (430) formed in the left side is an artificial retina camera, and while it takes a photograph of a large domain simultaneously, it can detect photography data continuously.

This shooting data is input to a control unit (429) through an information transmission route (431) and a control unit (429) and can output this shooting data as it is or is processed.

While output is made to display units (414,415,416,417 etc.), it can perform an external output from an external information output terminal (427) and an antenna (410b).

Although a camera (430) is an artificial retina camera in Example 4, any camera is good that can detect shooting data continuously and shoot the wide range simultaneously as a CCD camera and a video camera, etc.

A control unit may be arranged anywhere.

The contact sensors 407a, 407b, 407c, 407d detect contact simultaneously, and this detection signal is input to a control unit (429), then control unit (429) outputs a drive signal in camera (430) of a left side aspect part.

A camera (430) shoots when it receives a drive signal and output shooting data to control unit (429).

Since an artificial retina camera is used in Example 4 it can recognize easily the outside of the object taking a photograph, it can process and output the angle of a training board (401), which took a photograph and the angle of the joint of a patient's lower extremities as angle data in control unit (429).

In the case that these angles, etc. are detected in Example 4, a caregiver moves a training board (401) manually.

A control unit (429) assembles in the front lower part of the exterior in which it was painted.

In the front lower part of the exterior, in which control unit (429) is composed, a number indicator display unit (414), an angle indicator display unit (415), an acceleration indicator display unit (416), an exercise kind display unit (417), a motion times setting switch (418), a reset switch (419), an angle investigation switch (420), an angle manual change switch (421), an acceleration setting switch (422), an exercise selection switch (423), a manual camera shutter switch (424), a power-supply switch (425), an external information output terminal (427) and an external information input terminal (428) are assembled.

A control unit (429) performs control.

A number indicator display unit (414), an angle indicator display unit (415), an acceleration indicator display unit (416) and an exercise kind display unit (417) or any display is good, such as a data display rotating drum, if data can be displayed, although they use digital display equipment.

A control unit (429) uses a microcomputer.

All the devices are tied with an information transmission route.

A foreside support axis (456) assembles in the long holes, which assemble both axes supporting structures (454a, 454b) of the right and left side, as a slide part that rotates and can slide.

The foreside support axis (456) is held down by screws with hold axis clasps (455a, 455b).

Long holes of axis supporting structures (454a, 454b) are parallel to the base of a physical function training device.

Also, a foreside support axis (456) is fixed with a motionlessness help device (455c) to halt stability in the optional place of a long hole and can halt it.

As shown in FIG. 21(*b*), a foreside support axis (456) touches and impedes descent of a training board (401) if a training board (401) drops to a minimum descent so that a training board (401) does not travel below the lowest end of a training board (401) and rocks in the vertical direction.

A foreside support axis (456) is fixed with a motionlessness help device (455c) and halts.

As shown in FIG. 21(*b*), a halted foreside support axis (456) works as a hold axis to halt, which supports the front of a training board (401) at the position other than hold axis clasps (455a, 455b), in other words the position which does not become obstructive to axis hold part (404).

When a training board (401) exercises the back and forth direction of order, in order to be able to exercise in a movement of a training board (401) with the installation side of lower extremities function training device nearly parallel, as shown in FIG. 20 and FIG. 21(*b*), a training board (401), of which the front part is supported with a foreside support axis (456) and the rear part is supported with another rear support axis (457), slides in the back and forth direction of order almost parallel with the foreside support axis (456) and the rear support axis (457) rotates.

Thus, a parallel movement exercise can be carried out with a patient's motivative exercise.

In the case of this reciprocating movement in a back and forth direction, a hook (442) keeps a connection part material (406d) free, and a load of a load device (406b) does not load.

(However, it is possible to add a load by other means, for example, a load device such as spring is attached freely and separately.)

It is possible to assemble a linear-drive motor in axis supporting structures (454a, 454b), to give a magnetic field to a rear support axis (457), to drive the linear-drive motor of a rear support axis (457) and also to make a training board (401) drive forward and backward.

Moreover, it is also possible to assemble a motor as a drive unit, which makes a training board support part (406a) rock to a rear support axis (457).

In such a case, a load device (406b) is omissible.

By carrying out load to a rear support axis (457) with the linear motor, it can apply load to the back and forth direction movement of a training board (401).

In addition, it is also possible to compose a load device, such as a spring, separately in a back and forth direction movement of a training board (401).

It is possible to apply a load of a rock in the vertical direction of a training board (401), by applying a load of a rock of a training board support part (406a) with a motor.

It is possible to use it as a training machine for a resistive exercise due to applying a load to a rear support axis (457) by a self-propelled mechanical movement of a rear support axis (457) or a self-propelled electrical movement by using a motor, etc., even without a linear motor.

Moreover, in the case of rocking in the vertical direction, it is necessary for a motivative exercise that a training board (401) needs to attach almost 37 degrees upwards, top direction toward foot tip (Foot tip or fingertip) part from the heel part (heel or wrist), the realization can be attempted even when there is not a load device (406b).

Although the load function is given to a rear support axis (457) in Example 4, the load function of the direction of order can also be given and controlled on a foreside support axis (456).

In the case that a training board (401) moves in the back and forth direction, although, the height of a rear support axis (457), which locates the lower part of a load device and a foreside support axis (456), which is positioned in different heights, locates the upper part to carry out parallel movement.

A training board support part (406a) may be made of a material such as plastic, etc., that can support loads, although, it is the one unit structure made from steel in Example 4. Separate structures are sufficient as structure.

Although a load device (406b) uses a spring of steel if a load can be applied to maintenance axes (456,457), it does not need to be a spring.

Anything is sufficient if applied as a load such as oil pressure, air pressure, etc., in the case of separate structures.

Nothing else is needed when using the linear motor, etc.

The lower end part of load devices (406b) of both right and left sides are connected with a connection part material (406d) mutually and this connection part material (406d) is attached with an up-down system (443) freely by an electromotive hook (442).

Therefore, the loading power of a load device (406b) can be certainly applied to a training board support part (406a).

A drive mechanism (440) that drives an up-down system (443) assembles in the bottom of the exterior of a physical function training device.

A drive mechanism (440) consists of a motor (445) as a drive unit and a power transmission device (446).

A power transmission device (446) consists of a combination gear mechanism.

This power transmission device (446) is for making an up-down system (443) make vertical movements and may use power transmission mechanisms, such as a chain and a belt, and may make an up-down system (443) make vertical movements by oil pressure, air pressure, etc.

At the time of a connection part material (406d) is assembled to an up-down system (443), a caregiver operates hooks (442) on the right and left sides manually and holds down both side parts of a connection part material (406d).

As shown in FIG. 20, a training board (401) is held freely to move in the space between axis supporting structures (454a, 454b) and axis supporting structures (452a, 452b) by a foreside support axis (456), a rear support axis (457) and a training board support part (406a).

As Example 1 and Example 3, when a training board (401) moves in a back and forth direction, in consideration of its small movement right and left, due to the strength of the foot (hand or foot) of a healthy side being stronger than the strength of the foot (hand or foot) of a disabled side, the movement width of about 10 cm right and left is set.

Therefore, not giving ache is important for a motivative exercise, and a corrective exercise is eased off the fixed direction moving.

However, a resistive exercise and a corrective exercise are also important, it is possible to do a resistive exercise and a corrective exercise in the cross and vertical direction due to carrying out a load to a rear support axis (457) by a manual operation, linear motor, a mechanical self-propelled movement or an electrical self-propelled movement by use of a motor of a rear support axis (457).

Also in Example 4, although the volume of exercises was set up according to a patient's condition, the number of times, acceleration or speed is detected and used by using an accelerometer so that a movement is not possible when the set volume of exercises is ended.

First of all, it detects with an accelerometer (450), the number of times is counted in increments of 1 when acceleration newly occurs, and it sequentially counts the volume of exercises by carrying out sequential calculations of the number of times.

In order to set up the number of times of movement, it sets up with a motion times setting switch (418).

It is a structure that is not able to release if a reset switch (419) is used after completion.

The number of times may be set to about 300 times.

You may increase the number of times for a resistive exercise.

In this case, even tens of thousands of times can be set up.

Furthermore, if the function of a control unit (429) using a microcomputer, it is also possible to be set up for time usage.

In the case of control by using acceleration, either acceleration or speed can be used as a measurement value, it is the same as that of Example 1 in the case of speed.

In the case of using acceleration, the volume of exercises with the fine displacement is prescribed by making 0 since 10 G grade into the measurement range.

Also, in this case, it is set up with an acceleration setting switch (422), and the cycle is enabled again with the reset switch (419).

In this embodiment, a drive mechanism (440) and a hook (442) are used in order to stop an exercise When vertical movement is chosen with an exercise selection switch (423), the condition where a training board (401) carries out vertical movement is shown by FIG. 21 (a) and FIG. 21(b).

If the position of a rear support axis (457) moves to FIG. 21 (b) from FIG. 21 (a), a load device (406b), the upper-end part of which expands and contracts by sliding to the long holes of axis supporting structures (452a, 452b), applies a load.

A load device (406b) is prolonged, as shown in FIG. 21 (b); it always has shrinkage pressure and makes a motivative exercise possible by the return power of a load device (406b).

When detection data reaches the fixed number of times or the fixed acceleration and speed which were set up, a connection part material (406d) is released due to a cancellation command and is set up from a control unit (429) in an electromotive hook (442), and then a hook (442) operates.

When a connection part material (406d) is free the return power of a connection part material (406d) disappears, and it becomes the condition that a training board (401) fell to the lower limit without returning upward.

Moreover, a foreside support axis (456) that is fixed with a motionlessness help device (455c) becomes obstructive, and a back and forth direction movement cannot be performed.

Namely, it becomes the condition that a brake worked.

Thus, by releasing a connection part material (406d), a hook (442) has applied brakes to rocking and has the function of a brake.

In addition, it is also possible to adopt brake mechanisms other than a hook (442).

Figure 22:
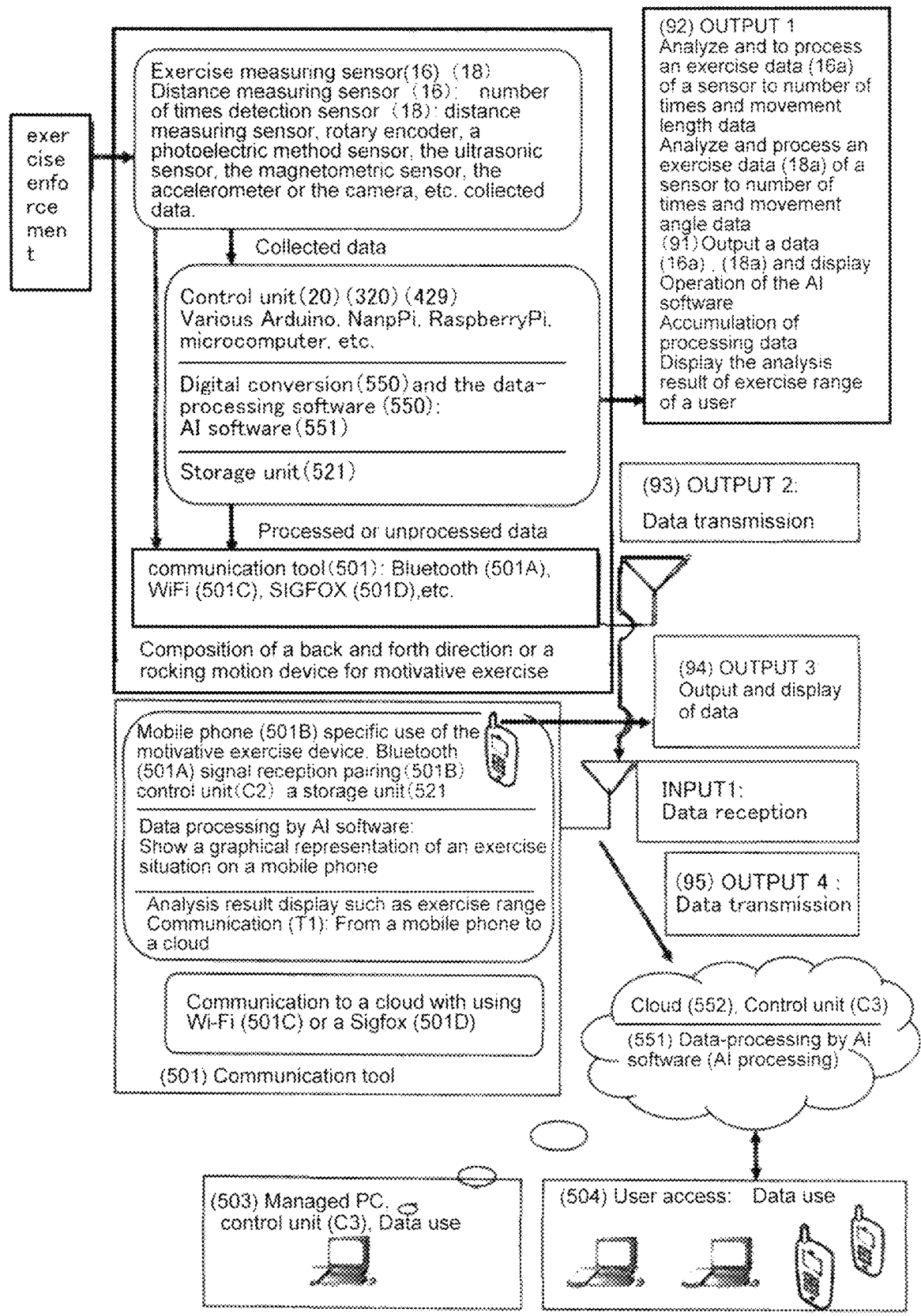
FIG. 22 is a conceptual diagram of the composition and the function of this invention.

When a back and forth direction movement is chosen with an exercise selection switch (423), the condition where a training board (401) carries out a back and forth direction movement is shown by FIG. 22 (c).

A hook (442) is canceled, and the lower end of a connection part material (406d) is free.

Therefore, a load device (406b), which is a shrunk structure, moves back and forth direction for the overall length of the long hole that was opened to an axis supporting structure (452a) with a back and forth direction exercise.

A back and forth direction movement is requested almost 40 cm in length and a long hole, which has been opened to an axis supporting structure (452a) is able to materialize the movement.

When detection data reaches the fixed number of times or the fixed acceleration and speed, which were set up at this time, the command that raises an up-down system (443) comes from a control unit (429) to a motor (445) of a drive mechanism (440).

When an up-down system (443) rises by a command, it becomes hard to move in a back and forth direction because an up-down system (443) becomes obstructive for the back and forth direction movement of a load device (406b).

In other words, brake works.

Thus, an up-down system (443) has the function of a brake.

In addition, it is also possible to adopt brake mechanisms other than an up-down system (443).

Thus, the time of making a training board (401) rock in the vertical direction, a hook (442) engages a connection part material (406*d*) and the time of making a training board (401) move in the back and forth direction with reciprocating motion, a hook (442) releases a connection part material (406*d*).

Moreover, the time of making a training board (401) rock in the vertical direction and stop the reciprocating movement in the back and forth direction, an up-down system (443) has gone up and the time of making a training board (401) move in the back and forth direction with reciprocating motion and an up-down system (443) has descended.

In addition, The control unit (429) is a control unit similar to the control unit (20) of the embodiment 1.

Because the physical function training device according to Example 4 of the present invention is configured in this manner, it is effective in order to do motivative exercise in the sitting position with both feet, one foot with a disability in the case that there is hemiparesis after apoplexy, a decline of muscular strength of the lower extremities is caused by the rupture of the Achilles' tendon and/or disabilities of the range of motion in ankle originating in a bone fracture of the disabled lower extremities for example, and another one foot with healthy foot without any disability.

It is an effective training device that realizes both reciprocations in back and forth direction and vertical rocking motion.

The operation of the control unit of the invention and the operation of artificial intelligence/machine learning (from now on referred to as AI software) will be described in detail concerning FIG. 28 from FIG. 22.

FIG. 22 is a conceptual diagram showing composition and a function of the present invention.

Figure 23:
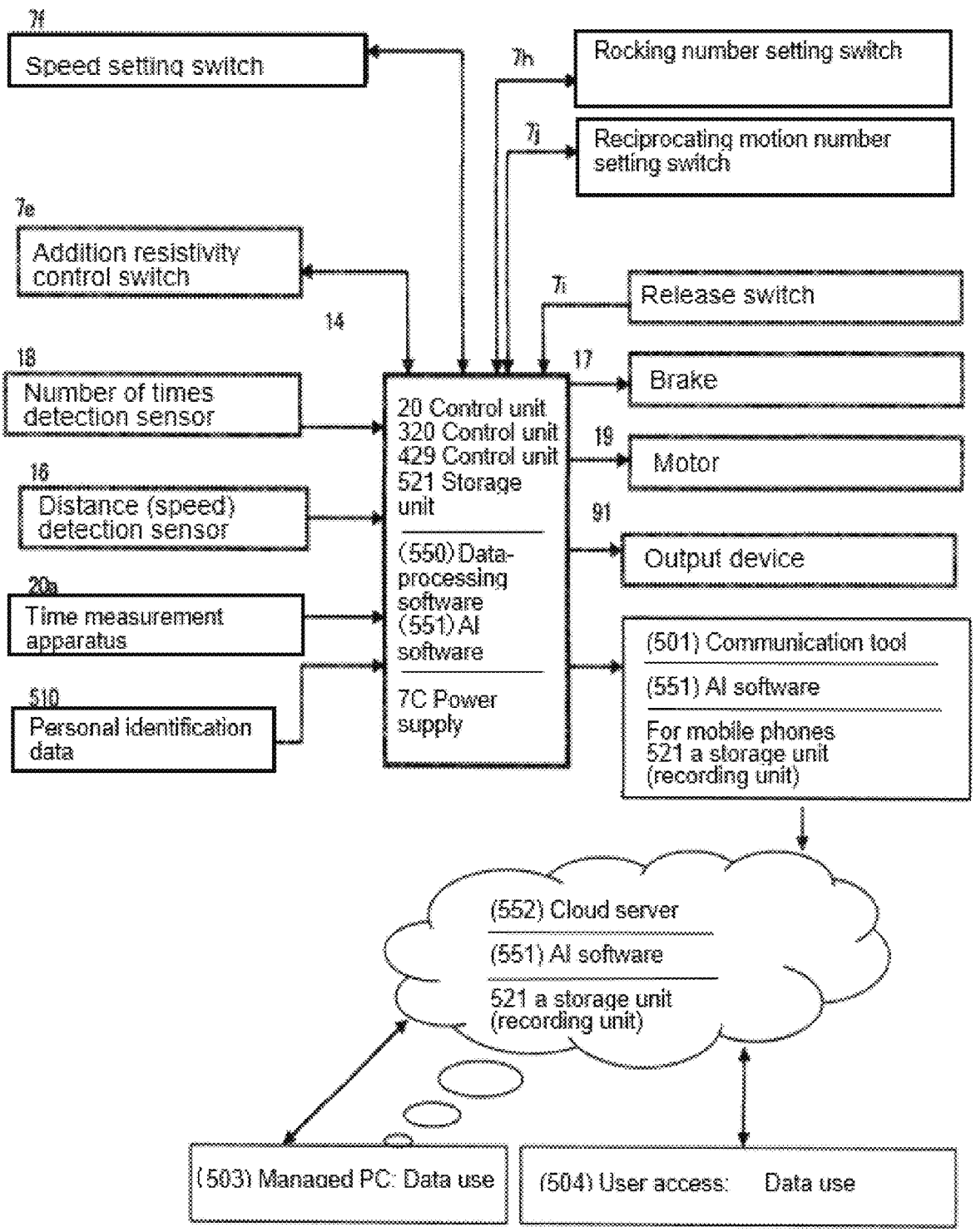
FIG. 23 is a control circuit diagram of Example 1.

FIG. 23 is a control circuit diagram of Example 1.

Figure 24:
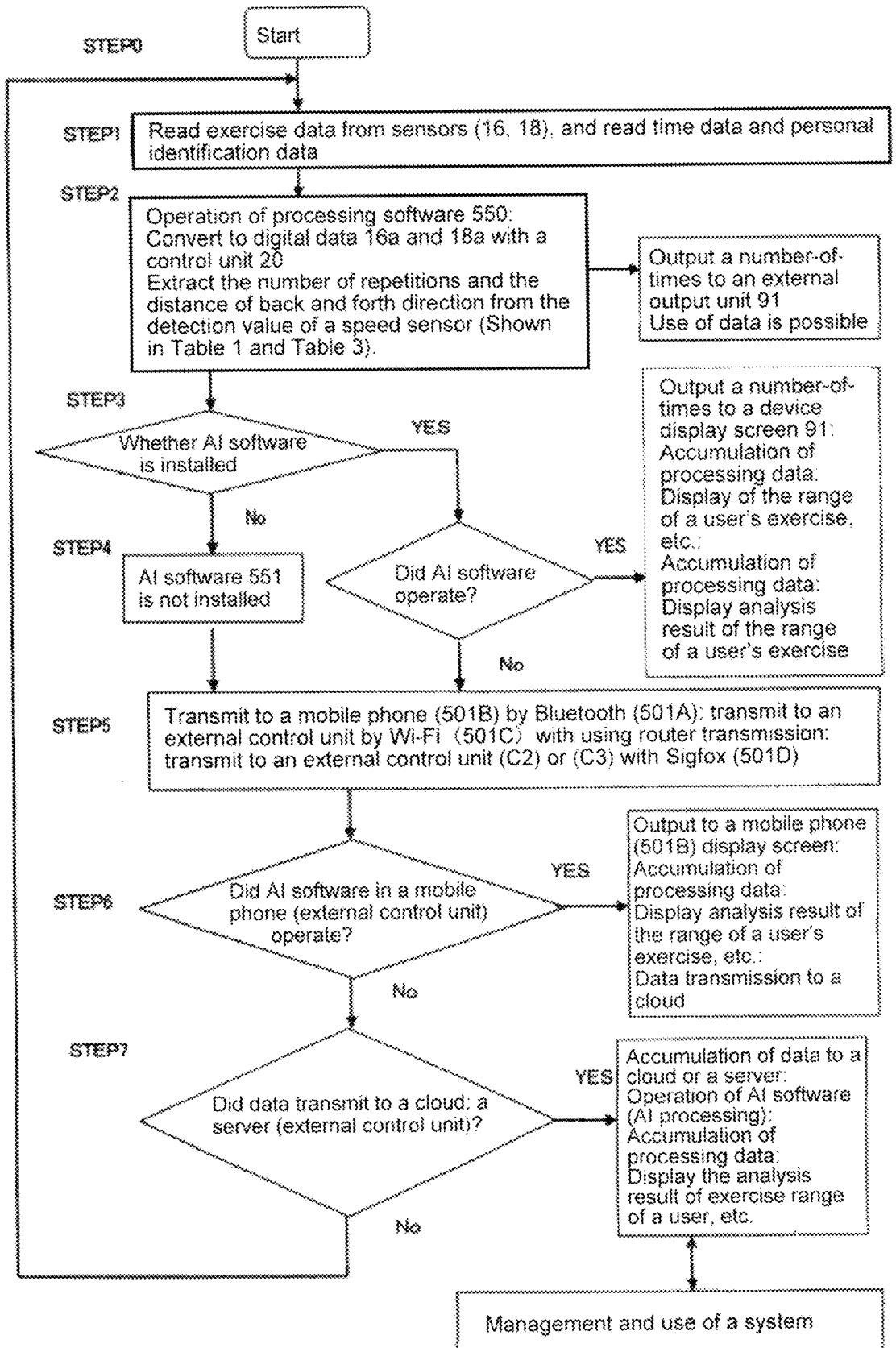
FIG. 24 is a flowchart in case, which focuses on a radio communications system

FIG. 24 is a flowchart in case, which focuses on a radio communications system

Figure 25:
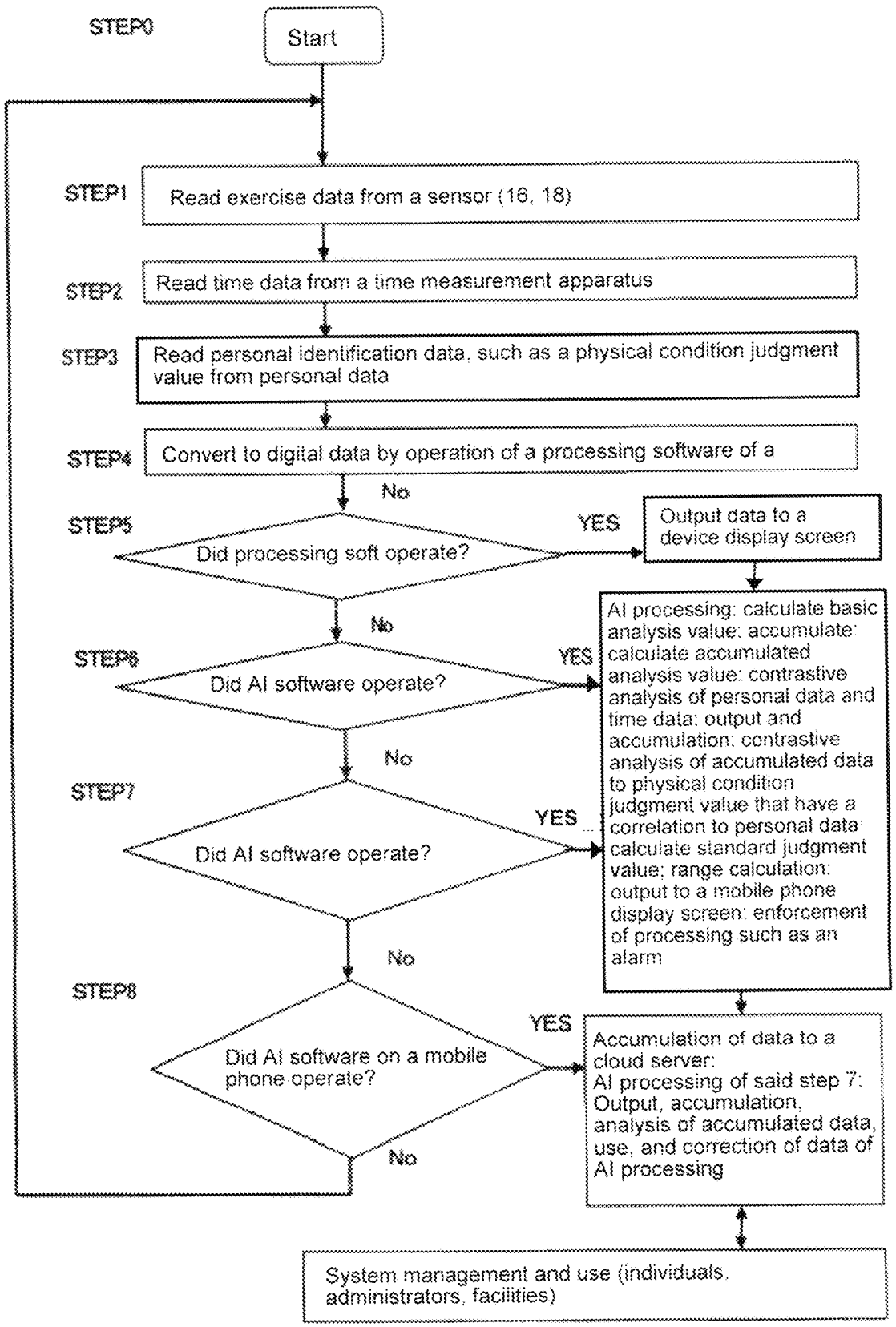
FIG. 25 is a flowchart in case, which focuses on the processing of an AI software.

FIG. 25 is a flowchart in case, which focuses on the processing of an AI software.

Figure 26:
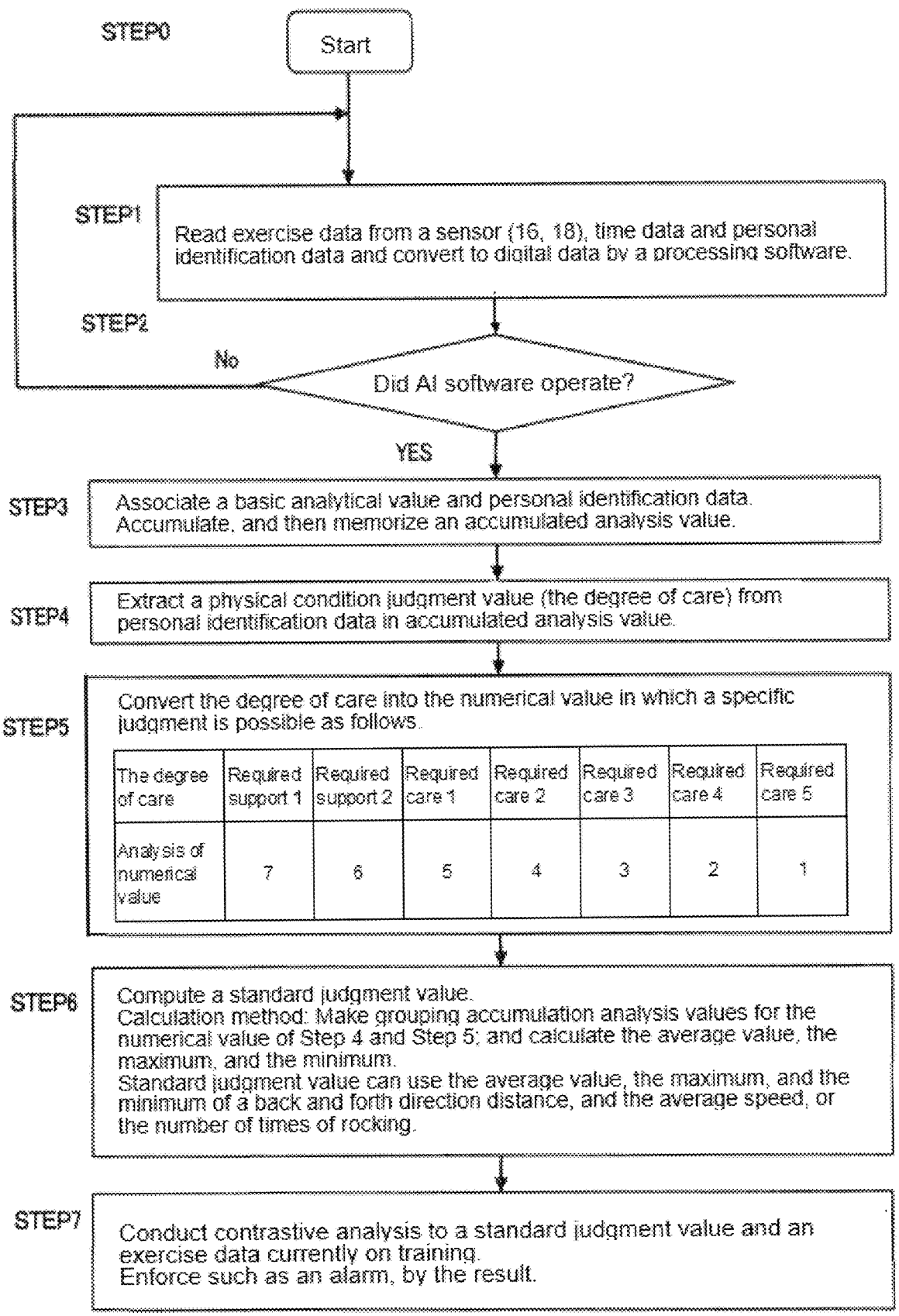
FIG. 26 is a flowchart in case, which AI software search standard judgment value.

FIG. 26 is a flowchart focused on cases, which AI software processes standard judgment value, accumulated analysis value, and standard judgment value, respectively.

Figure 27:
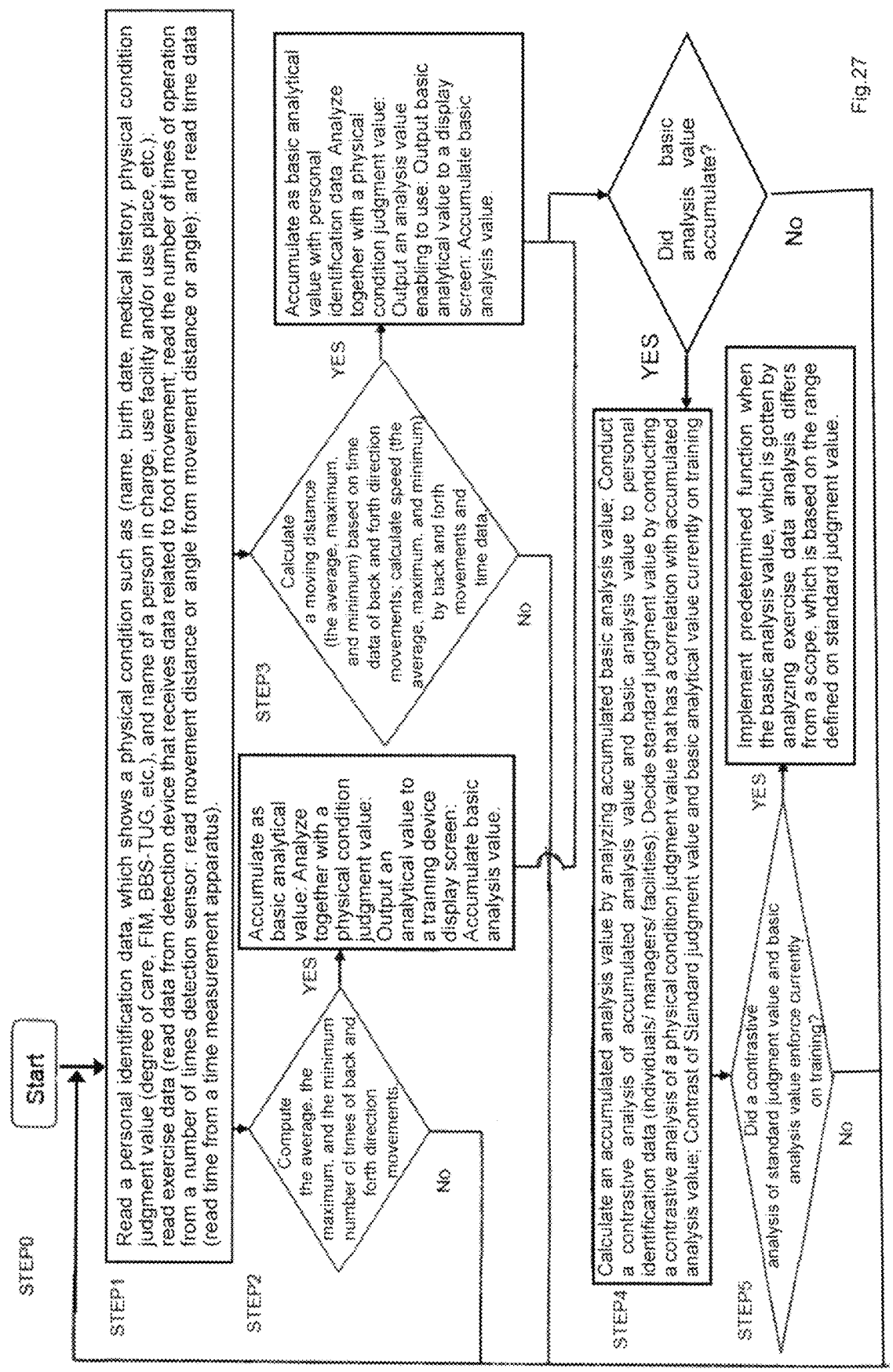
FIG. 27 is a flowchart in case, which focuses on the processing of a back and forth direction movement exercise data.

FIG. 27 is a flowchart in case, which focuses on the processing of a back and forth direction movement exercise data.

Figure 28:
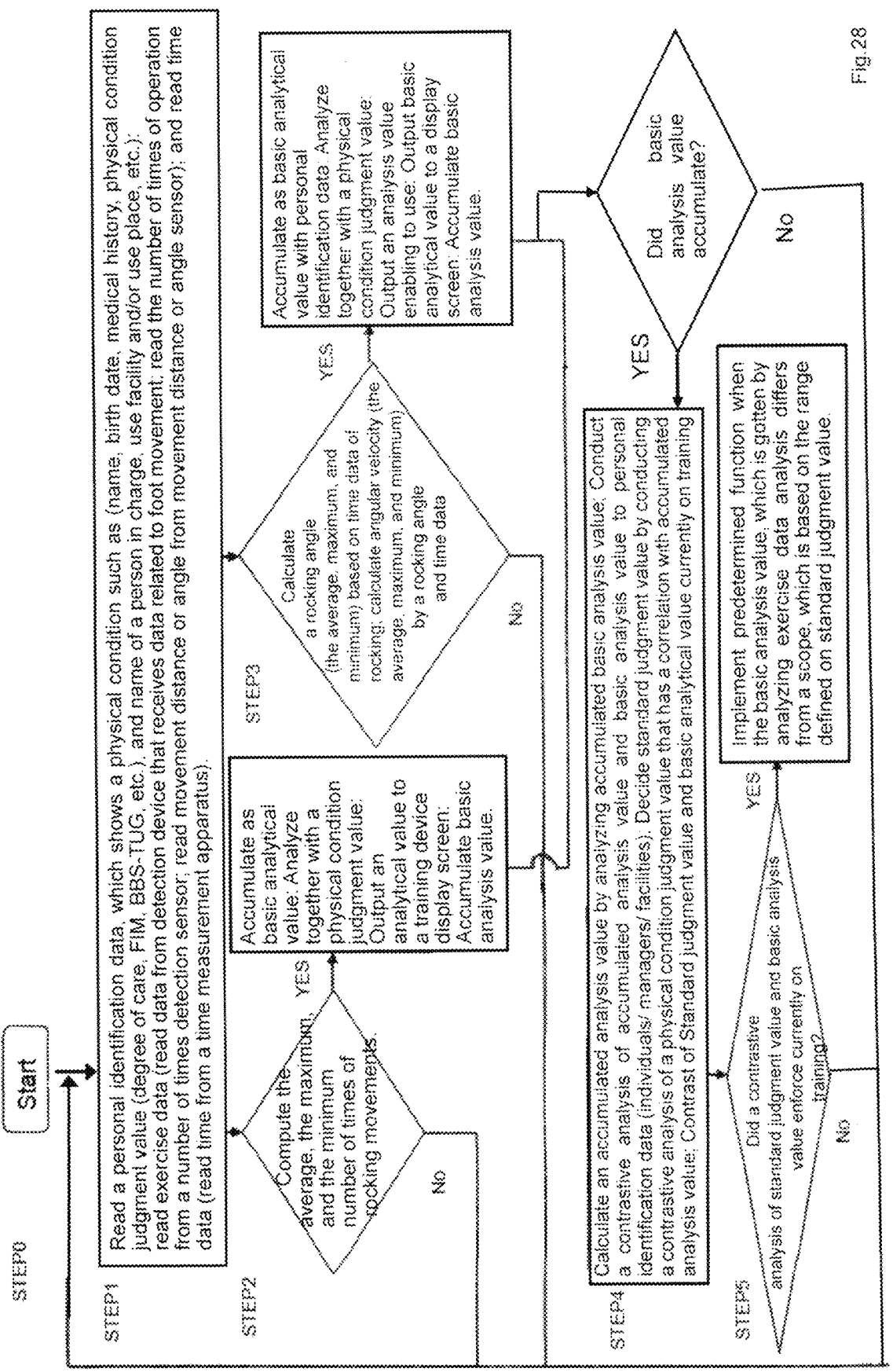
FIG. 28 is a flowchart in case, which focuses on the processing of rocking exercise data.

FIG. 28 is a flowchart in case, which focuses on the processing of a rocking exercise data.

I explain FIG. 22 and FIG. 23.

The control unit 20 that is composed as a Detection device for data related to a motion of upper or lower limbs, which is composed of a distance detection sensor (16) and a number-of-times sensor (18) and storage unit (521) that is included in the control unit 20.

And control unit 20, which enables analyzing exercise data received by a detection device is composed of Various Arduino, NanpPi, RaspberryPi, microcomputer, etc.

The storage unit (521), which is included the control unit (20) records personal identification data, exercise data collected, collected time data of the exercise data at the time of enforcement from a time measurement apparatus (20*a*).

This invention is characterized by collecting data of the current motivative exercise device (9), namely the motivative exercise device of the U.S. Pat. No. 5,238,917 shown in FIG. 29 and AI software (551), which automatically collects the processed result data shown in Table 3 is installed on a mobile phone (501*b*) and cloud (552).

The mobile phone 501*b* uses the usual SIMM free mobile phone.

Cloud (552) uses google drive.

Cloud (502) is managed by managing PC (503).

Any cloud is suitable for use not only in google drive.

A server in person may place and can also use it as a cloud.

A cloud (502) is attained to use by many users (504) who use from PC or a mobile phone.

Digital conversion and the data-processing software (550) is usually used, and it is not mentioned specially.

The result is extracted, and it may be arranged by the other arbitrary PCs, as shown in the table mentioned above 1 and Table 3.

The control unit (20) is equipped with digital conversion and the data-processing software (550).

A data-processing software (550) converts the exercise data obtained from the detection device for data concerning the exercise of the upper or lower limbs into processable digital data.

It is changed into the data in which enables to process as shown in Table 1 and Table 3.

Detection device for data related to an exercise of upper or lower limbs may be any other sensor capable of appropriate detection such as distance measuring sensor, rotary encoder, photoelectric sensor, ultrasonic sensor, magnetic sensor, acceleration sensor, or a camera.

In Example 1 and Example 3, a rotary encoder is used as a detection device for detecting data of exercise.

By analyzing the output of the rotary encoder, the speed, the number of times, the rotation, and the distance are measured.

a distance detection sensor (16) and a number-of-times sensor (18) can be merged with to one sensor for detection device regarding the exercise data by using the data-processing software (550) when the rotary encoder is used.

In addition, The speed detection sensor detects the distance and obtains speed data in combination with time measurement means.

The control unit (20) may be equipped with AI software (551).

In Example 1 to Example 4, the control unit (20) equips AI software (551).

As shown in Table 1 or Table 3, the control unit (20) makes the storage unit (521) memorize personal identification data (510) such as the name, birth date, value (degree of care and FIM (Function Independence Measure), various walking evaluation methods such as BBS-TUG (Berg Balance Scale, BBS TUG 10 m walking test), etc. name of the person in charge and a facility or place of use.

This personal identification data (510) may be input using a keyboard of a connected PC, which is not displayed, and transfers and uses data created by the mobile phone (501B) or a cloud (552).

Moreover, when using the AI software in a mobile phone (501B) or a cloud (552), it is possible to use data of a control unit (C2) of the mobile phone (501B) or a storage unit (521) of a control unit (C3) of a cloud (552).

A time measurement means 20*a* is included by the control unit (20) as common sense.

Moreover, it may also be possible to use the time data on the Internet by using a communication tool.

An external output device (91) is a display unit (327) of Example 3 or a display unit (414) of Example 4, and also it can be a ringing device.

Moreover, a display may be composed independently.

A control unit 20 is equipped with a communication tool 501.

The communication tool (501) uses Bluetooth (501A), WiFi (501C), SIGFOX (501D), or Xbee (not shown) etc.

When using WiFi (501C) as the communication tool 501, standards such as IEEE 802.11a to IEEE 802.11ac are used.

The standard may be any standard as long as it is publicly certified.

Also, a standard widely used from now on, such as SigFox (501D) may be used.

The communication tool (501) may be composed of Bluetooth (501A) and a mobile phone (501B).

In this embodiment, a communication tool (501) is comprised of a Bluetooth (501A) and a mobile phone (501B).

The mobile phone (501B) includes a control unit (C2) and a storage unit (recording unit) (521), and the mobile phone (501B) includes an AI software (551).

In a mobile phone (501B), the change of the exercise data of the user can be displayed a graphical representation by an action of the data processing software (550) and an AI software (551).

A communication device (501) transmits the data created by the AI software (551) to a control unit (C3) of a cloud (552).

Although an AI software (551) is described as being included in a control unit (20) and a control unit (C2) of the mobile phone (501B), the AI software arranged in a cloud may be used by the communication tool.

registered users (504) can access a cloud (552), and by using the accumulated data, it is possible to confirm the physical condition and to continue the exercise safely.

A cloud server (552) is a storage unit (recording unit) (521) and is managed by a manager who operates a management PC (503).

In the case that an administrator is a doctor, a physiotherapist, an occupational therapist, or a nurse, etc., a range of an alarm from the obtained result can be defined more accurate remote motion control becomes possible.

Namely, using a switch on a control unit input side shown in FIG. 23, rehabilitation medicine diagnosis and intervention by a doctor, nurse, or a physical therapist become easy.

Moreover, when a cloud server (552) is a server connected to the Internet, it can be managed and used by the operation of the server itself.

The OUTPUT 1 (92) displays a back and forth direction motion exercise data (92 a) and a rocking movement data (92 b), which are digitally converted an exercise data such as a display unit (327) of Example 3, display units (414, 415, 416, 417) of Example 4 and an external output device (91) to the exercise display screen illustrated in the FIG. 28.

OUTPUT 3 (94) is the data output, and data display on a mobile phone (501 B).

OUTPUT 4 (95) is communication to a cloud server using a mobile phone (501B) and WiFi (501C) or SIGFOX (501D) etc.

An input-and-output situation of an exercise data of FIG. 23 is described with referring FIG. 1.

A distance detection sensor (16), a number-of-times sensor (18), a rocking number setting switch (7h), a moving speed setting switch (7f), a reciprocating motion number setting switch (7j) and a communication device are connected to an input side of a control unit shown in FIG. 23 through the transmission route (14), and a rocking number setting switch (7h), a moving speed setting switch (7f), a reciprocating motion number setting switch (7j), a brake (17), a motor (19), external output device (91) and a communication device are connected to an output side of it through the transmission route (14).

In addition, it is not necessary to provide an external output device (91), the detection value of sensors (16, 18) can be output to the outside by the external output device (91).

Figure 29:
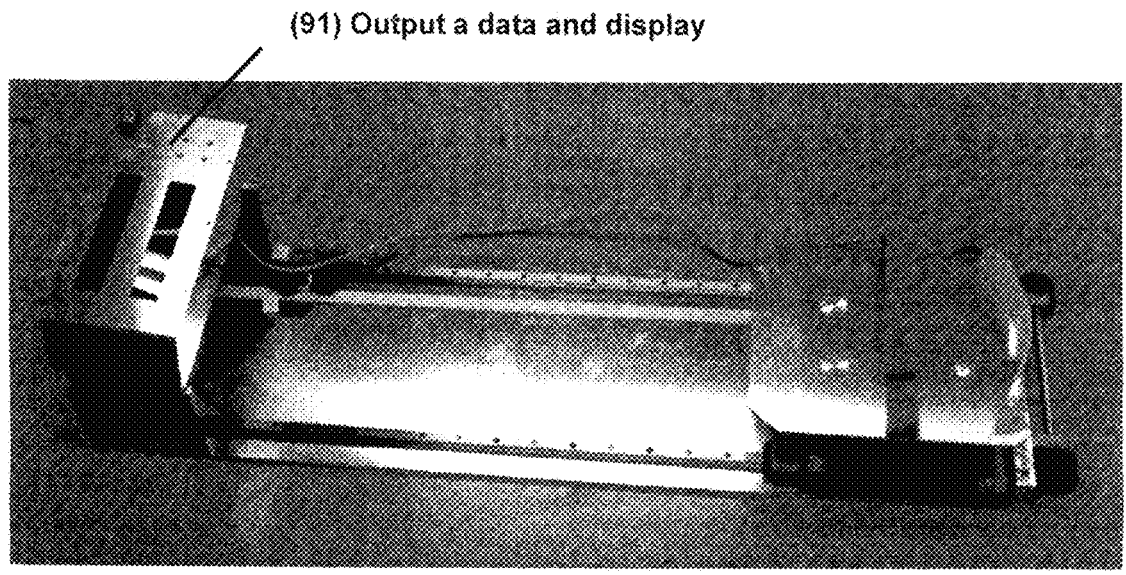
FIG. 29 is a reference diagram showing the present device for research based on Example 4.

The current output situation of OUTPUT 1 (92) is displayed on the display of the reference diagram of FIG. 29 and can be confirmed in Table 1 or Table 3.

A distance detection sensor (16) detects the rotational speed of the rear wheel (9), namely, the movement speed of the training board (1).

Although a training board (1) is reciprocating, and the movement direction is changed alternately, an average value of exercise data from a distance detection sensor (16) can be calculated by an AI software (551) in a control unit (20).

Furthermore, because, in the case that an administrator is a doctor, a physiotherapist, an occupational therapist, or a nurse, etc., a range of an alarm from the obtained result can be defined more accurate remote motion control becomes possible, the movement speed of the training board (1) can be set up by a speed setting switch (7f) to a control unit (20).

And, the optimal value of the reciprocation of a training board (1) can be set in a control unit (20) by reciprocating motion number setting switch (7 j).

Moreover, in the mobile phone of Example 3, the maximum value of the rocking of a training board 1 can be set in a control unit (20) by a setting the rocking number.

Depending on the condition of the patient, approximately value of speed 50 cm per second from the minimum speed of 5 cm per second can be set to a control unit (20) by a moving speed setting switch (7f).

And, a control unit (20) actuates all brakes (17) breaking and suspending the rear wheels (9) and front wheels (11) in the case that the average speed that is calculated with control unit (20) fell below the speed that was set up by a speed setting switch (7f).

And, it is not possible to exercise once again, because the brakes (17) are not disarmed if a release switch (7i) is not operated.

The exercise data from a distance detection sensor (16) is analyzed by Ai software and may be used as a standard value of reciprocation.

Namely, output and input from the control unit (20) are possible.

In this way, output and input about the amount of exercise of reciprocation and rocking from the control unit 20 with using a rocking number setting switch (7h), a moving speed setting switch (7f), a reciprocating motion number setting switch (7j) is possible.

A control unit (20) outputs data to the brake 17, the motor 19, and the external output device (91).

A brake (17) and a motor (19) are controlled by a control unit (20) according to a fixed calculated value (standard judgment value).

Moreover, a brake (17) and the motor (19) are controlled by a fixed calculated value (standard judgment value), and also it is possible to control by a numerical value within a fixed range based on the judgment of an expert such as a doctor, physiotherapist, occupational therapist or nurse.

Accumulation of this information can make the standard judgment value more accurate.

As a result, appropriate information can be provided to the judgment of the expert.

I explain FIG. 24 and FIG. 25.

FIG. 24 is a flowchart in case, which focuses on a radio communications system exercise data is read from a sensor (16, 18) in (Step 1) of FIG. 24, a processing software (550) works at (Step 2), exercise data is changed into the digital data (16*a*) (the notation to the table 1 is possible) and the digital data (18*a*) (the notation to the table 3 is possible), and the number of times of enforcement on the external output unit (91) can be written.

The number is displayed on the external output device (91) shown in the reference diagram of FIG. 29.

the existence of AI software is confirmed in (Step 3), and the AI software (551 is installed in the embodiment 1.

the AI software 551 is operated in (Step 4), the exercise data of Table 1 or Table 3 of the data of any one person shown in Table 2 or Table 4, that is, data of an exercise person is analyzed, and an average value, maximum value, and minimum value of necessary exercise data are calculated automatically.

This result is the basic analysis value.

And the results obtained by analysis, as shown in Table 2 or Table 4 are accumulated.

Step 5 shows in the case when the AI software (551) is not installed in step 4, to transmit data to the mobile phone (501B) namely a control unit (C2) of external setting, to transmit it to the control unit (C3) of a cloud or server by using router transmission with WiFi (501C), or when transmitting it using SIGFOX (501D) to transmit it directly to the control unit (C3) of a cloud server.

In Step 6, it is confirmed whether the AI software (551) has been worked after being transmitted to the mobile phone (501B) by Bluetooth (501A).

Operation of the AI software (551) enables output to the display screen of the mobile phone (501B), accumulation of processing data, and display of analysis results such as the user's exercise range.

Similar to step 4, data of any one of person shown in the Table 2 or the Table 4, namely, the exercise person has a mobile phone (501B) is analyzed from the exercise data of Table 1 or Table 3, and make it possible to display a graphical representation regarding to accumulated exercise data for a fixed period.

Namely, an average value, maximum value, and minimum value of exercise data are calculated automatically.

And the data is accumulated.

The accumulated data can be displayed as a graphical representation.

Although Table 2 or Table 4 is a data accumulation table for many people, a data accumulation table for individuals is created.

Then, the accumulated processing data is transmitted to a cloud.

In (step 7), although it transmits to control unit of a cloud or a server, when AI software (551) does not operate or it can not transmit, it returns to (step 0).

When the AI software (551) operates, as in step 4, from the exercise data of Table 1 and Table 3, anyone person of shown in the Table 2 and the Table 4, that is, the data of the exercise person is analyzed, and an average value, maximum value, and minimum value of exercise data are calculated automatically.

And the results obtained by analysis as shown in Table 2 and Table 4 are accumulated.

A mobile phone (501B) is one unit to the exercise data of the sensor (16, 18) and is compared with the personal identification data as needed and analyzed.

In particular, when the degree of care is determined a physical condition judgment value, standard judgment value can be collected in time series, analyzed, and output, so it becomes easy to continue exercise or to identify the optimum number of exercises.

And also, the arrangement of data can be automated, and labor-saving of experts can be realized.

FIG. 25 is a flowchart in case, which focuses on the processing of an AI software.

In Step 1 of FIG. 25, exercise data from the sensors (16 and 18) is read, in (Step 2), time data is read from a time measurement apparatus, in (Step 3), personal identification data such as a judgment value of physical condition is read from personal identification data (510), in (Step 4), it is converted by the operation of processing software of the control unit into digital data, in (Step 5) a processing software is operated and conversion to digital data that enables the display of the Table 1 or the Table 3 above is confirmed, when activated, it output to the exercise devise display screen exemplified in the display unit (327) of Example 3, the display units (414), (415), (416) and (417) of Example 4 and the external output device (91) shown in the reference view of FIG. 28.

In Step 6 the operation of the AI software (551) of the control unit installed in the physical function training device is confirmed.

When working, it calculates the basic analysis value, and the basic analysis value of the obtained exercise data is subjected to contrastive analysis to personal data and time data.

Then, the basic analysis value is accumulated, and the accumulated analysis value is calculated.

The numerical value of the basic analysis value is one line of the data line of Table 2 or Table 4.

Table 2 or Table 4 shows accumulated analysis value when based on a facility or an administrator.

The individual is detailed in step 6 of FIG. 24.

Subsequently, a physical condition judgment value that has a correlation to a personal data and accumulated data are subjected to contrastive analysis, and standard judgment value is calculated.

Furthermore, a reference interval is calculable by taking in a specialist's opinion and using an external PC.

These calculation results can be output to the mobile phone display screen.

Moreover, data is accumulated on a cloud server.

Step 7 is the same as step 6 in FIG. 24.

In step 8, although it transmits to control unit of a cloud or a server, when AI software (551) does not operate, or it can not transmit, it returns to (step 0).

The case where the AI software 551 works is similar to step 6.

The control unit of the cloud or server that accumulated each data can be used to manage the system, and it can be used the data by individual exercisers and also by exercise administrators, affiliations or facility units.

FIG. 26 shows procedures that an AI software calculates standard judgment value, and that the obtained standard judgment value is contrasted with an exercise data currently on training, and in the case to alert.

In Step 1 of FIG. 26, exercise data from a sensor (16, 18) and time and personal identification data are read and are converted into digital data by operation of processing software.

An AI software works at (Step 2).

In Step 3, a basic analysis value described step 4 of FIG. 24 associates with a personal identification data.

An accumulated analysis value is accumulated and memorized.

In Step 4, a judgment value of a physical condition is extracted from a personal identification data.

a degree of care is set as the judgment value in this application.

In Step 5, the criteria for replacing the degree of care with a numerical value that can be analyzed is shown.

the degree of care is converted into a numerical value that can be measured as follows.

The criteria of degree of care as following; "Need support 1" is 7, "Need support 2" is 6, "Need care 1" is 5, "Need care 2" is 4, "Need care 3" is 3, "Need care 4" is 2, and "Need care 5" is 1, and each replaces In addition, in order to use the degree of care, which the specialist defined as a judgment value, it is changed to a numerical value, but it may also be used without changing to a numerical value.

In Step 6, standard judgment value (the average value, the maximum value, and the minimum value or the average speed of the back and forth direction movement distances, or value of a rocking number can be used) is calculated.

The calculation method is to group the accumulated analysis value by the numerical value of STEP4, and the average value, the maximum value, the minimum value and the average speed of the back and forth direction movement distances, or value of rocking number be calculated.

standard judgment value is based on the fact that the average value, maximum value, minimum value, average speed of exercise distance, or value of rocking number are correlated with a numerical value of the value of nursing care replaced.

an average value, a maximum value, a minimum value, and an average speed of the back and forth direction movement distances, or a value of a rocking number can be used as standard judgment value.

In Step 7, performed contrastive analysis is performed to standard judgment value and an exercise data currently on training.

A mobile phone (501B) is one pair unit to the exercise data of the sensor (16, 18) and is compared with the personal identification data as needed and analyzed.

By the result, processings such as an alarm is enforced.

As standard judgment value, maximum value and the minimum value of the back and forth direction movement distance can be used as range designations and are desired.

The average value and the average speed of the back and forth direction movement distance and value of a rocking number can be used directly as standard judgment value.

Accumulation of each data from an exercise data to standard judgment value is effective for improvement of the accuracy of the standard judgment value and management for individual use and is implemented continuously.

It is possible that output to a mobile phone display screen, and administration (verification by the specialist in standard judgment value) and utilization (an individual, an administrator, and an institution) by a cloud and a server.

By giving feedback to a specialist, a specialist's work can be laborsaving.

It is also effective to add and change a specialist's knowledge.

To process such as an alarm enforces, If the numerical value which added and defined the knowledge of the specialist who set based on the Standard judgment value and if the Standard judgment value is exceeded, a brake is applied, or apply load similarly.

Moreover, when not reaching, it means that it is forced to operate.

The basis, which was able to make the degree of care the judgment value is shown in the following correlation analysis.

A study was conducted on the correlation between the accumulated analysis value and the judgment value as a factor for deciding standard judgment value described in FIGS. 25 to 27, and the following results were obtained.

In the article of Non-Patent literature 15, Results were obtained that there was significant correlation between exercise distance and average speed to a numerical value of a converted degree of care as the maximum motion distance ($r=0.702$, $p<0.01$), minimum motion distance ($r=0.608$, $p<0.05$), average motion distance ($r=0.745$, $p<0.01$), average velocity ($r=664$, $p<0.01$).

In the article of Non-Patent literature 16, Results were obtained that there was a significant correlation between the value of the rocking number to a numerical value of converted care.

Moreover, the announcement that is the basis of the patent application to which I am going to apply the Patent regulation of the 2nd clause of Article 30 is a presentation in the 20th Annual Meeting of the Biophilia Rehabilitation Conference held on Oct. 29, 2016.

This presentation is the basis of the paper of Non-Patent Literature 15.

From this result, by the work of AI software and based on the degree of care, it becomes enabling for the person requiring care who had a fixed degree of care authorized to estimate the exercise distance and average speed and also a value of rocking number of each individual's exercise and safer functional training can be carried out by one person at home by alarming to a managing organization when those value of training departs from the value of it.

I explain FIG. 27 and FIG. 28.

FIG. 27 is a flow chart relating to an analysis of a back and forth direction motion exercise data and FIG. 28 is a flow chart relating to an analysis of a rocking motion exercise data analysis, and therefore will be described collectively.

Both Figures differ only in the statement of a back and forth direction motion exercise data and a rocking motion exercise data.

In Step 1, it is performed that; to read a personal identification data, which shows a physical condition such as (name, birth date, medical history, physical condition judgment value (degree of care, FIM, BBS-TUG, etc.,) person in charge, use facility and/or use place, etc.), to read exercise data (to read data from detection device that receives data related to foot movement, to read the number of times of operation from a number-of-times sensor, and to read movement distance or angle from movement distance or angle sensor), and to read time data (to read time from a time measurement apparatus).

In (Step 2) and (Step 3), based on time data from a back and forth direction movement data or a rocking movement data, the moving distance or rocking angle, or the average value and the maximum and minimum values of the velocity or angular velocity that are calculated, and it is accumulated as a basic analysis value.

It is conducted contrastive analysis to a personal identification data.

As shown in Table 1 or Table 3, analytical values are output so as to use available.

Output basic analysis values to the display screen.

Basic analysis values are accumulated.

In (Step 4), contrastive analysis is performed when a basic analysis value can be accumulated.

basic analysis values accumulated are analyzed, and an accumulated analysis value is calculated.

The basic analysis value, accumulated analysis value, and personal identification data are conducted contrastive analysis to individuals, administrators, and facilities.

A physical condition judgment value in personal identification data is compared.

A physical condition judgment value is a value based on a specialist's judgment, such as a degree of care, FIM, BBS, and TUG.

The judgment is done with using accumulated analysis values, which is recognized correlation with the physical condition judgment value.

In Step 5, standard judgment value is determined by conducting a contrastive analysis between an accumulated analysis value and a physical condition judgment value, which has a correlation.

Since this numerical value can determine the numerical value of the setting switch of FIG. 23, it can specify a safe amount of exercise automatically.

Also, by accumulating with time, the physical condition can be determined.

Furthermore, when a specialist uses a numerical value of the cloud (502) with using the management PS (503), an allowable range can be determined.

Namely, the automatic specification of a safe amount of exercise can help a specialist's judgment; and by adding a specialist judgment, since the analytical data of the AI software (551) such as a specification of an allowable range of data, can be highly-developed, it can become to exercise efficiently and much more safely.

Although the table 1 and Table 3 were shown, and troublesomeness of that analysis was clarified, the AI software of this analysis is as follows.

The AI software (551) shown below is a basic program for obtaining values of each row of Table 2 and Table 4 by automatic calculation and shows a program.

```
require 'win32ole'
require 'csv'
module Common_function
    def chack_folder(save_folder)
        if(Dir.exist?(save_folder)==false)
            Dir.mkdir(save_folder)
        end
    end
end
include Common_function
class MyExcel
    def initialize(personal_name,filename)
        @filename = filename
        @directory = Dir.pwd
        @collection_folder = "cal_data"
        @personal_folder = @collection_folder + personal_name
        @save_folder = @personal_folder + "/#{File.basename(@filename,".*")}"
        chack_folder(@collection_folder)
        chack_folder(@personal_folder)
        chack_folder(@save_folder)
        @excel = WIN32OLE.new('Excel.Application')
        print @directory + filename
        @workbook = @excel.workbooks.open(@directory + "/" + filename)
    end
    def code( )
        print "Please define code( ) of singular method in this instance"
    end
    def run( )
        code( )
    end
end
data_folder = "data"
personal_name = "/a"
target_folder = data_folder + personal_name
chack_folder(data_folder)
chack_folder(target_folder)
Dir.glob("#{target_folder}/*").each do |directory_name|
    excel = MyExcel.new(personal_name,directory_name)
    def excel.code( )
        begin
            num = @workbook.sheets[1].range("A65536").end(3).row
            p num
            record = [ ]
            for record_row in 23..num
                pre_record = [ ]
                seconds = @workbook.sheets[1].range("B18").value( )
                points = @workbook.sheets[1].range("B19").value( )
                interval = seconds.to_f / points.to_f
                @workbook.sheets[1].range("A#{record_row}:D#{record_row}").each do |col|
                    pre_record.push(col.value( ))
                end
                record.push(pre_record)
            end
            #CSV.open(Dir.pwd+"/KMS_yt020506_20110829_1356_1.csv", 'w') do |writer|
```

```
            # record.each do |row|
            #     writer << row
            # end
            #end
            @workbook.save( )
        ensure
            @workbook.close( )
            @excel.quit
        end
        data = 0
        num1 = 0
        record_num = [ ]
        record_data = [ ]
        for num in 2..record.length( )-1
            pre_data1 = record[num-2][3] - record[num-1][3]
            pre_data2 = record[num-1][3] - record[num][3]
            if pre_data1 <= 0 && 0 < pre_data2
                record_num.push([num1, num-1])
                num1 = num
            elsif pre_data2 < 0 && 0 < pre_data1
                record_num.push([num1,num-1])
                num1 = num
            end
        end
        speeds = [ ]
        begin
            term = 0
            print @directory + "/#{@save_folder}/data.csv"
            CSV.open(@directory + "/#{@save_folder}/data.csv", 'w') do |writer|
                writer << ["distance1","distance2","second","term","speed"]
                record_num.each do |row|
                    row1 = row[0]
                    row2 = row[1]
                    data1 = record[row1][3]
                    data2 = record[row2][3]
                    second = (row1-row2)*interval
                    writer << [data1,data2,second,term,(data1-data2)/second]
                    speeds.push((data1-data2)/second)
                    term = term + 1
                end
            end
        end
        begin
            term = 0
            CSV.open(@directory +"/#{@save_folder}/calculation_value.csv", 'w') do |writer|
                minus_speeds = speeds.select{|elem| elem < 0 }
                plus_speeds = speeds.select{|elem| elem >= 0 }
                writer << [@filename]
                writer << [ ]
                writer << ["plus speed max","plus speed min","plus speed average","plus speed standard deviation"]
                writer << [plus_speeds.max( ),plus_speeds.min( ),plus_speeds.inject(0.0){|r,i| r+=i }/plus_speeds.size,Math::sqrt(plus_speeds.inject(0){|x,y| x+y*y}/plus_speeds.length-(plus_speeds.inject(0){|x,y| x+y}/plus_speeds.length)**2)]
                writer << ["minus speed max","minus speed min","minus speed average","minus speed standard deviation"]
                writer << [minus_speeds.min( ).abs( ),minus_speeds.max( ).abs( ),(minus_speeds.inject(0.0){|r,i| r+=i }/minus_speeds.size).abs( ),Math::sqrt(minus_speeds.inject(0){|x,y| x+y*y}/minus_speeds.length-(minus_speeds.inject(0){|x,y| x+y}/minus_speeds.length)**2)]
            end
        end
    end
    excel.run( )
end
```

The above program is one to obtain the results of Table 2 or Table 4 for each exercise implementation.

AI software is advancing every day, and it is possible to construct a similar program from the book shown in Non-Patent literature 16 in addition to this.

The AI software (551) develops into a mechanism that automatically calculates a table creation of users of a specific facility at a certain time, automatic creation of Table 2 or the Table 4, or an exercise data of a specific person for one month.

Namely, the center of this patent, by using an AI software, has a function in which neither a researcher nor a user needs to calculate the Table 2 and the Table 4 to spend time, and does not need to create them about the Table 1 and the Table 3.

A physical condition judgment value was set as a degree of care as which correlation was regarded from the result of research of the Non-Patent Literature 15 and the Non-Patent Literature 16. Although standard judgment value, which was obtained was made into a back and forth direction distance of order (maximum value, average value, and minimum value) and the number of times of an average, and also the number of times of a rocking average, the correlation over other physical condition judgment values may be checked as research and accumulation of data will progress from now on.

In that case, another physical condition judgment value is also available, and about a rocking movement, the angular velocity also has the possibility of becoming the standard judgment value.

Namely, the accumulation of data in the future enables a new physical condition judgment value and standard judgment value.

Although the degree of care evaluated by the present invention was shown, as data accumulation will progress to a cloud (502) from now on, the optimal movement for a physical condition by FIM (functional Independent Measure) or various gait evaluation methods (one example: Berg Balance Scale-BBS TUG 10 m walk test) may be defined.

Namely, although the standard was made into the degree of care in this patent, an amount of exercise to the standard on which correlation was confirmed can be defined.

Cerebral function activation may have a possibility of being used as a physical condition judgment value.

The communication tool (501) uses WiFi, Bluetooth, SIGFOX, or Xbee, etc.

WiFi uses standards such as IEEE 802.11a to IEEE 802.11ac, and it may be anything if it can be used, but it requires a router connected to the Internet within its communication range.

Bluetooth, Sigfox, and Xbee are Commodity Standards, and anything is good if they can communicate.

In the present invention, Bluetooth is used.

A Bluetooth (501A) requires, for example, to be connected by a mobile phone (501B).

AI software is s arranged in a mobile phone (501B).

The AI software displays a monthly exercise status chart or graph of the owner of the mobile phone (501B).

In the case of a Sigfox, a radio communications system (501) transmits data to a cloud server (502) directly by OUTPUT2. And although not displayed in the case of WiFi, through a radio router and the Internet, it transmits a converted to CSV, unconverted data, or result of an automatic calculation if AI software (551) is loaded, to a cloud server (502), which is storing data.

I explain from FIG. 29 to FIG. 31.

FIG. 29 is a reference view of a kinetic exercise device shown in the patent literature.

The data output display unit (91) is the external output device (91) of FIG. 23.

a contact sensor 407 is one of the contact sensors (407a, 407b, 407c, and 407d) of the case of Example 4.

FIG. 30 is a reference view of the motivative exercise of the upper limbs, which used the rocking movement kinetic exercise device.

FIG. 31 is a reference Figure of motivative exercise of the upper limbs, which used a back and forth direction kinetic exercise device.

As mentioned above, although the embodiment of the present invention was explained in full detail, the present invention is not limited to the embodiment mentioned above, and various changes can be made within the scope of the present invention described in a claim.

In addition, in this specification, front and back and also the right and left direction of a physical function training device is set up in the same direction as front and back and also right and left the direction of the patient who uses a physical function training device.

INDUSTRIAL APPLICABILITY

It becomes easy to exercise a hand or a leg with disability simultaneously in the same direction (motivative exercise) safely at own home and to continue exercising by the function of the artificial intelligence and machine learning (AI software), which is arranged in a control unit.

Moreover, a specialist's laborsaving is realizable, while an arrangement of exercise data can be automated, and specification of the optimal number of times of exercises and management of an exercise situation becomes easy.

REFERENCE SIGNS LIST 20 control unit
320 control unit
429 control unit
521 storage part
16 distance detection sensor
18 number of times detection sensor
17 brakes (a brake device)
19 motor (a load device, a drive unit)
91 external output device
92 OUTPUT1 (92a and 92b)
93 OUTPUT2
94 OUTPUT3
95 OUTPUT4
501 radio communications system
502 cloud and database
550 processing software
551 machine learning and artificial intelligence (AI software)
1 a training board

CITATION LIST

Patent Literature

The provisional publication of a patent 2011-067635, Physical training device, Biophilia research institute limited company, Apr. 7, 2011, application-for-patent 2010-Oct. 20, 2010-235131, A61H 1/02

The provisional publication of a patent 2011-036707, Physical training device, Biophilia research institute limited company, Feb. 24, 2011, application-for-patent 2010-Oct. 20, 2010-235135, A63B 23/04

The provisional publication of a patent 2010-000363, Physical training device, Takizawa Shigeo and other, Jan. 7, 2010, application-for-patent 2009-Jul. 15, 2009-166407, A63B 23/04 the provisional publication of a patent 2009-291624, Physical training device, Takizawa Shigeo and other, Dec. 17, 2009, application-for-patent 2009-Jul. 15, 2009 166418, A63B 23/04

The provisional publication of a patent 2001-170207, Leg motivative exercise training device, Takizawa Shigeo, Jun. 26, 2001, application-for-patent 2000-Jun. 16, 2000-180958, A63B 23/04

The provisional publication of a patent 2000-233031, Physical training device, Takizawa Shigeo, Aug. 29, 2000, Japanese-Patent-Application-No. 11-Dec. 16, 1999, 358206, A63B 23/04

The U.S. Pat. No. 7,153,250 Method for managing exercise for functional recovery and muscle strengthening, Shigeo Takizawa, 26, Dec. 2006

The U.S. Pat. No. 7,481,739 Physical function training device, Shigeo Takizawa, U.S. Ser. No. 10/779,125

The U.S. Pat. No. 6,780,142 Physical function training device, Shigeo Takizawa, 24 Aug. 2004

The U.S. Pat. No. 3,978,497, Motivative exercise and lifting aid dual device, Shigeo Takizawa, 27, Dec. 2005

The US. APPL. 20080125294 PHYSICAL FUNCTION TRAINING DEVICE, Shigeo Takizawa, U.S. Ser. No. 11/949,089

The U.S. Pat. No. 6,978,497 Motivative exercise and lifting aid dual device, Shigeo Takizawa, 2000-06-21

The U.S. Pat. No. 6,625,846 Caster for robot, Shigeo Takizawa, Mar. 6, 1998

Non Patent Literature

Hideo Kijima, Shigeo Takizawa, et al., The rehabilitation and the related training devices which we have recommended", The Journal of the Japanese Clinical Orthopedics, 23 (58) (1998), pp 186-191. (JP)

Kenji Ushizawa, et al.: Statistical Evaluation of Rehabilitation to the Disabled Elderly based Takizawa-Program, Biophilia Rehabilitation Journal, 2-1, p 71-80, 2004.

S. Takizawa, T. Kimura, H. Kijima, Y. Okamoto, K. Nagaoka, Y. Morita, S. Endo, H. Nagasawa, M. Makita, K. Takizawa, Re-acquirement of Walking from Bedridden by the Motivative Exercise and Takizawa Method and Proposition of the Solution to the Aging Crisis BIOPHILIA Vol. 2015(2015) No. 1, Memorial Edition for the Linking ISSN Registration, p. 12-18.

Shigeo Takizawa, Tetsuhiko Kimura, Hideo Kijima, Yuzou Okamoto, kentaro Nagaoka, kyoko Takizawa, The Development of Devices for the MOTIVATIVE Exercise of Impaired Extremities, BIOPHILIA Vol. 2015(2015) No. 1 Memorial Edition for the Linking ISSN Registration p. 7-11.

S. Takizawa, T. Kijima, H. Kijima, K. Nagaoka, S. Kanai, Y. Morita, H. Nagasawa, S. Endo, K. Takizawa, Ambulation from Bedridden—Patient with Double Hemiplegia, BIOPHILIA Vol. 2015(2015) No. 1 Memorial Edition for the Linking ISSN Registration p. 16-18.

Shigeo Takizawa, Yoshiyasu Takefuji, Tomoji Ishimaru, Rika Wada, Hajime Takada, Tetsuhiko Kimura, Construction of Community Biophilia Rehabilitation Network for the Disabled Elderly, Biophilia Rehabilitation Journal, Vol. 6 (2010) No. 1 P 19-26.

Takizawa Shigeo, et al., Construction of Community Biophilia Rehabilitation Network by the Disabled Elderly and the Effect of Autonomous Kinetic Rehabilitation, Biophilia Rehabilitation Research, Vol. 6 (2010), No. 1, and pp 11-18.

Takizawa Shigeo, Syuji Kawai, Yasuhiro Matsuo, Yuka Deguti, Hiroyoshi Yamamoto, Yoshiyasu Takefuji, Effect of the Motivative Exercise Studied by fNIRS: Introduction to the Rehabilitation Day Care Users, BIOPHILIA, 2-1, 25-34.

Yoshiko Morita, Shigeo Takizawa, Brain Activity during Motivative Exercise Versus Passive ROM Exercise by fMRI, BIOPHILIA Vol. 2(2012) No. 1, p. 35-40.

Rika Wada, Taki Shigeo Takizawa, BRAIN ACTIVITY MEASUREMENT BY FUNCTIONAL NEAR INFRA-RED SPECTROSCOPY BETWEEN MOTIVATE EXERCISE AND PASSIVE ROM EXERCISE TO THE OUTPATIENTS OF REHABILITATION DAYCARE SERVICE, BRC 2013, PP18, Chieti, Italy.

Yoshiko Morita, Taki Shigeo Takizawa, BRAIN ACTIVITY ASSESSMENTS BY FUNCTIONAL NEAR INFRA-RED SPECTROSCOPY BETWEEN THE MOTIVATE EXERCISE AND PASSIVE ROM EXERCISE TO THE DAYCARE STROKE PATIENTS IN OUR REHABILITATION HOSPITAL, IBRC 2013, PP17, Chieti, Italy.

Shigeo Takizawa, Tetsuhiko Kimura, Hideo Kijima, Yuzou Okamoto, kentaro Nagaoka, kyoko Takizawa, The Development of Devices for the MOTIVATIVE Exercise of Impaired Extremities, BIOPHILIA Vol. 2015(2015) No. 1 Memorial Edition for the Linking ISSN Registration p. 7-11.

TAKIZAWA Shigeo, Yoshiyasu Takefuji, Akira Iemoto, Hajime Takada, Kentaro Nagaoka, Thermographic analysis of Two Kind of Motivative Exercise, Biomedical Thermology, 26 (2007). p 98-103.

Trademark registration 5678648, motivative exercise, classification 41, Biophilia research institute limited company, registration date 2014 Jun. 20.

Shigeo Takizawa, Rika Wada, Toshihiro Tachibana, Junichi Ozawa, Toshiyuki Tanaka, Implementation of Knee Motivative Exercise Corresponding to Category of the Japanese Care Insurance, BIOPHILIA (2017) p. 1-6.

Rika Wada, Shigeo Takizawa, Toshihiro Tachibana, Yoshiko Morita, Toshiyuki Tanaka, Yoshiyasu Takefuji, Hajime Takada, Evaluation of Body Condition by the implementation of Motivative Exercise, BIOPHILIA (2017) p. 7-12.

Yoshiyasu Takefuji, Super Practice Ensemble Machine Learning, Kindaikagaku Company (2016 December release, JP)

Jill Whitall, et al.: Repetitive Bilateral Arm Training With Rhythmic Auditory Cueing Improves Motor Function in Chronic Hemiparetic Stroke. Stroke 2000; 31:2390.

The invention claimed is:

1. A physical function training device comprising:
 a training board which is set in motion with upper limbs or lower limbs,
 a detection device including frequency detection sensor, the detection device detecting operation data associated with a reciprocating motion or a rocking motion of the training board,
 a control unit that analyzes the operation data, and
 a recording unit which records personal identification data, the operation data, time data including an operation time of the detection device, and a basic analysis value,
 wherein the personal identification data including evaluation data authenticated by an evaluation system for evaluating a physical function and personal data,
 wherein the operation data includes frequency data indicating a frequency of the reciprocating motion or the rocking motion of the training board, the frequency data being detected by the frequency detection sensor,
 wherein the control unit calculates an average value, a maximum value, and a minimum value in the frequency data based on the operation data and the time data, and
 wherein the control unit calculates the basic analysis value with extracting at least one of the calculated average, maximum, or minimum values that corresponds to the evaluation data by comparing the calculated average, maximum, or minimum values with the evaluation data.

2. The physical function training device according to claim 1,
wherein the control unit analyzes the operation data associated with the time data.

3. The physical function training device according to claim 1,
wherein the detection device includes a distance detection sensor for detecting distance data or angle data related to the reciprocating motion or the rocking motion of the training board,
the operation data includes the distance data or the angle data, and
the frequency data includes at least one of values of a reciprocating motion distance, a rocking motion angle, or a speed of reciprocating or rocking motion.

4. The physical function training device according to claim 1,
wherein the control unit calculates the basic analysis value by using each operation data,
the control unit accumulates a plurality of the basic analysis values, and
the control unit analyzes accumulated data accumulated the basic analysis values so as to output, average, maximum, and minimum values as accumulated analysis values.

5. The physical function training device according to claim 1,
wherein the control unit analyzes the accumulated analysis values in association with personal identification data recorded in the recording unit so as to
obtain a standard judgment value for judging a physical condition of a user.

6. A physical function training system comprising:
a physical function training device,
a data control unit, and
a recording unit,
wherein the physical function training device includes:
a training board which is set in motion with upper limbs or lower limbs,
a detection device including a frequency detection sensor, the detection device detecting operation data associated with a reciprocating motion or a rocking motion of the training board,
and a control unit capable of communicating the operation data,
wherein the data control unit receives the operation data by using a communication device, and the data control unit analyzes the operation data,
wherein the personal identification data including evaluation data authenticated by an evaluation system for evaluating a physical function and personal data,
wherein the recording unit records personal identification data, the operation data, time data including operation time of the detection device, and a basic analysis value,
wherein the personal identification data including evaluation data authenticated by an evaluation system for evaluating a physical function and personal data,
wherein the operation data includes frequency data indicating a frequency of the reciprocating motion or the rocking motion of the training board, the frequency data being detected by the frequency detection sensor,
wherein the control unit calculates an average value, a maximum value, and a minimum value in the frequency data based on the operation data and the time data, and
wherein the control unit calculates the basic analysis value with extracting at least one of the calculated average, maximum, or minimum values that corresponds to the evaluation data by comparing the calculated average, maximum, or minimum values with the evaluation data.

7. The physical function training system according to claim 6, wherein the data control unit analyzes the operation data associated with the time data.

8. The physical function training system according to claim 6,
wherein the detection device includes a distance detection sensor for detecting distance data or angle data related to the reciprocating motion or the rocking motion of the training board,
the operation data includes the distance data or the angle data, and
the frequency data includes at least one of values of a reciprocating motion distance, a rocking motion angle, or a speed of reciprocating or rocking motion.

9. A method for physical function training comprising:
a first step of setting upper limbs or lower limbs on a training board,
a second step of detecting operation data associated with a reciprocating motion or a rocking motion of the training board by a detection device including frequency detection sensor, the operation data including frequency data indicating a frequency of the reciprocating motion or the rocking motion of the training board, and the frequency data being detected by the frequency detection sensor,
a third step of analyzing operation data by a control unit,
a fourth step of recording personal identification data, the operation data, and time data, the time data including an operation time of the detection device, and a basic analysis value in a recording unit,
wherein the personal identification data with including evaluation data authenticated by an evaluation system for evaluating a physical function and personal data,
a fifth step of calculating an average value, a maximum value, and a minimum value in the frequency data based on the operation data and the time data by the control unit,
a sixth step of calculating the basic analysis value by extracting at least one of the calculated average, maximum, or minimum values that correspond to the evaluation data by comparing the calculated average, maximum, or minimum values with the evaluation data by the control unit.

10. A method for physical function training comprising:
a first step of setting upper limbs or lower limbs on a training board,
a second step of detecting operation data associated with a reciprocating motion or a rocking motion of the training board by a detection device including frequency detection sensor, operation data including frequency data indicating a frequency of the reciprocating motion or the rocking motion of the training board, and the frequency data being detected by the frequency detection sensor,
a third step of receiving the operation data by a communication device,
a fourth step of analyzing the operation data by the data control unit, a fifth step of recording personal identification data, the operation data, time data including an operation time of the detection device, and a basic analysis value in a recording unit, wherein the personal identification data including evaluation data authenticated by an evaluation system for evaluating a physical function and personal data, a sixth step of indicating a frequency of the reciprocating motion or the rocking motion of the training board in the operation data, a seventh step of calculating an average value, a maximum value, and a minimum value in the frequency data based on the operation data and the time data by the control unit, an eighth step of calculating the basic analysis value by extracting at least one of the calculated average, maximum, or minimum values that correspond to the evaluation data by comparing the calculated average, maximum, or minimum values with the evaluation data by the control unit.

* * * * *